US011246672B2

(12) United States Patent
Landey et al.

(10) Patent No.: US 11,246,672 B2
(45) Date of Patent: Feb. 15, 2022

(54) AXIAL MOTION DRIVE DEVICES, SYSTEMS, AND METHODS FOR A ROBOTIC MEDICAL SYSTEM

(71) Applicant: Auris Health, Inc., Redwood City, CA (US)

(72) Inventors: Casey Teal Landey, San Francisco, CA (US); Jiayi Lin, San Mateo, CA (US); Chauncey F. Graetzel, Palo Alto, CA (US); Alan Lau Yu, Union City, CA (US); Jason J. Hsu, Mountain View, CA (US); Zachary Stahl Morrison, Dallas, TX (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/994,504

(22) Filed: Aug. 14, 2020

(65) Prior Publication Data
US 2021/0045823 A1 Feb. 18, 2021

Related U.S. Application Data

(60) Provisional application No. 62/887,518, filed on Aug. 15, 2019.

(51) Int. Cl.
*A61B 34/00* (2016.01)
*A61B 34/37* (2016.01)
(Continued)

(52) U.S. Cl.
CPC .............. *A61B 34/71* (2016.02); *A61B 34/20* (2016.02); *A61B 34/30* (2016.02); *A61B 34/37* (2016.02);
(Continued)

(58) Field of Classification Search
CPC . A61B 34/37; B25J 9/02; B25J 9/1035; B25J 9/1623
(Continued)

(56) References Cited

U.S. PATENT DOCUMENTS 6,312,440 B1 * 11/2001 Hood ..................... A61F 9/013
606/166
6,726,675 B1 4/2004 Beyar
(Continued)

FOREIGN PATENT DOCUMENTS

WO 2009137410 A1 11/2009
WO 2010025336 A1 3/2010
(Continued)

OTHER PUBLICATIONS

Office Action for U.S. Appl. No. 16/994,501 dated Nov. 23, 2020, 8 pages.
(Continued)

*Primary Examiner* — Khoi H Tran
*Assistant Examiner* — Rodney P King
(74) *Attorney, Agent, or Firm* — Chang & Hale LLP

(57) ABSTRACT

Certain aspects relate to systems and techniques for driving axial motion of a shaft of a medical instrument using a drive device. Axial motion can include insertion and/or retraction of the instrument. For example, a robotic medical system can include a medical instrument comprising an instrument base and a flexible shaft configured for insertion into a patient, and a first robotic arm attachable to the instrument base of the medical instrument. The system also includes a drive device configured to engage the flexible shaft, and a second robotic arm attachable to the drive device. The second robotic arm is configured to operate the drive device to drive axial motion of the flexible shaft, and the first
(Continued)

robotic arm is configured to move in coordination with operation of the drive device.

29 Claims, 44 Drawing Sheets

(51) Int. Cl.
  *B25J 9/02* (2006.01)
  *B25J 9/10* (2006.01)
  *B25J 9/16* (2006.01)
  *A61B 34/30* (2016.01)
  *A61B 34/20* (2016.01)

(52) U.S. Cl.
  CPC .............. *B25J 9/02* (2013.01); *B25J 9/1035* (2013.01); *B25J 9/1623* (2013.01); *B25J 9/1628* (2013.01); *A61B 2034/2051* (2016.02); *A61B 2034/2055* (2016.02); *A61B 2034/2065* (2016.02); *A61B 2034/301* (2016.02); *A61B 2034/302* (2016.02)

(58) Field of Classification Search
  USPC ......................................................... 606/130
  See application file for complete search history.

(56) References Cited

U.S. PATENT DOCUMENTS

| | | | |
|---|---|---|---|
| 7,615,042 | B2 | 11/2009 | Beyar et al. |
| 7,789,874 | B2 | 9/2010 | Yu et al. |
| D626,250 | S | 10/2010 | Wenderow et al. |
| 7,887,549 | B2 | 2/2011 | Wenderow et al. |
| 8,146,874 | B2 | 4/2012 | Yu |
| 8,257,302 | B2 | 9/2012 | Beyar et al. |
| D674,484 | S | 1/2013 | Murphy et al. |
| 8,399,871 | B2 | 3/2013 | Beyar et al. |
| D680,645 | S | 4/2013 | Murphy et al. |
| D685,468 | S | 7/2013 | Murphy et al. |
| 8,480,618 | B2 | 7/2013 | Wenderow et al. |
| 8,600,477 | B2 | 12/2013 | Beyar et al. |
| 8,694,157 | B2 | 4/2014 | Wenderow et al. |
| 8,755,124 | B2 | 6/2014 | Aschwanden et al. |
| 8,790,297 | B2 | 7/2014 | Bromander et al. |
| 8,827,948 | B2* | 9/2014 | Romo .................... A61B 34/35 604/95.04 |
| 8,828,021 | B2 | 9/2014 | Wenderow et al. |
| 8,868,231 | B2* | 10/2014 | Moore .................. B25J 9/0093 700/223 |
| 8,894,610 | B2 | 11/2014 | MacNamara et al. |
| 8,968,333 | B2 | 3/2015 | Yu et al. |
| 9,014,851 | B2 | 4/2015 | Wong et al. |
| 9,049,989 | B2* | 6/2015 | Crenshaw ........ A61B 17/12136 |
| 9,070,486 | B2 | 6/2015 | Guerrera et al. |
| 9,089,261 | B2* | 7/2015 | Greenburg ......... A61B 1/00147 |
| 9,095,681 | B2 | 8/2015 | Wenderow et al. |
| 9,138,166 | B2 | 9/2015 | Wong et al. |
| 9,168,356 | B2 | 10/2015 | Wenderow et al. |
| 9,220,568 | B2 | 12/2015 | Bromander et al. |
| 9,314,306 | B2 | 4/2016 | Yu |
| 9,314,311 | B2 | 4/2016 | Wenderow et al. |
| 9,320,479 | B2 | 4/2016 | Wenderow et al. |
| 9,326,822 | B2 | 5/2016 | Lewis et al. |
| 9,345,859 | B2 | 5/2016 | Blacker |
| 9,402,977 | B2 | 8/2016 | Wenderow et al. |
| 9,408,669 | B2 | 8/2016 | Kokish et al. |
| 9,427,562 | B2 | 8/2016 | Blacker |
| 9,452,018 | B2 | 9/2016 | Yu |
| 9,452,277 | B2 | 9/2016 | Blacker |
| 9,545,497 | B2 | 1/2017 | Wenderow et al. |
| 9,549,783 | B2 | 1/2017 | Zirps |
| 9,554,774 | B2* | 1/2017 | Moore ................. A61B 8/5253 |
| 9,561,083 | B2 | 2/2017 | Yu et al. |
| 9,566,201 | B2 | 2/2017 | Yu |
| 9,622,827 | B2 | 4/2017 | Yu et al. |
| 9,623,209 | B2 | 4/2017 | Wenderow et al. |
| 9,636,184 | B2 | 5/2017 | Lee et al. |
| 9,710,921 | B2 | 7/2017 | Wong et al. |
| 9,713,509 | B2 | 7/2017 | Schuh et al. |
| 9,727,963 | B2* | 8/2017 | Mintz ................ A61B 1/00147 |
| 9,750,576 | B2 | 9/2017 | Murphy et al. |
| 9,763,741 | B2* | 9/2017 | Alvarez ............ A61M 25/0012 |
| 9,764,114 | B2 | 9/2017 | Murphy et al. |
| 9,770,194 | B2 | 9/2017 | Azagury et al. |
| 9,782,564 | B2 | 10/2017 | Zirps et al. |
| 9,789,285 | B1 | 10/2017 | Blacker |
| 9,814,534 | B2 | 11/2017 | Wenderow et al. |
| 9,833,293 | B2 | 12/2017 | Wenderow et al. |
| 9,839,481 | B2 | 12/2017 | Blumenkranz et al. |
| 9,855,101 | B2 | 1/2018 | Wenderow et al. |
| 9,931,025 | B1 | 4/2018 | Graetzel et al. |
| 9,931,170 | B2* | 4/2018 | Auld ...................... A61B 34/37 |
| 9,943,958 | B2 | 4/2018 | Blacker et al. |
| 9,962,229 | B2 | 5/2018 | Blacker et al. |
| 9,981,109 | B2 | 5/2018 | Blacker et al. |
| 9,993,313 | B2 | 6/2018 | Schuh et al. |
| 9,993,615 | B2 | 6/2018 | Blacker |
| 10,085,805 | B1 | 10/2018 | Blacker |
| 10,123,843 | B2 | 11/2018 | Wong et al. |
| 10,130,345 | B2 | 11/2018 | Wong et al. |
| 10,145,747 | B1 | 12/2018 | Lin et al. |
| 10,159,533 | B2 | 12/2018 | Moll et al. |
| 10,219,874 | B2 | 3/2019 | Yu et al. |
| 10,238,456 | B2 | 3/2019 | Murphy et al. |
| 10,245,112 | B2 | 4/2019 | Kottenstette et al. |
| 10,271,910 | B2 | 4/2019 | Wenderow et al. |
| 10,285,574 | B2 | 5/2019 | Landey et al. |
| 10,299,867 | B2 | 5/2019 | Wenderow et al. |
| 10,299,870 | B2 | 5/2019 | Connolly et al. |
| 10,307,570 | B2 | 6/2019 | Blacker |
| 10,342,953 | B2 | 7/2019 | Wenderow et al. |
| 10,350,009 | B2* | 7/2019 | Panescu ................... A61B 1/06 |
| 10,376,672 | B2 | 8/2019 | Yu |
| 10,398,518 | B2 | 9/2019 | Yu et al. |
| 10,426,558 | B2* | 10/2019 | Scholan ................. A61B 90/50 |
| 10,426,559 | B2 | 10/2019 | Graetzel et al. |
| 10,426,926 | B2 | 10/2019 | Blacker et al. |
| 10,448,809 | B2* | 10/2019 | Fitzmaurice ....... A61B 1/00135 |
| 10,499,999 | B2 | 12/2019 | Yu |
| 10,500,001 | B2 | 12/2019 | Yu et al. |
| 10,531,864 | B2 | 1/2020 | Wong et al. |
| 10,539,478 | B2 | 1/2020 | Lin et al. |
| 10,543,047 | B2 | 1/2020 | Yu |
| 10,549,071 | B2 | 2/2020 | Falb et al. |
| 10,556,092 | B2 | 2/2020 | Yu et al. |
| 10,561,821 | B2 | 2/2020 | Wenderow et al. |
| 10,569,052 | B2 | 2/2020 | Kokish et al. |
| 10,583,276 | B2 | 3/2020 | Zirps |
| 10,611,391 | B1 | 4/2020 | Klem et al. |
| 10,631,949 | B2 | 4/2020 | Schuh et al. |
| 10,653,863 | B1 | 5/2020 | Blacker et al. |
| 10,667,720 | B2 | 6/2020 | Wong et al. |
| 10,687,903 | B2 | 6/2020 | Lewis et al. |
| 10,702,348 | B2 | 7/2020 | Moll et al. |
| 10,709,510 | B2 | 7/2020 | Kottenstette |
| 10,716,726 | B2 | 7/2020 | Bergman et al. |
| 10,743,751 | B2 | 8/2020 | Landey et al. |
| 10,765,303 | B2 | 9/2020 | Graetzel et al. |
| 10,765,487 | B2 | 9/2020 | Ho et al. |
| 10,779,775 | B2 | 9/2020 | Bergman et al. |
| 10,779,895 | B2 | 9/2020 | Wenderow et al. |
| 10,786,329 | B2 | 9/2020 | Schuh et al. |
| 10,792,112 | B2 | 10/2020 | Kokish et al. |
| 10,792,466 | B2 | 10/2020 | Landey et al. |
| 10,799,305 | B2 | 10/2020 | Murphy et al. |
| 10,813,539 | B2 | 10/2020 | Graetzel et al. |
| 10,820,952 | B2 | 11/2020 | Yu |
| 10,828,463 | B2 | 11/2020 | Blacker |
| 10,835,329 | B2 | 11/2020 | Wenderow et al. |
| 10,849,702 | B2 | 12/2020 | Hsu et al. |
| 10,850,013 | B2 | 12/2020 | Hsu et al. |
| 10,864,629 | B2 | 12/2020 | Guerrera et al. |
| 10,881,474 | B2 | 1/2021 | Blacker et al. |
| 10,898,276 | B2 | 1/2021 | Graetzel et al. |

(56) References Cited

U.S. PATENT DOCUMENTS

| | | | |
|---|---|---|---|
| 10,900,771 B2 | 1/2021 | Kottenstette et al. | |
| 10,912,624 B2 | 2/2021 | Prentakis et al. | |
| 10,932,691 B2 | 3/2021 | Sramek et al. | |
| 10,932,861 B2 | 3/2021 | Sramek et al. | |
| 10,953,206 B2 | 3/2021 | Blacker | |
| 10,987,491 B2 | 4/2021 | Wenderow et al. | |
| 10,994,102 B2 | 5/2021 | Blacker | |
| 11,007,348 B2 | 5/2021 | Blacker | |
| 11,109,919 B2 | 9/2021 | Murphy et al. | |
| 11,109,921 B2 | 9/2021 | Kottenstette et al. | |
| 11,114,918 B2 | 9/2021 | Zirps et al. | |
| 2004/0087914 A1* | 5/2004 | Bryan | A61B 17/3421 604/264 |
| 2008/0058776 A1 | 3/2008 | Jo et al. | |
| 2009/0131955 A1 | 5/2009 | Wenderow et al. | |
| 2011/0015648 A1 | 1/2011 | Alvarez et al. | |
| 2011/0144658 A1 | 6/2011 | Wenderow et al. | |
| 2013/0214912 A1 | 8/2013 | Beyar et al. | |
| 2013/0274657 A1 | 10/2013 | Zirps et al. | |
| 2014/0058321 A1 | 2/2014 | Wenderow et al. | |
| 2014/0066900 A1 | 3/2014 | Blacker | |
| 2014/0276233 A1 | 9/2014 | Murphy | |
| 2014/0277333 A1 | 9/2014 | Lewis et al. | |
| 2015/0005738 A1 | 1/2015 | Blacker | |
| 2015/0005745 A1 | 1/2015 | Bergman et al. | |
| 2015/0005865 A1 | 1/2015 | Bergman et al. | |
| 2015/0028195 A1 | 1/2015 | King et al. | |
| 2016/0124220 A1 | 5/2016 | Bueeler et al. | |
| 2016/0184032 A1* | 6/2016 | Romo | A61B 10/04 606/130 |
| 2016/0270865 A1 | 9/2016 | Landey et al. | |
| 2017/0189128 A1 | 7/2017 | Auld | |
| 2017/0290631 A1 | 10/2017 | Lee et al. | |
| 2017/0340396 A1 | 11/2017 | Romo et al. | |
| 2017/0348060 A1 | 12/2017 | Blacker | |
| 2018/0028781 A1 | 2/2018 | Murphy et al. | |
| 2018/0085031 A1 | 3/2018 | Azagury et al. | |
| 2018/0279852 A1 | 10/2018 | Rafii-Tari et al. | |
| 2018/0325499 A1 | 11/2018 | Landey et al. | |
| 2018/0360398 A1 | 12/2018 | Wenderow et al. | |
| 2019/0223974 A1 | 7/2019 | Romo et al. | |
| 2019/0262086 A1 | 8/2019 | Connolly et al. | |
| 2019/0269468 A1 | 9/2019 | Hsu et al. | |
| 2019/0307987 A1 | 10/2019 | Yu | |
| 2019/0336238 A1 | 11/2019 | Yu et al. | |
| 2019/0365491 A1 | 12/2019 | Yu | |
| 2019/0380797 A1 | 12/2019 | Yu et al. | |
| 2020/0008891 A1 | 1/2020 | Wenderow et al. | |
| 2020/0009354 A1 | 1/2020 | Wenderow et al. | |
| 2020/0016371 A1 | 1/2020 | Blacker | |
| 2020/0038123 A1 | 2/2020 | Graetzel et al. | |
| 2020/0129740 A1 | 4/2020 | Kottenstette et al. | |
| 2020/0155245 A1 | 5/2020 | Yu | |
| 2020/0155801 A1 | 5/2020 | Kokish et al. | |
| 2020/0170630 A1 | 6/2020 | Wong et al. | |
| 2020/0188043 A1 | 6/2020 | Yu et al. | |
| 2020/0206472 A1 | 7/2020 | Ma et al. | |
| 2020/0217733 A1 | 7/2020 | Lin et al. | |
| 2020/0230360 A1 | 7/2020 | Yu et al. | |
| 2020/0282186 A1 | 9/2020 | Blacker et al. | |
| 2020/0297973 A1 | 9/2020 | Blacker et al. | |
| 2020/0316340 A1 | 10/2020 | Wenderow et al. | |
| 2020/0323596 A1 | 10/2020 | Moll et al. | |
| 2020/0324084 A1 | 10/2020 | Falb et al. | |
| 2020/0337593 A1 | 10/2020 | Wong et al. | |
| 2020/0338308 A1 | 10/2020 | Saber et al. | |
| 2020/0352420 A1 | 11/2020 | Graetzel et al. | |
| 2020/0367726 A1 | 11/2020 | Landey et al. | |
| 2020/0367981 A1 | 11/2020 | Ho et al. | |
| 2020/0375671 A1 | 12/2020 | Wenderow et al. | |
| 2020/0383735 A1 | 12/2020 | Lewis et al. | |
| 2020/0405413 A1 | 12/2020 | Kokish et al. | |
| 2020/0405434 A1 | 12/2020 | Schuh et al. | |
| 2021/0008341 A1 | 1/2021 | Landey et al. | |
| 2021/0030492 A1 | 2/2021 | Wenderow et al. | |
| 2021/0038334 A1 | 2/2021 | Hsu et al. | |
| 2021/0045626 A1 | 2/2021 | Hsu et al. | |
| 2021/0045822 A1 | 2/2021 | Landey et al. | |
| 2021/0045824 A1 | 2/2021 | Landey et al. | |
| 2021/0059766 A1 | 3/2021 | Graetzel et al. | |
| 2021/0060767 A1 | 3/2021 | Guerrera et al. | |
| 2021/0077209 A1 | 3/2021 | Yu | |
| 2021/0077211 A1 | 3/2021 | Blacker et al. | |
| 2021/0093406 A1 | 4/2021 | Blacker et al. | |
| 2021/0093418 A1 | 4/2021 | Finocchi et al. | |
| 2021/0100980 A1 | 4/2021 | Blacker | |
| 2021/0108910 A1 | 4/2021 | Kottenstette et al. | |
| 2021/0121052 A1 | 4/2021 | Graetzel et al. | |
| 2021/0145305 A1 | 5/2021 | Sramek et al. | |
| 2021/0153954 A1 | 5/2021 | Sramek et al. | |
| 2021/0169588 A1 | 6/2021 | Graetzel et al. | |
| 2021/0178032 A1 | 6/2021 | Hsu et al. | |
| 2021/0196251 A1 | 7/2021 | Dull et al. | |
| 2021/0196293 A1 | 7/2021 | Lin et al. | |
| 2021/0196410 A1 | 7/2021 | Hsu et al. | |
| 2021/0220064 A1 | 7/2021 | Kottenstette et al. | |
| 2021/0220624 A1 | 7/2021 | Blacker | |
| 2021/0228841 A1 | 7/2021 | Falb et al. | |

FOREIGN PATENT DOCUMENTS

| | | |
|---|---|---|
| WO | 2010025338 A1 | 3/2010 |
| WO | 2010068783 A1 | 6/2010 |
| WO | 2010107916 A1 | 9/2010 |
| WO | 2011046874 A1 | 4/2011 |
| WO | 2011109282 A1 | 9/2011 |
| WO | 2011109283 A1 | 9/2011 |
| WO | 2011150526 A1 | 12/2011 |
| WO | 2012037213 A1 | 3/2012 |
| WO | 2012050877 A1 | 4/2012 |
| WO | 2012129374 A1 | 9/2012 |
| WO | 2013043804 A1 | 3/2013 |
| WO | 2013043872 A1 | 3/2013 |
| WO | 2014039838 A1 | 3/2014 |
| WO | 2014143746 A3 | 12/2014 |
| WO | 2015013470 A2 | 1/2015 |
| WO | 2015057821 A1 | 4/2015 |
| WO | 2015061756 A1 | 4/2015 |
| WO | 2015069804 A1 | 5/2015 |
| WO | 2015095149 A1 | 6/2015 |
| WO | 2016090270 A1 | 6/2016 |
| WO | 2016164824 A1 | 10/2016 |
| WO | 2016187054 A1 | 11/2016 |
| WO | 2017004307 A1 | 1/2017 |
| WO | 2017044884 A1 | 3/2017 |
| WO | 2017106177 A1 | 6/2017 |
| WO | 2017213788 A1 | 12/2017 |
| WO | 2018004834 A1 | 1/2018 |
| WO | 2018064394 A1 | 4/2018 |
| WO | 2018165162 A1 | 9/2018 |
| WO | 2018183393 A1 | 10/2018 |
| WO | 2018183727 A1 | 10/2018 |
| WO | 2018187488 A1 | 10/2018 |
| WO | 2018208994 A1 | 11/2018 |
| WO | 2019005872 A1 | 1/2019 |
| WO | 2019005992 A1 | 1/2019 |
| WO | 2019074669 A1 | 4/2019 |
| WO | 2019113389 A1 | 6/2019 |
| WO | 2019133438 A1 | 7/2019 |
| WO | 2019160865 A1 | 8/2019 |
| WO | 2019169178 A1 | 9/2019 |
| WO | 2019222641 A1 | 11/2019 |
| WO | 2020033318 A1 | 2/2020 |
| WO | 2020061240 A1 | 3/2020 |
| WO | 2020069430 A1 | 4/2020 |
| WO | 2020072747 A1 | 4/2020 |
| WO | 2020092064 A1 | 5/2020 |
| WO | 2020140072 A1 | 7/2020 |
| WO | 2020167749 A1 | 8/2020 |
| WO | 2021011518 A1 | 1/2021 |
| WO | 2021011533 A1 | 1/2021 |
| WO | 2021011551 A1 | 1/2021 |
| WO | 2021011554 A1 | 1/2021 |
| WO | 2021011571 A1 | 1/2021 |

(56) References Cited

FOREIGN PATENT DOCUMENTS

| WO | 2021015990 A1 | 1/2021 |
| WO | 2021028883 A1 | 2/2021 |
| WO | 2021044297 A1 | 3/2021 |
| WO | 2021137071 A1 | 7/2021 |
| WO | 2021137081 A1 | 7/2021 |
| WO | 2021137106 A1 | 7/2021 |

OTHER PUBLICATIONS

International Search Report of appl No. PCTIB2020057707, dated Jan. 13, 2021, 7 pages.
Written opinion for appl No. PCTIB2020057707, dated Jan. 13, 2021, 11 pages.

* cited by examiner

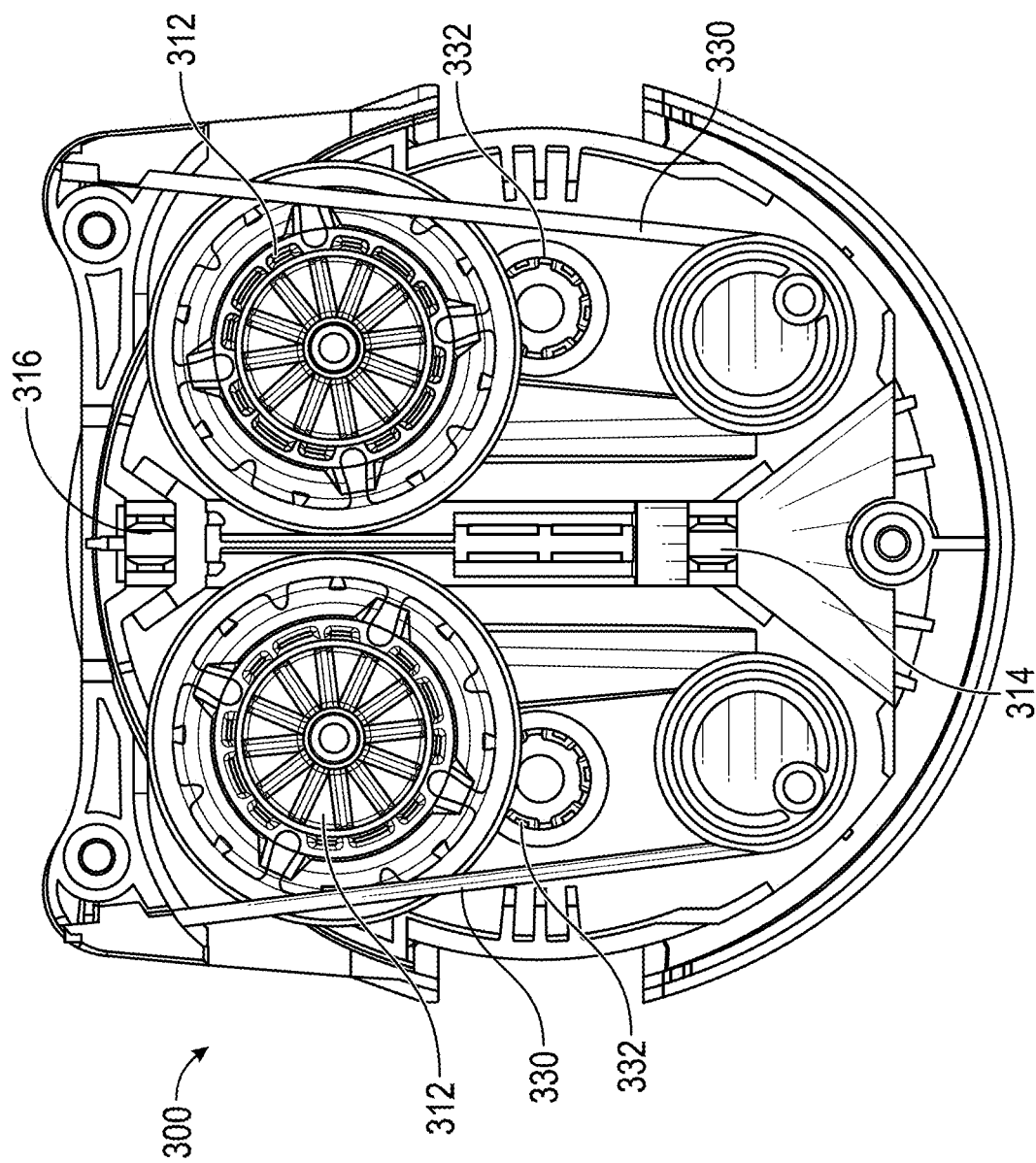

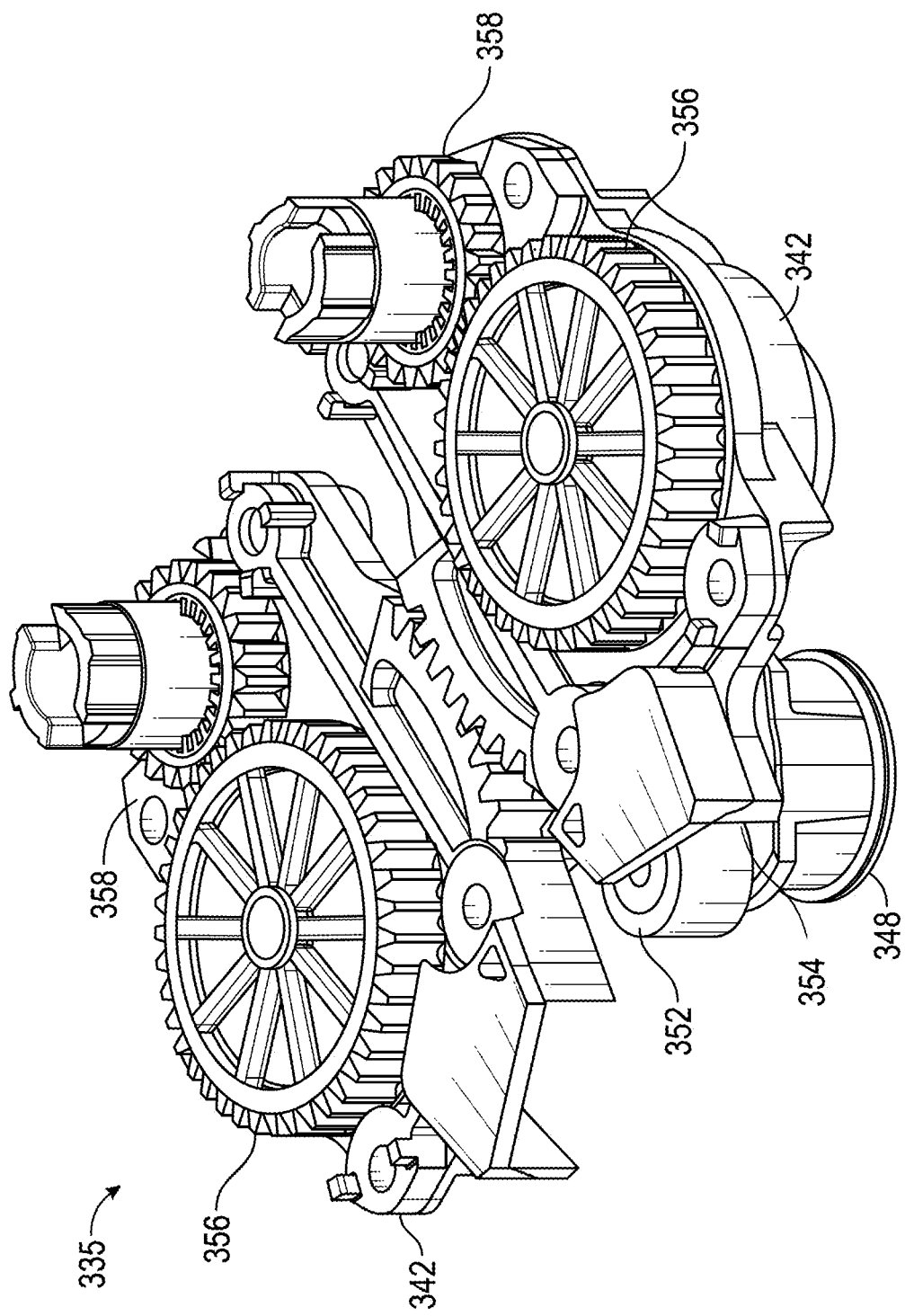

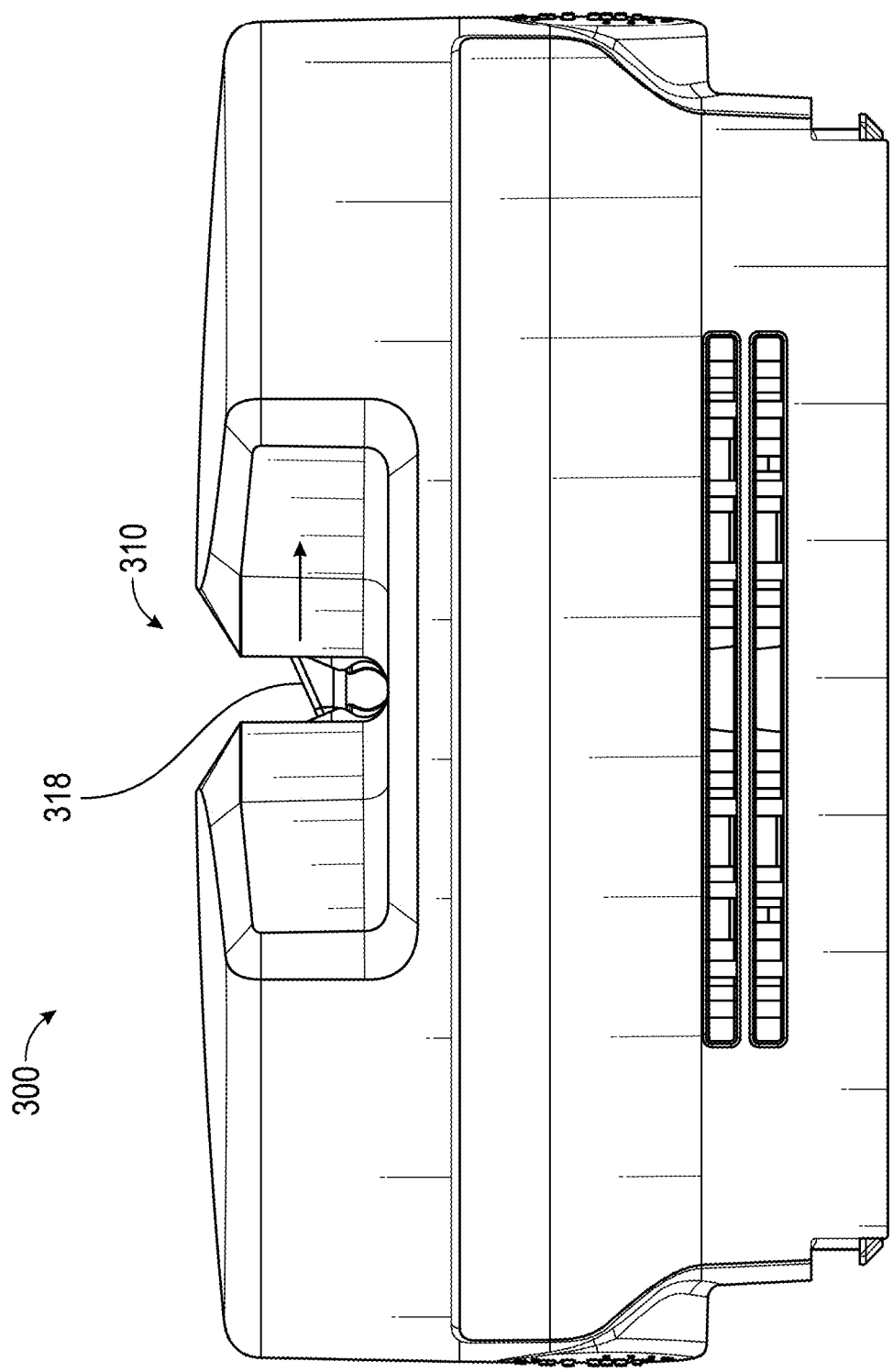

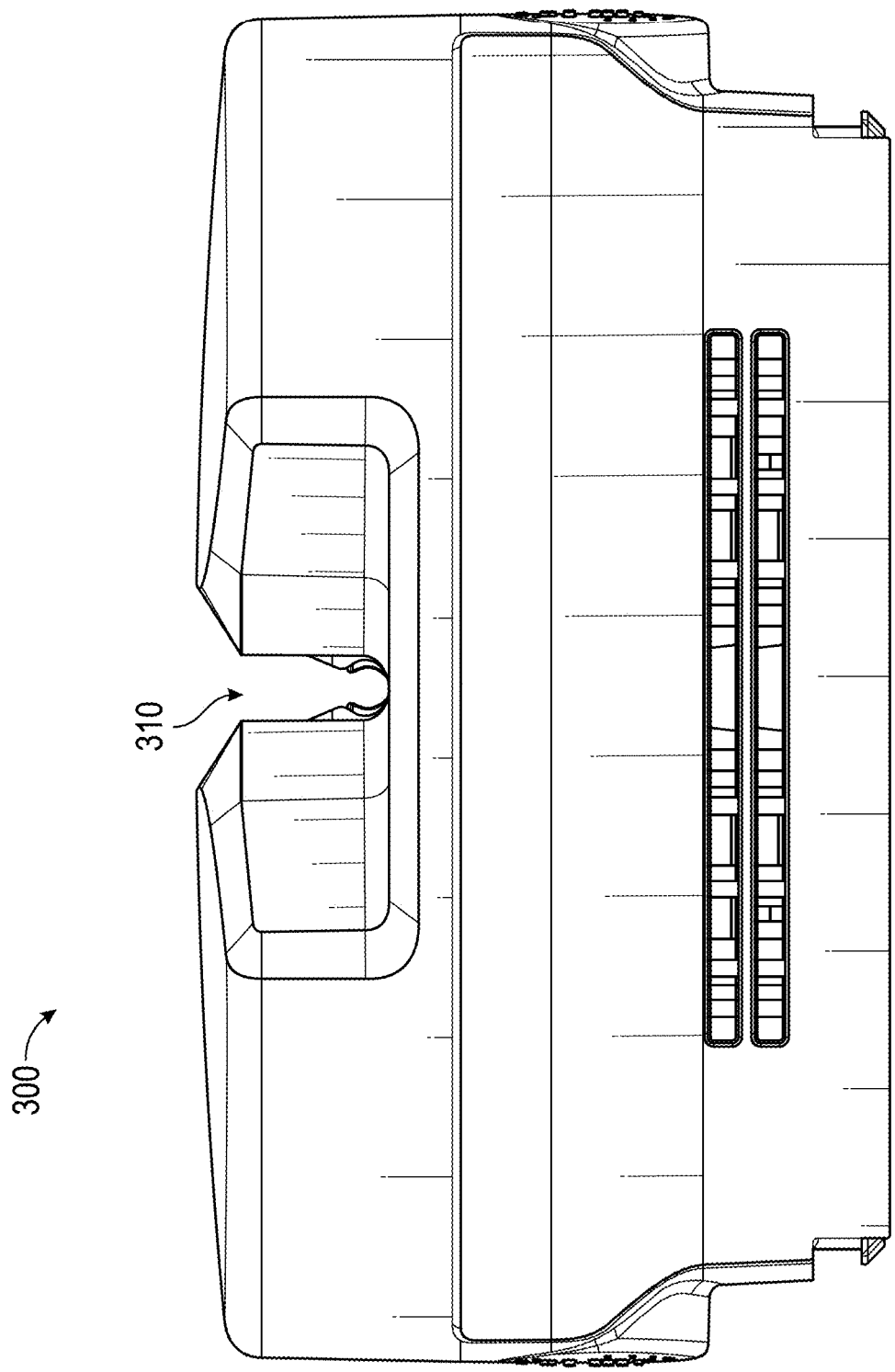

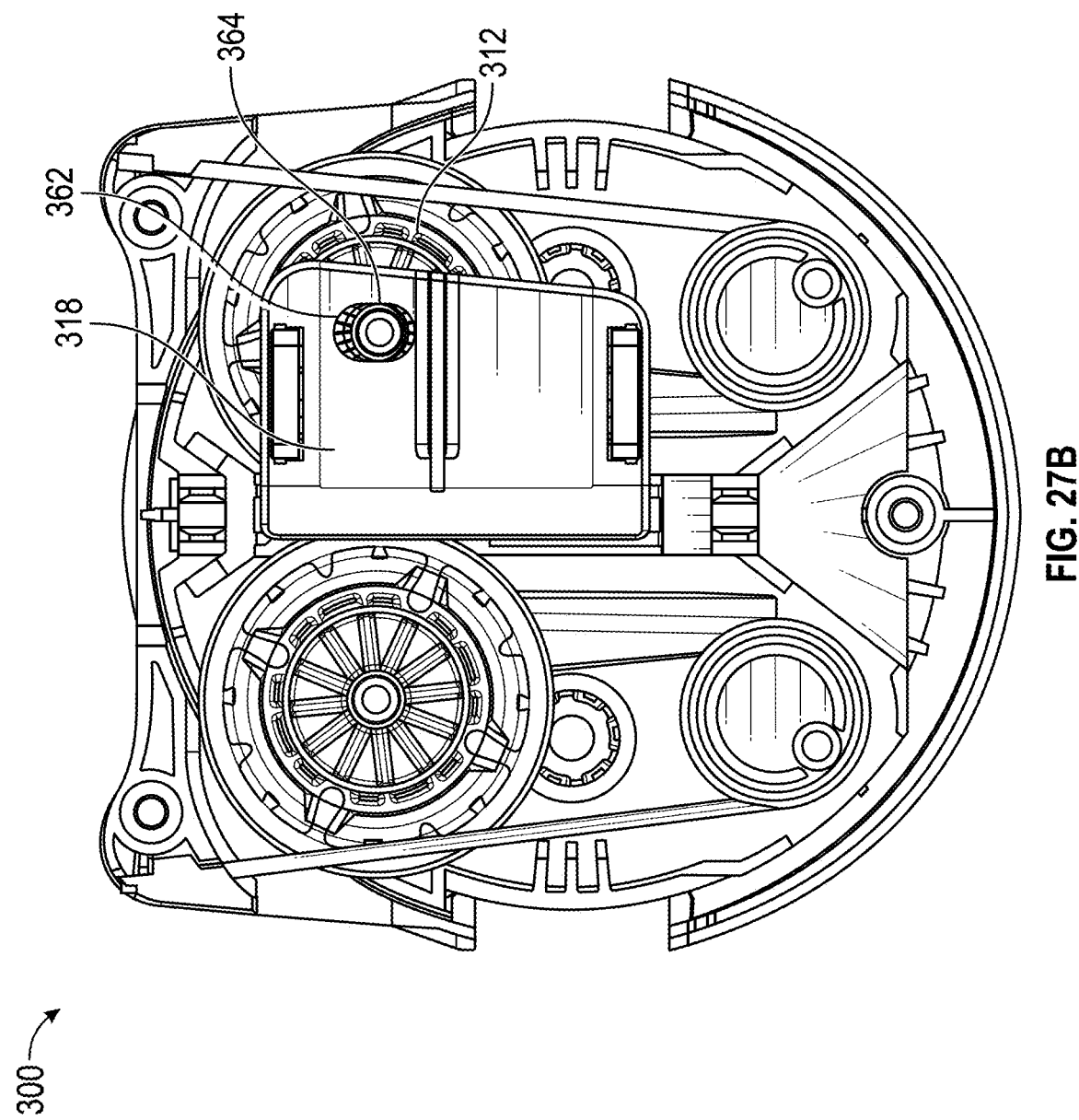

AXIAL MOTION DRIVE DEVICES, SYSTEMS, AND METHODS FOR A ROBOTIC MEDICAL SYSTEM

PRIORITY AND RELATED APPLICATIONS

This application claims priority to U.S. Provisional Pat. App. No. 62/887,518, filed Aug. 15, 2019, which is incorporated herein by reference. Any and all applications for which a foreign or domestic priority claim is identified in the Application Data Sheet as filed with the present application are hereby incorporated by reference under 37 CFR 1.57.

TECHNICAL FIELD

Systems and methods disclosed herein relate to robotic medical systems, and more particularly, to axial motion drive devices and related systems and methods for driving axial motion of elongated shafts of medical instruments in robotic medical systems.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, known as an endoscope, is inserted into the patient through an orifice (such as a natural orifice) and advanced towards a tissue site identified for subsequent diagnosis and/or treatment. The medical instrument can be controllable and articulable to facilitate navigation through the anatomy.

SUMMARY

In a first aspect, a robotic medical system, is disclosed that comprises: a medical instrument comprising an instrument base and an elongated shaft configured for insertion into a patient; a first robotic arm, wherein the instrument base of the medical instrument is attached to the first robotic arm and the first robotic arm is articulable to move the instrument base; a second robotic arm; a drive device attached to the second robotic arm and distal relative to the instrument base, wherein the drive device is engaged with and configured to drive axial motion of the elongated shaft of the medical instrument; and a processor configured to, during a first period of axial motion drive axial motion of the elongated shaft of the medical instrument with the drive device at a first axial motion rate that is greater than a movement rate of the first robotic arm.

The robotic medical system may include one or more of the following features in any combination: (a) wherein, during the first period of axial motion, a portion of the elongated shaft of the medical instrument between the instrument base and the drive device has a length greater than a distance between the instrument base and the drive device such that the portion of the elongated shaft forms a service loop; (b) wherein, during the first period of axial motion, a rate of change of a length of the service loop is greater than a rate of change of the distance between the between the instrument base and the drive device; (c) wherein the axial motion comprises at least one of retraction or insertion of the elongated shaft; (d) wherein the processor is configured to drive axial motion of the elongated shaft at the first axial motion rate when a distal tip of the elongated shaft is positioned within an access sheath; (e) wherein the processor is configured to, during a second period of axial motion, drive axial motion of the elongated shaft of the medical instrument with the drive device at a second axial motion rate that is equal to or less than the movement rate of the first robotic arm; (f) wherein, during the second period of axial motion, a portion of the elongated shaft of the medical instrument between the instrument base and the drive device has a length substantially equal to a distance between the instrument base and the drive device such that the portion of the elongated shaft does not form a service loop; (g) wherein, during the second period of axial motion, a portion of the elongated shaft of the medical instrument between the instrument base and the drive device has a length greater than a distance between the instrument base and the drive device such that the portion of the elongated shaft forms a service loop; (h) wherein, during the second period of axial motion, a rate of change of the length is equal to or less than a rate of change of the distance between the between the instrument base and the drive device; (i) wherein the processor is configured to drive axial motion of the elongated shaft at the second axial motion rate when a distal tip of the elongated shaft is positioned beyond an access sheath; (j) wherein the drive device is configured to attach to an access sheath configured to be inserted into the patient, and the elongated shaft is configured to be inserted into the patient through the access sheath; (k) wherein the drive device comprises a clip configured to attach to a proximal end of the access sheath; (l) wherein the drive device is configured to withdraw a distal tip of the elongated shaft from a proximal end of the access sheath, and reinsert the distal tip of the elongated shaft into the proximal end of the access sheath; (m) an instrument driver comprising a plurality of drive outputs positioned at a distal end of the second robotic arm, wherein the drive device comprises a plurality of drive inputs configured to engage the plurality of drive outputs of the instrument driver; (n) a sterile adapter positioned between the instrument driver and the drive device; (o) wherein the drive device comprises a pair of opposing rollers configured to drive axial motion of the elongated shaft; (p) wherein the drive device comprises a body comprising a channel configured to receive the elongated shaft of the medical instrument, a roller configured to engage with the elongated shaft, wherein the second robotic arm is configured to rotate the roller to drive axial motion of the elongated shaft received in the channel, and a pivotable carrier supporting the roller, wherein the second robotic arm is configured to pivot the carrier to selectively engage or disengage the roller with the elongated shaft; (q) wherein, based on receiving a roll command to roll the elongated shaft, the processor is configured to cause the first robotic arm to rotate the elongated shaft about a longitudinal axis of the elongated shaft, and the second robotic arm to disengage the drive device from the elongated shaft; and/or other features as described throughout this application.

In another aspect, a robotic medical system is disclosed that comprises: a medical instrument comprising an instrument base and a flexible shaft configured for insertion into a patient; a first robotic arm attachable to the instrument base of the medical instrument; a drive device configured to engage the flexible shaft; and a second robotic arm attachable to the drive device, wherein the second robotic arm is configured to operate the drive device to drive axial motion of the flexible shaft, and wherein the first robotic arm is configured to move in coordination with operation of the drive device.

The robotic medical system may include one or more of the following features in any combination: (a) wherein the second robotic arm is configured to disengage the drive device from the flexible shaft while retaining the flexible shaft in the drive device with a robotically-actuated cover; (b) wherein the second robotic arm is configured to control a rate of the axial motion based on a position of a tip of the flexible shaft relative to an access sheath; (c) wherein the second robotic arm is configured to expand or contract a service loop in a portion of the flexible shaft between the first and second robotic arms; (d) wherein the medical instrument is an endoscope; and/or other features as described throughout this application.

In another aspect, a robotic medical system is disclosed that comprises: a first robotic arm configured to support an instrument base of a medical instrument, the medical instrument comprising an elongated shaft extending from the instrument base; and a second robotic arm configured to operate one or more rollers engageable with the elongated shaft to drive axial motion of the elongated shaft.

The robotic medical system may include one or more of the following features in any combination: (a) wherein the one or more rollers comprise a pair of opposing rollers of a drive device attached to the second robotic arm and configured to drive axial motion of the flexible shaft; (b) wherein the second robotic arm is configured to disengage the drive device from the flexible shaft and retain the flexible shaft in the drive device with a robotically-actuated cover; and/or other features as described throughout this application.

In another aspect, a method is disclosed that comprises: supporting, with a first robotic arm, an instrument base of a medical instrument; driving, with a second robotic arm, axial motion of an elongated shaft of the medical instrument; and moving the first robotic arm in concert with driving the axial motion.

The method may include one or more of the following features in any combination: (a) wherein driving the axial motion comprises operating a pair of opposing rollers with the second robotic arm; (b) wherein the first robotic arm moves at a rate slower than the axial motion of the elongated shaft; (c) wherein the second robotic arm is configured to disengage a drive device from the elongated shaft while retaining the elongated shaft in the drive device with a robotically-actuated cover; and/or other features as described throughout this application.

In another aspect, a drive device configured to facilitate axial motion of an elongated shaft of a medical instrument is disclosed that comprises: a housing comprising a lower surface configured to mount to a robotic arm and an upper surface with a channel formed therein, the channel configured to receive the elongated shaft of the medical instrument; a first roller positioned within the housing on a first side relative to the channel; and a second roller positioned within the housing on a second side relative to the channel; wherein the first and second rollers are movable between a first position and a second position; wherein, in the first position, the first and second rollers are configured to engage with the elongated shaft such that when rotated in a first direction, the first and second rollers drive insertion of the elongated shaft, and when rotated in a second direction, the first and second rollers drive retraction of the elongated shaft; and wherein, in the second position, the first and second rollers are spaced apart from the elongated shaft.

The drive may include one or more of the following features in any combination: (a) a proximal clip positioned at a proximal end of the channel; (b) a distal clip positioned at a distal end of the channel; (c) wherein the proximal and distal clips are configured to retain the elongated shaft within the channel; (d) a cover, wherein the cover is operable to close the channel when the first and second rollers are in the first position and to open the channel when the first and second rollers are in the second position; (e) wherein movement of the cover is mechanically linked to movement of one of the first roller and the second roller such that the cover opens and closes as the first and second rollers move between the second and first positions; (f) wherein, at an intermediate position between the first and the second positions, the cover remains closed and the first and second rollers disengage from the elongated shaft; (g) a collector distal to the channel for depositing objects retrieved from within the patient using the medical instrument; (h) a clip configured to support a proximal end of an access sheath; (i) a space for depositing objects retrieved from within the patient using the medical instrument between the clip and the channel; (j) a first spring positioned within the housing and configured to bias the first roller toward the first position, and a second spring positioned within the housing and configured to bias the second roller towards the first position; (k) wherein the first and second springs comprise torsion springs; (l) a first carrier plate positioned within the housing and configured to rotate about a first axis, wherein the first roller is mounted to the first carrier plate and rotation of the first carrier plate moves the first roller between the first position and the second position, and a second carrier plate positioned within the housing and configured to rotate about a second axis, wherein the second roller is mounted to the second carrier plate and rotation of the second carrier plate moves the second roller between the first position and the second position; (m) a first roller drive input positioned on the lower surface of the housing, a first gear mounted on the first carrier plate and driven by the first roller drive input, a first orbital gear mounted on the first carrier plate and driven by the first gear, wherein rotation of the first orbital gear drives rotation of the first roller, a second roller drive input positioned on the lower surface of the housing, a second gear mounted on the second carrier plate and driven by the second roller drive input, and a second orbital gear mounted on the second carrier plate and driven by the second gear, wherein rotation of the second orbital gear drives rotation of the second roller; (n) wherein the first axis about which the first carrier plate rotates is coaxial with an axis of the first roller input, and the second axis about which the second carrier plate rotates is coaxial with an axis of the second roller input; (o) wherein the first carrier plate and the second carrier plate are geared together such that rotation of one of the first carrier plate and the second carrier plate causes rotation of the other of the first carrier plate and the second carrier plate; (p) a carrier plate rotation drive input configured to rotate one of the first carrier plate or the second carrier plate; (q) an off-axis protrusion coupled to the rotation drive input and configured to contact a pocket of the carrier plate to cause rotation of the first carrier plate; and/or other features as described through this application.

In another aspect, a drive device configured to facilitate axial motion of an elongated shaft of a medical instrument is disclosed that comprises: a body comprising a channel configured to receive the elongated shaft of the medical instrument; a roller configured to engage with the elongated shaft such that, when rotated, the roller drives axial motion of the elongated shaft received in the channel; a first drive input coupled to the body, wherein the first drive input is operable by a robotic system to rotate the roller; a cover configured to selectively open or close the channel; and a second drive input coupled to the body, wherein the second drive input is operable to actuate the cover.

The drive device may include one or more of the following features in any combination: (a) wherein the second drive input is operable to actuate the cover between a first position, where the cover retains the elongated shaft in the channel, and a second position, where the cover permits loading or unloading of the elongated shaft in the channel; (b) a carrier supporting the roller, wherein the carrier is pivotable by a drive input coupled to the body to engage or disengage the elongated shaft received in the channel; (c) wherein the body is configured to attach to an access sheath to align the channel to the access sheath; (d) wherein the second drive input is operatively coupled to the cover via a cam; (e) one or more clips in the channel; (f) wherein the roller is a first roller, and the drive device further comprises a second roller opposing the first roller; and/or other features as described throughout this application.

In another aspect, a robotic medical system is disclosed that comprises: a drive device comprising a channel configured to receive an elongated shaft, one or more rollers configured to engage the elongated shaft received in the channel, and a cover configured to selectively close or open the channel; and a driver configured to: actuate the drive device to a first state, where the one or more rollers are disengaged from the elongated shaft and the cover is open; actuate the drive device to a second state, where the one or more rollers are disengaged from the elongated shaft and the cover is closed; and actuate the drive device to a third state, where the one or more rollers are engaged with the elongated shaft and the cover is closed.

The robotic medical system may include one or more of the following features in any combination: (a) wherein the driver is configured to actuate the drive device to the first state based on a command to load or unload the elongated shaft; (b) wherein the driver is configured to actuate the drive device to the second state based on a command to roll the elongated shaft; (c) wherein the driver is arranged at an end of a robotic arm, and wherein the driver is configured to actuate the drive device to the second state based on a command to move the robotic arm; (d) wherein the driver is configured to actuate the drive device in the third state to insert or retract the elongated shaft; (e) wherein the driver is configured to operate a first drive input of the drive device to rotate the rollers against the elongated shaft, and operate a second drive input of the drive device to disengage the rollers from the elongated shaft; and/or other features as described throughout this application.

In another aspect, a method for a robotic medical procedure is disclosed the comprises: driving insertion of an flexible shaft of a medical instrument with a drive device at a first rate during a first insertion period wherein a distal tip of the flexible shaft is positioned within an access sheath inserted into a patient; and transitioning to driving insertion of the flexible shaft of the medical instrument with the drive device at a second rate that is slower than the first rate during a second insertion period when the distal tip of the flexible shaft is positioned beyond a distal tip of the access sheath.

The method system may include one or more of the following features in any combination: (a) wherein transitioning to driving insertion of the flexible shaft of the medical instrument with the drive device at the second rate comprises automatically detecting when the distal tip of the flexible shaft is positioned beyond a distal tip of the access; (b) driving retraction of the flexible shaft of the medical instrument with the drive device at a third rate during a first retraction period wherein the distal tip of the flexible shaft is positioned beyond the distal tip of the access sheath, and automatically transitioning to driving retraction of the flexible shaft of the medical instrument with the drive device at a fourth rate that is faster than the third rate during a second retraction period when the distal tip of the flexible shaft is positioned within the access sheath; (c) wherein automatically transitioning to driving retraction of the flexible shaft of the medical instrument with the drive device at the fourth rate comprises detecting when the distal tip of the flexible shaft is positioned within the access sheath; (d) mounting an instrument base of the medical instrument on a first robotic arm, mounting the drive device on a second robotic arm, and engaging the flexible shaft of the medical instrument with the drive device; (e) wherein engaging the flexible shaft of the medical instrument with the drive device comprises engaging opposing rollers of the drive device with the flexible shaft; (f) wherein engaging the flexible shaft of the medical instrument with the drive device further comprises inserting the flexible shaft into a channel on an upper surface of the drive device; (g) moving the instrument base towards the drive device with the first robotic arm during insertion, and moving the instrument base away from the drive device with the first robotic arm during retraction; and/or other features as described throughout this application.

In another aspect. a robotic medical system is disclosed that comprises: a drive device comprising a pair of rollers configured to engage a shaft of a medical instrument; a processor configured to: operate the rollers to drive insertion of the shaft at a first rate during a first insertion period when a distal tip of the shaft is positioned within an access sheath inserted into the patient; and operate the rollers to transition to driving insertion of the shaft at a second rate that is slower than the first rate during a second insertion period when the distal tip of the shaft is positioned beyond a distal tip of the access sheath.

The robotic medical system may include one or more of the following features in any combination: (a) wherein the processor is configured to detect when the distal tip of the shaft is positioned beyond a distal tip of the access sheath based on geometric information associated with the access sheath and the shaft; (b) wherein the processor is configured to detect when the distal tip of the shaft is positioned beyond a distal tip of the access sheath based on image information obtained with the medical instrument; (c) wherein the processor is further configured to operate the rollers to drive retraction of the shaft of the medical instrument at a third rate during a first retraction period when the distal tip of the shaft is positioned beyond the distal tip of the access sheath, and operate the rollers to transition to driving retraction of the shaft of the medical instrument at a fourth rate that is faster than the third rate during a second retraction period when the distal tip of the shaft is positioned within the access sheath; (d) a first robotic arm configured to support the medical instrument, and a second robotic arm configured to support the drive device; (e) wherein the first robotic arm is configured to move an instrument handle of the medical instrument towards the drive device during insertion, and the first robotic arm is configured to move the instrument handle away from the drive device during retraction; and/or other features as described throughout this application.

In another aspect, a robotic medical system is disclosed that comprises: an elongated flexible access sheath; a medical instrument comprising an elongated flexible shaft; and a processor configured to: drive insertion of the shaft at a first rate during a first insertion period when a distal tip of the shaft is positioned within the access sheath; and transition to driving insertion of the shaft at a second rate that is slower than the first rate during a second insertion period when the distal tip of the shaft is positioned beyond a distal tip of the access sheath.

The robotic medical system may include one or more of the following features in any combination: (a) wherein the processor is configured to detect when the distal tip of the shaft is positioned beyond a distal tip of the access sheath based on geometric information associated with the access sheath and the shaft; (b) wherein the processor is configured to detect when the distal tip of the shaft is positioned beyond a distal tip of the access sheath based on image information obtained with the medical instrument; (c) wherein the processor is further configured to drive retraction of the shaft of the medical instrument at a third rate during a first retraction period when the distal tip of the shaft is positioned beyond the distal tip of the access sheath, and transition to driving retraction of the shaft of the medical instrument at a fourth rate that is faster than the third rate during a second retraction period when the distal tip of the shaft is positioned within the access sheath; (d) wherein the processor is configured to operate a drive device to drive axial motion of the elongated flexible shaft, move an instrument handle of the medical instrument towards the drive device during insertion, and move the instrument handle away from the drive device during retraction; and/or other features as described throughout this application.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 24B is a top view of the drive device of FIG. 24A.

FIG. 25B is an isometric view of the roller assembly of FIG. 25A with the rollers removed to illustrate an embodiment of a gearing arrangement of the roller assembly.

FIG. 26B is a rear view of the drive device of FIG. 26A with the instrument shaft cover in the closed configuration.

FIG. 26D is a rear view of the drive device of FIG. 26C, with the instrument shaft cover in the open configuration.

FIG. 27B is a top view of the drive device of FIG. 27A illustrating the instrument shaft cover according to an embodiment.

FIGS. 30A and 30B illustrate an example method of controlling a drive device in various states of operation, wherein FIG. 30A is a flow chart depicting the method, and FIG. 30B illustrates a cross section of the drive device at the various states.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
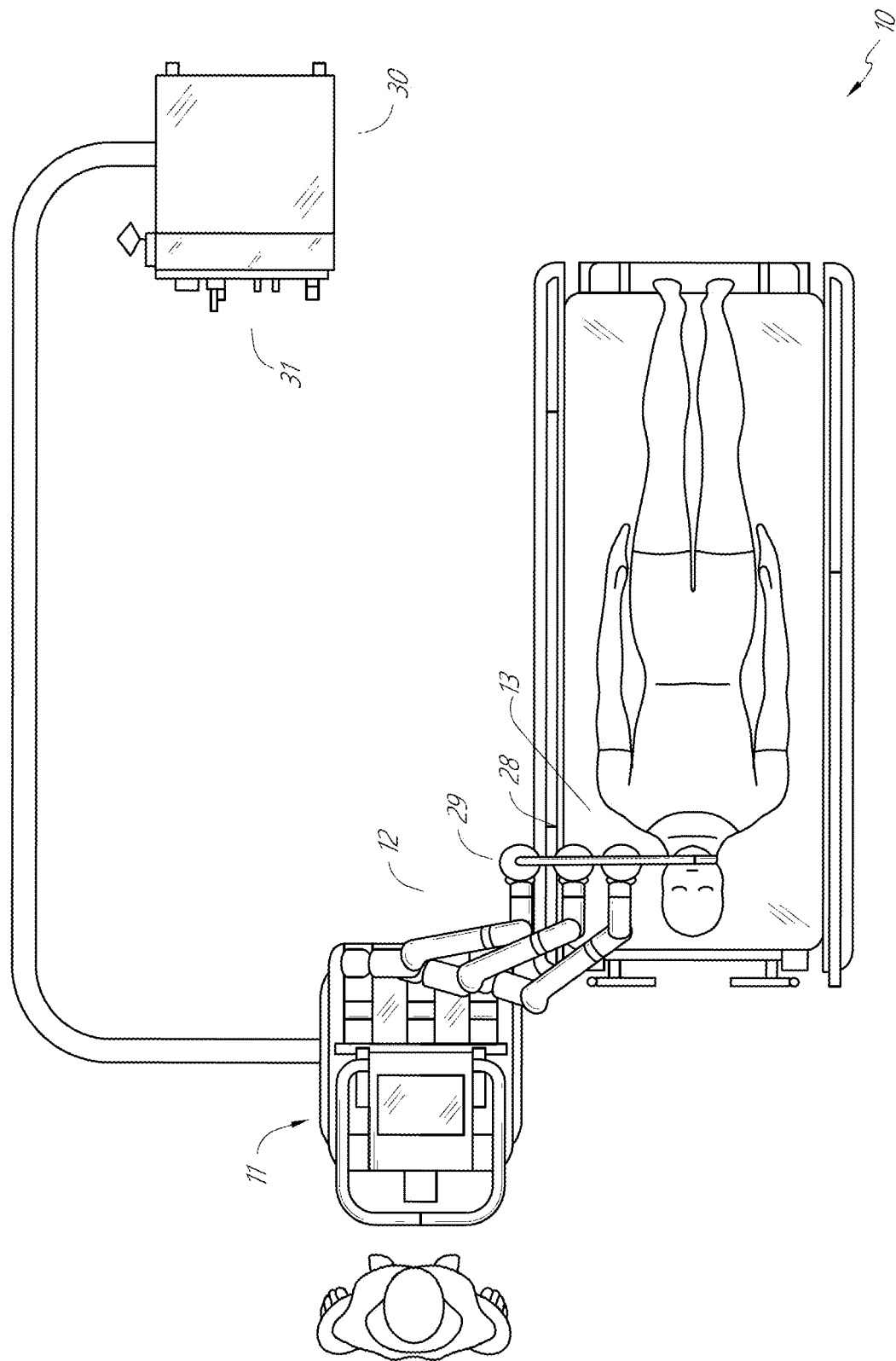
FIG. 1 illustrates an embodiment of a cart-based robotic system arranged for diagnostic and/or therapeutic bronchoscopy.
Figure 2:
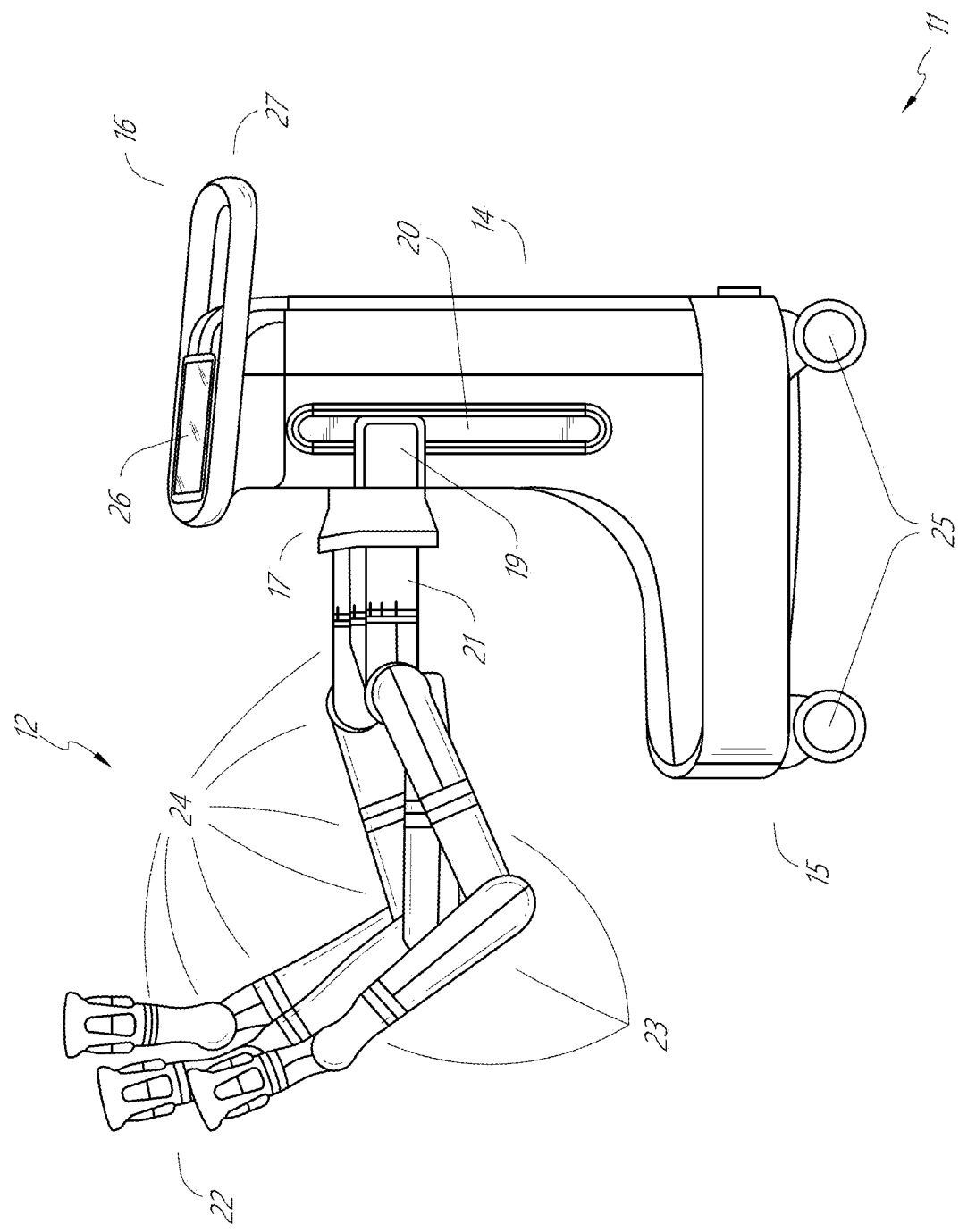
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
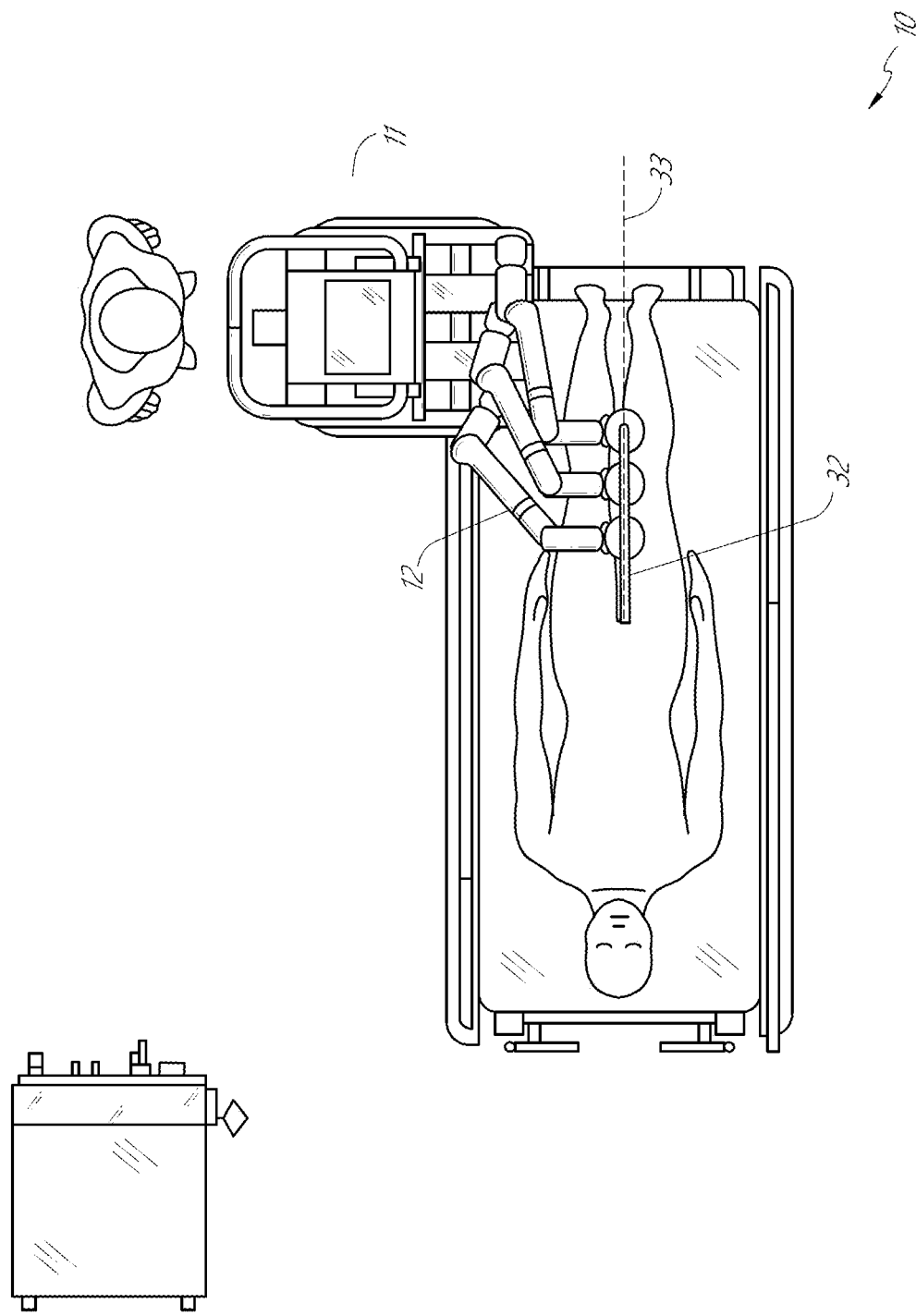
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
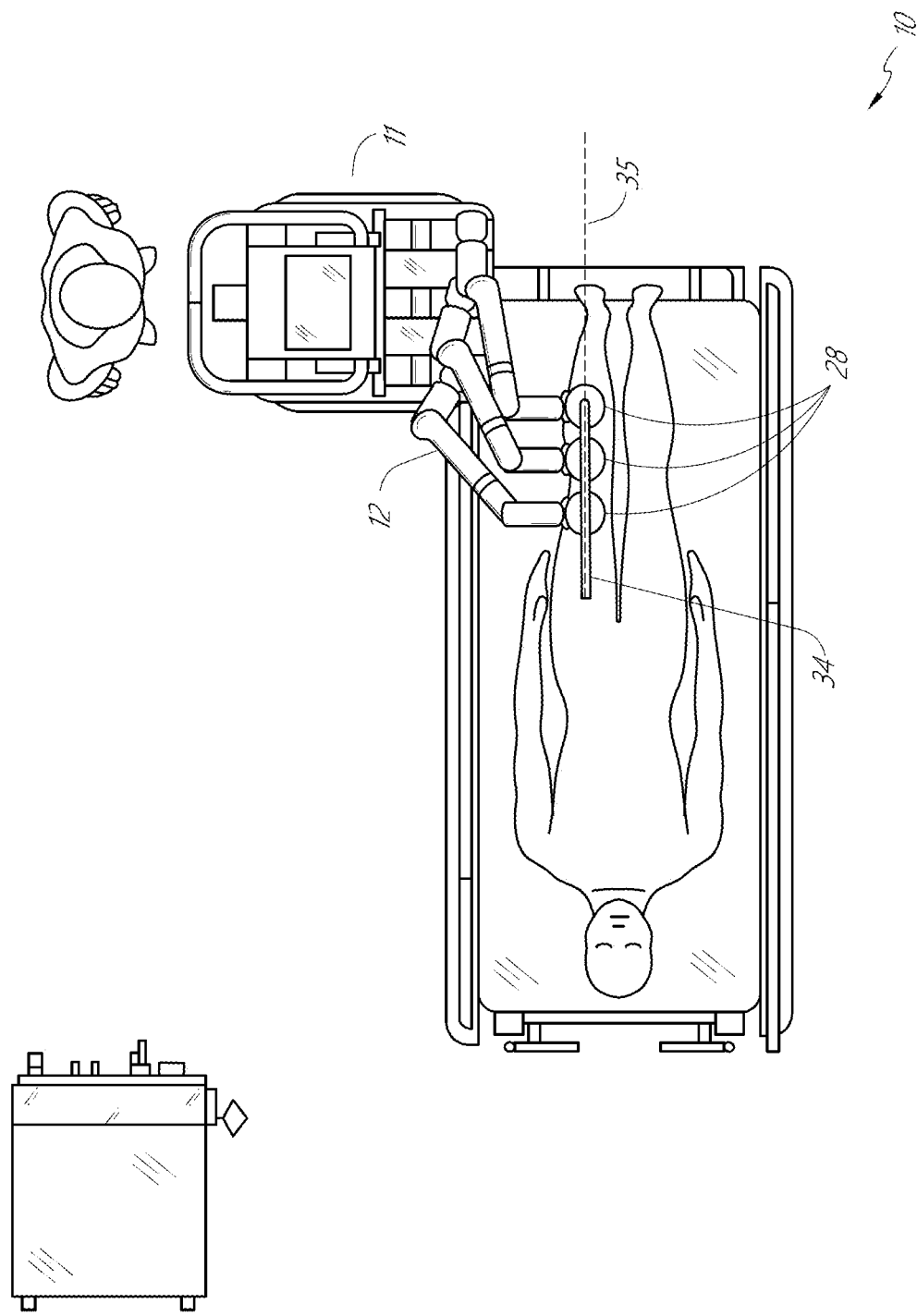
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
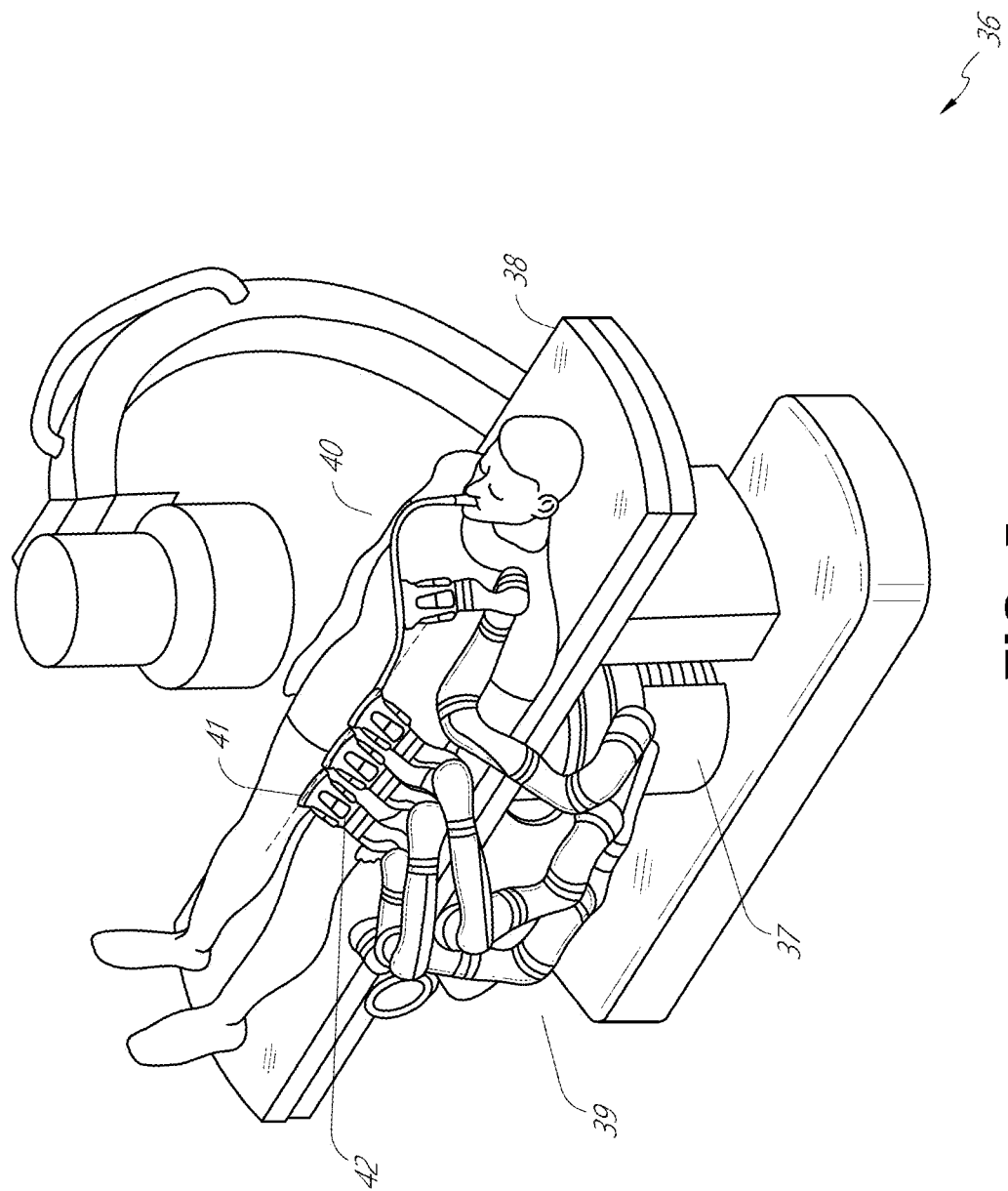
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
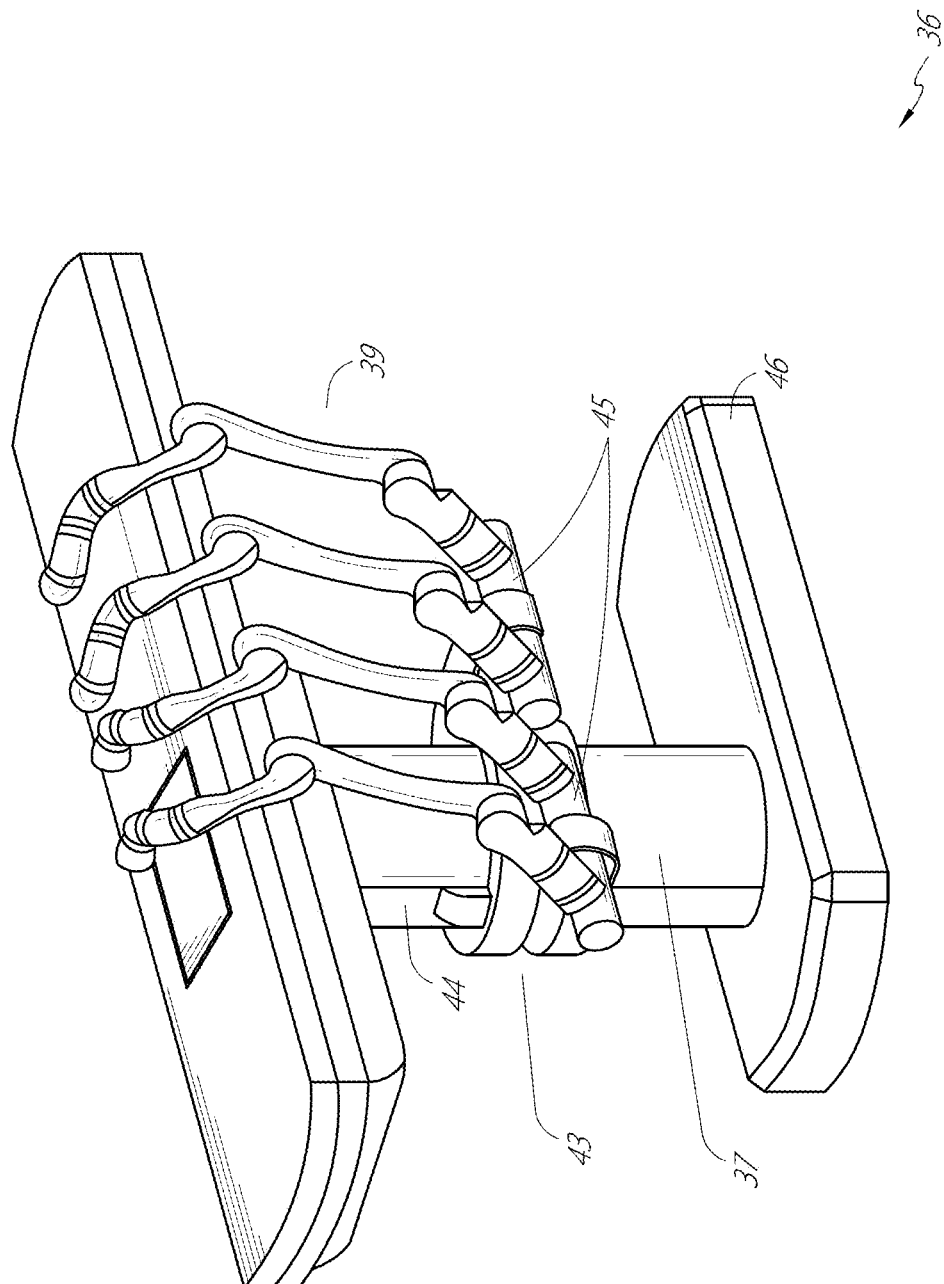
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
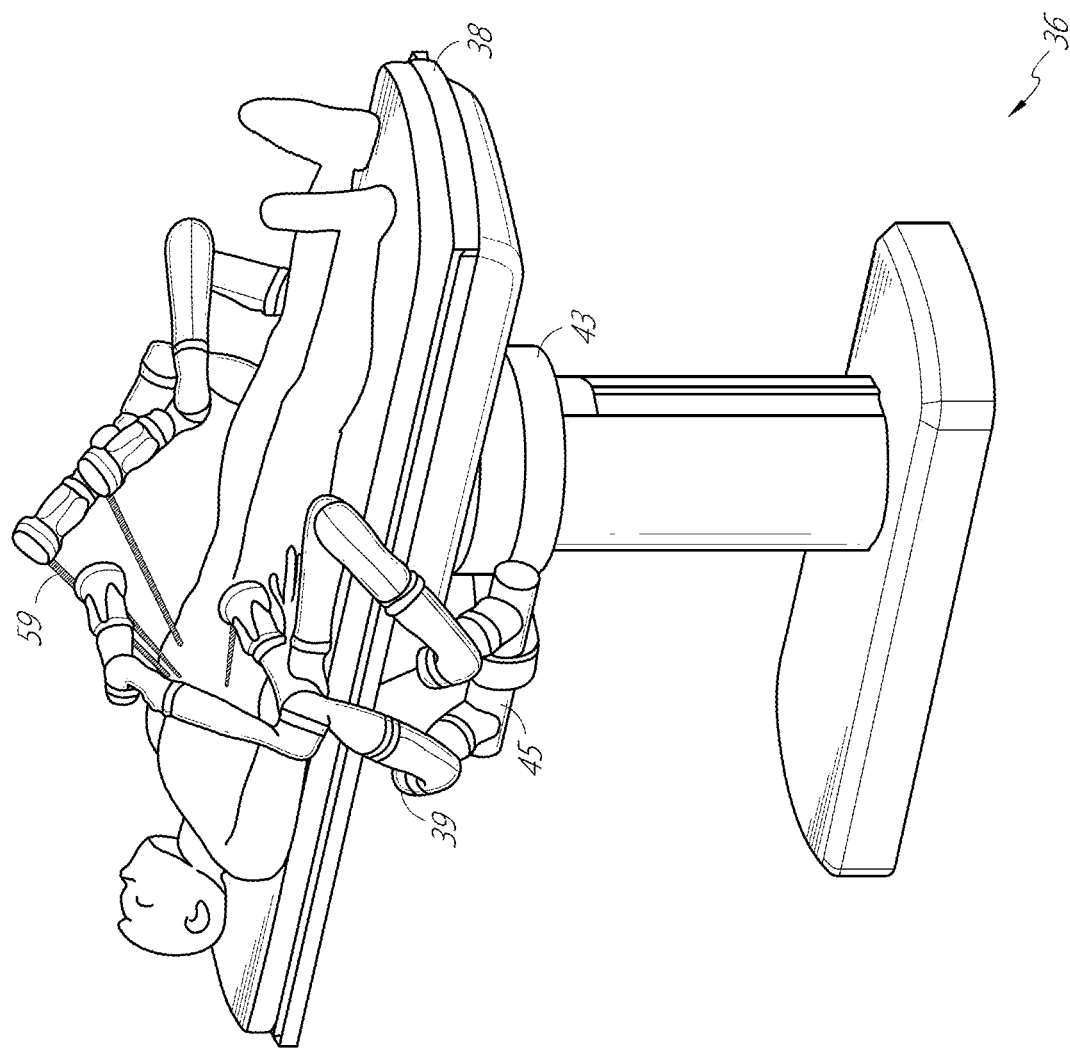
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
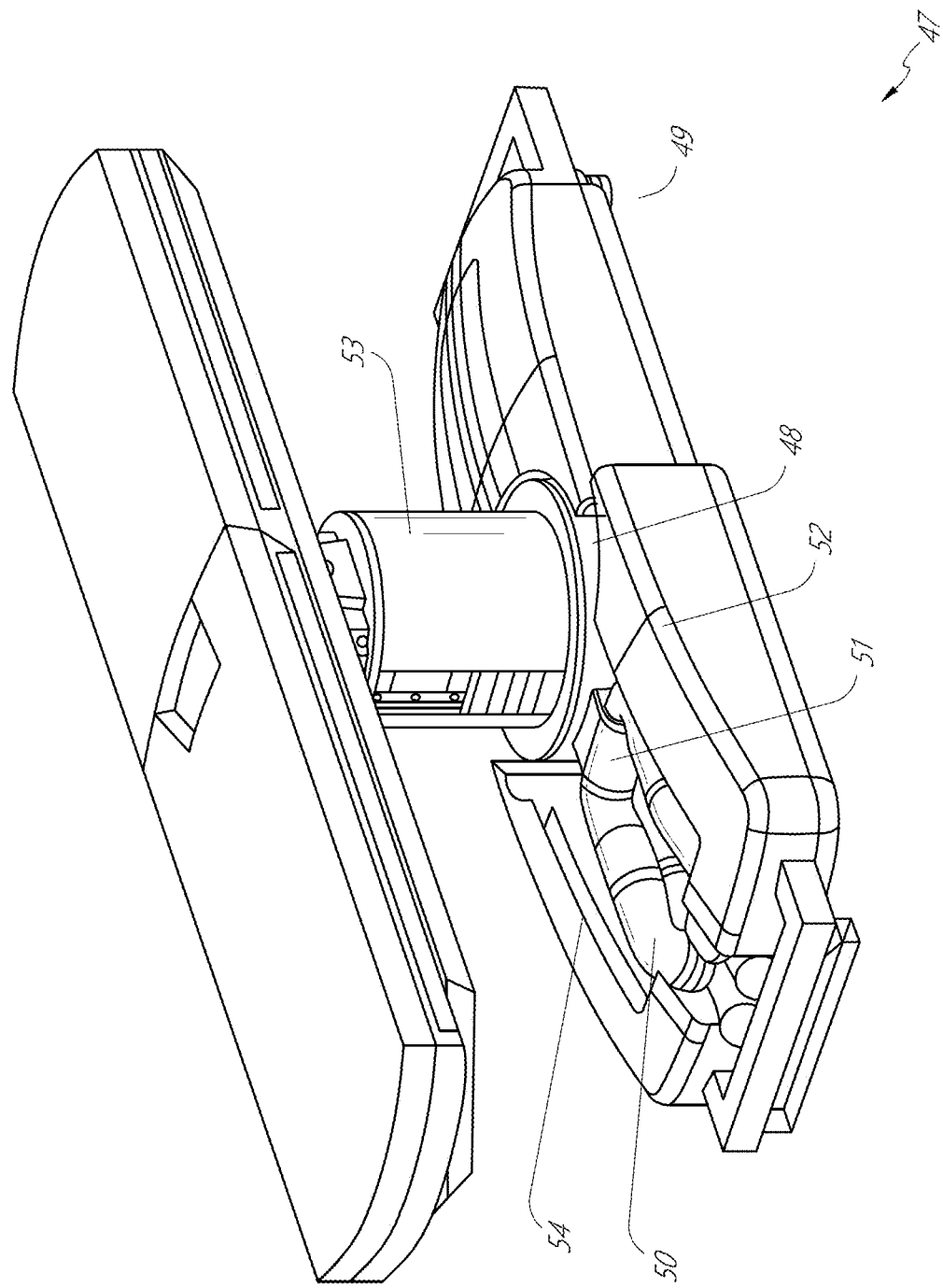
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
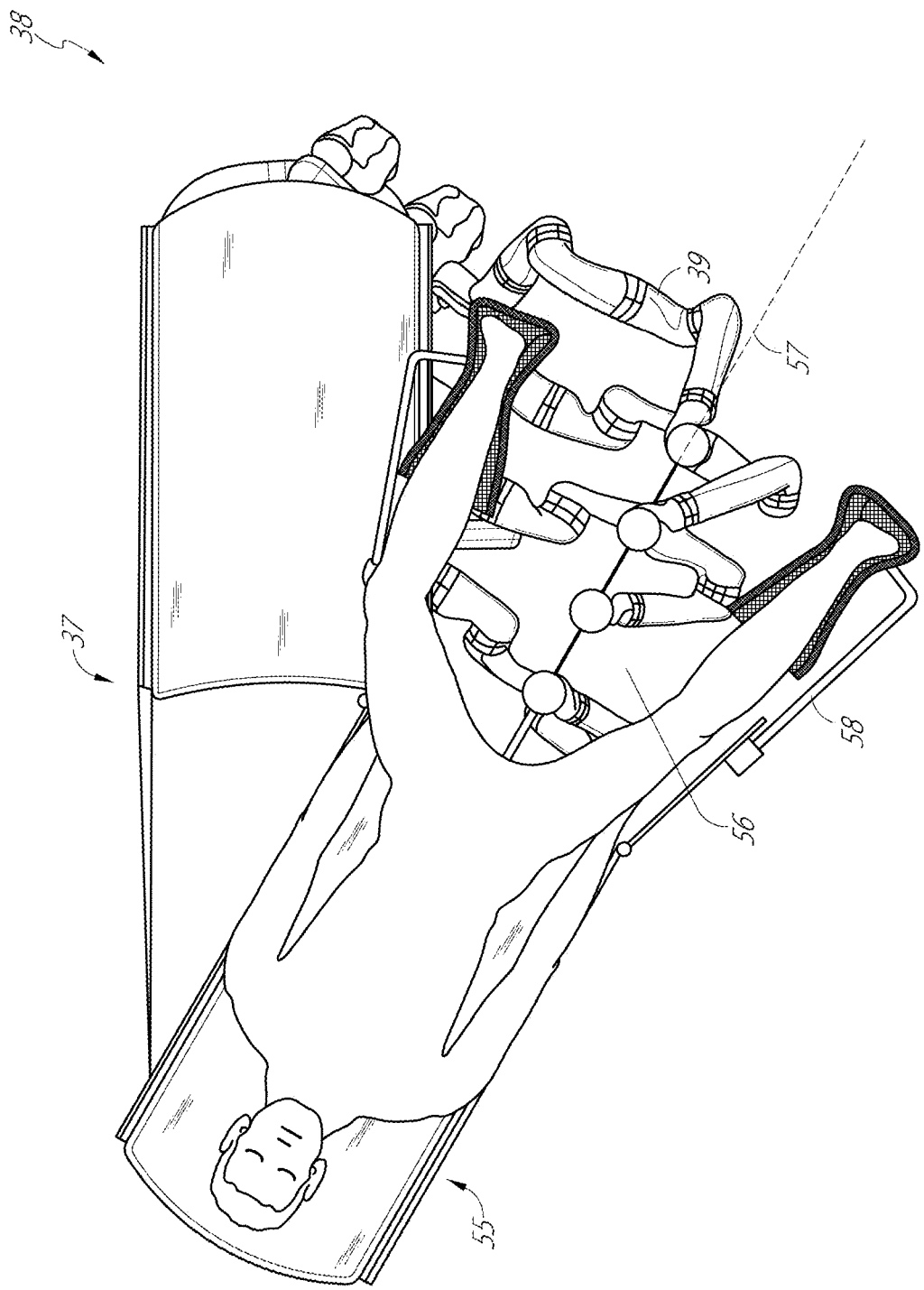
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
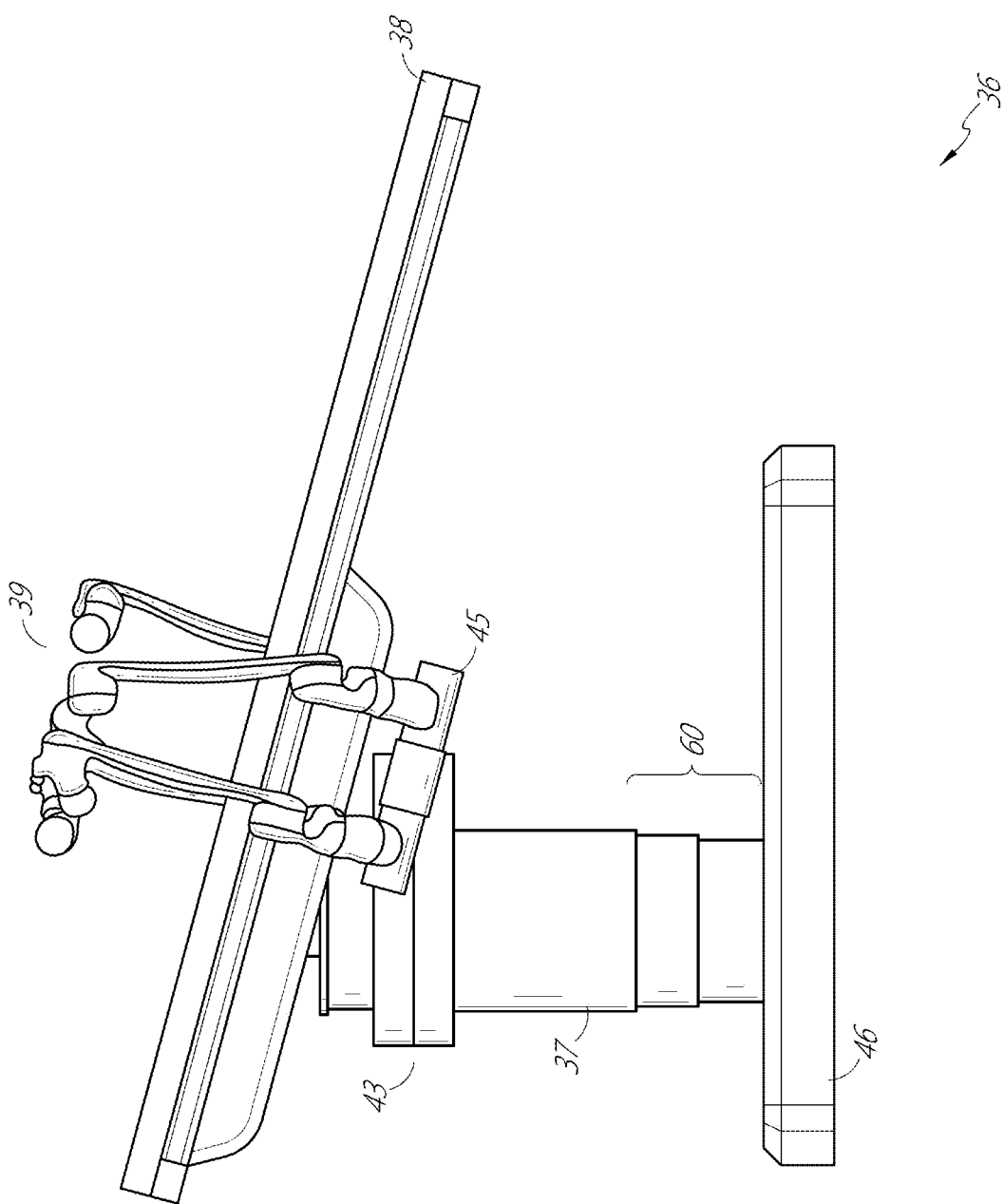
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
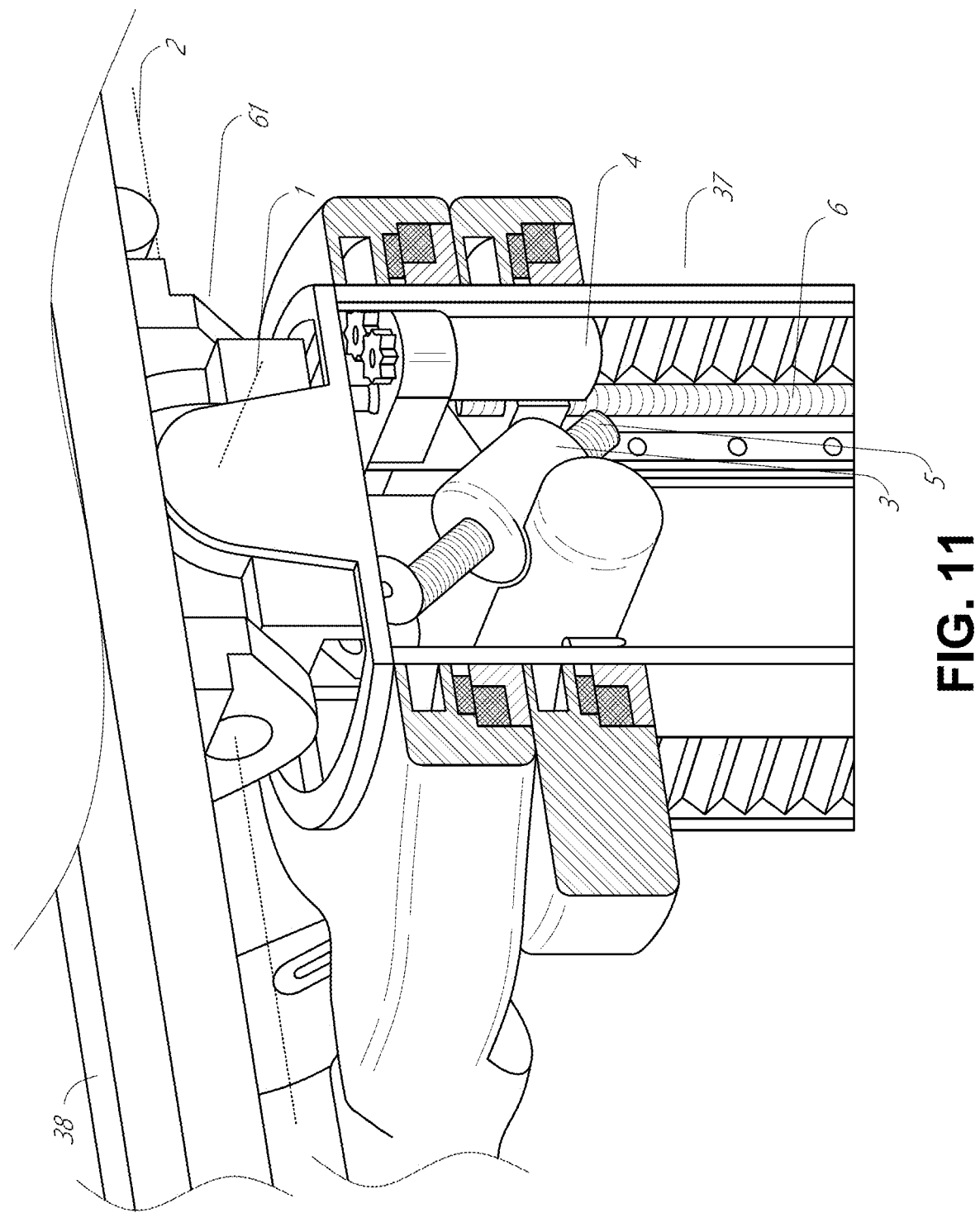
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
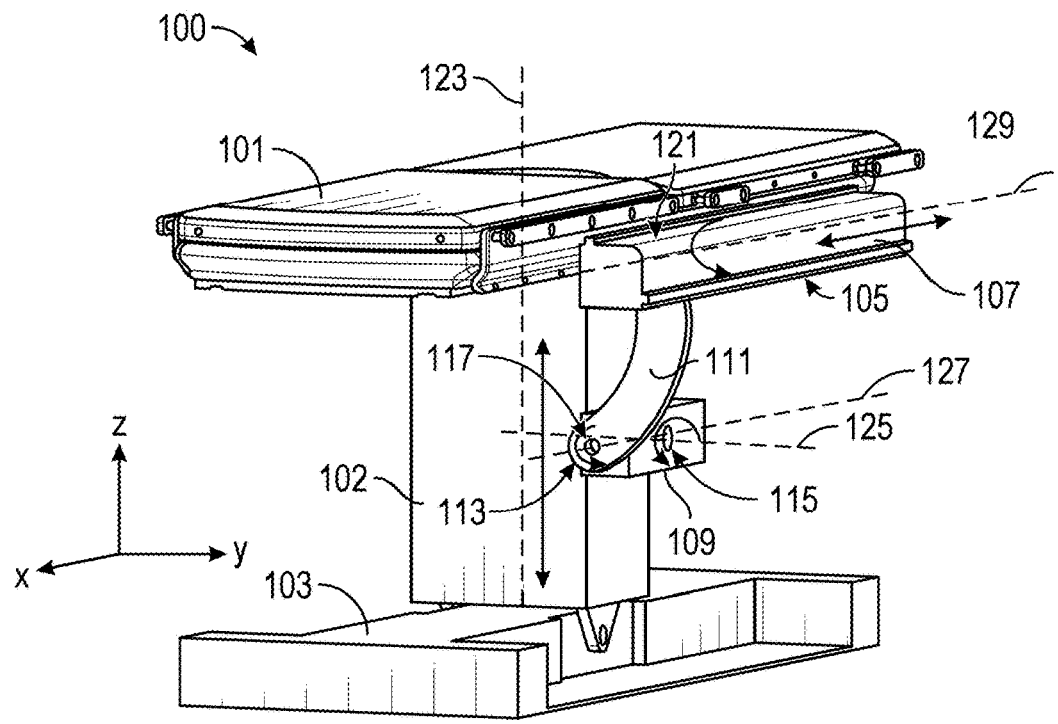
FIG. 12 illustrates an alternative embodiment of a table-based robotic system.
Figure 13:
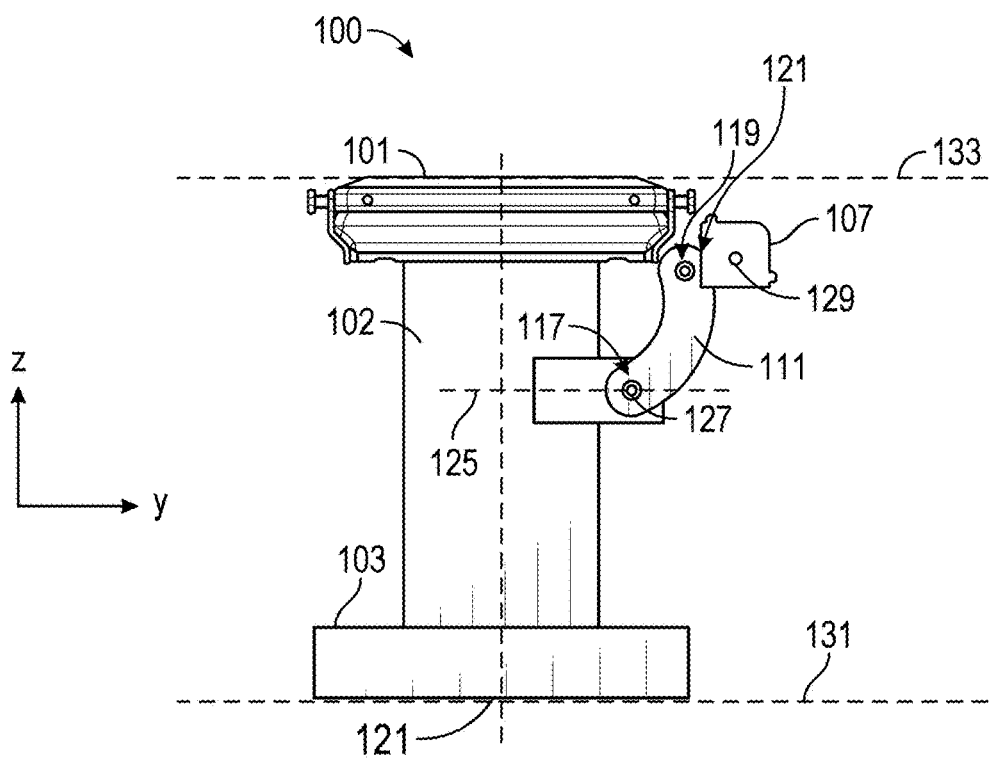
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support 105 can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
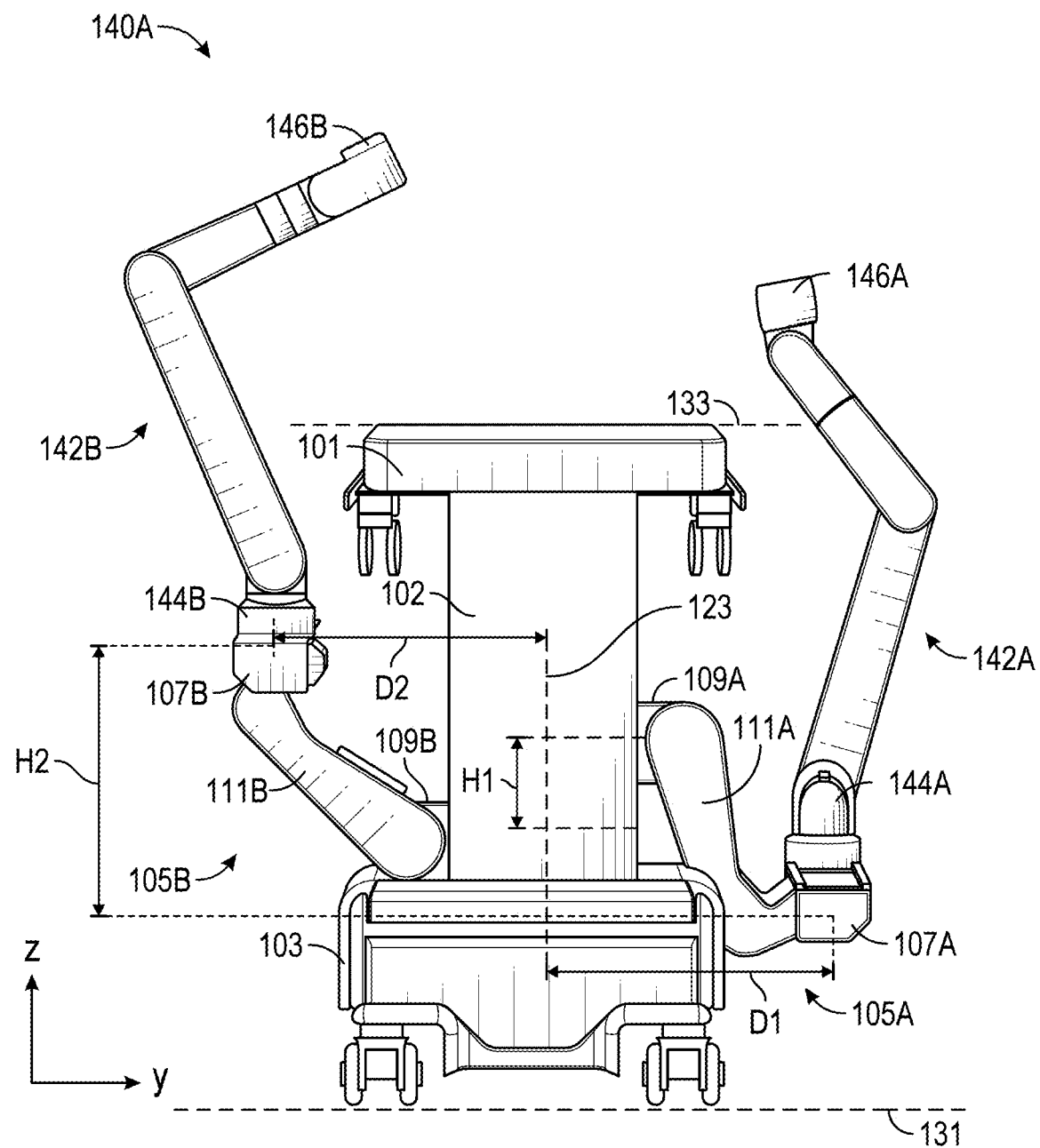
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
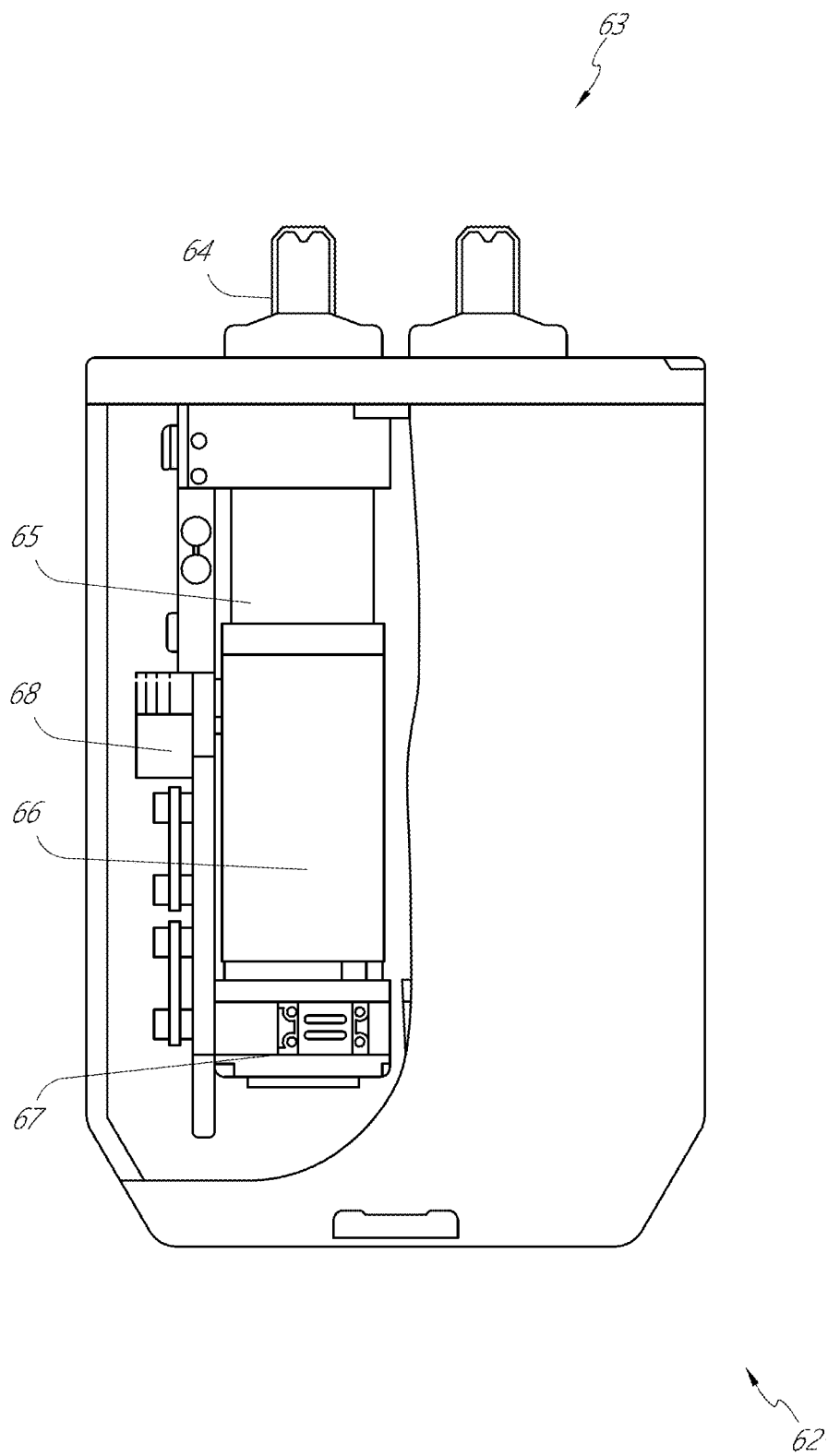
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
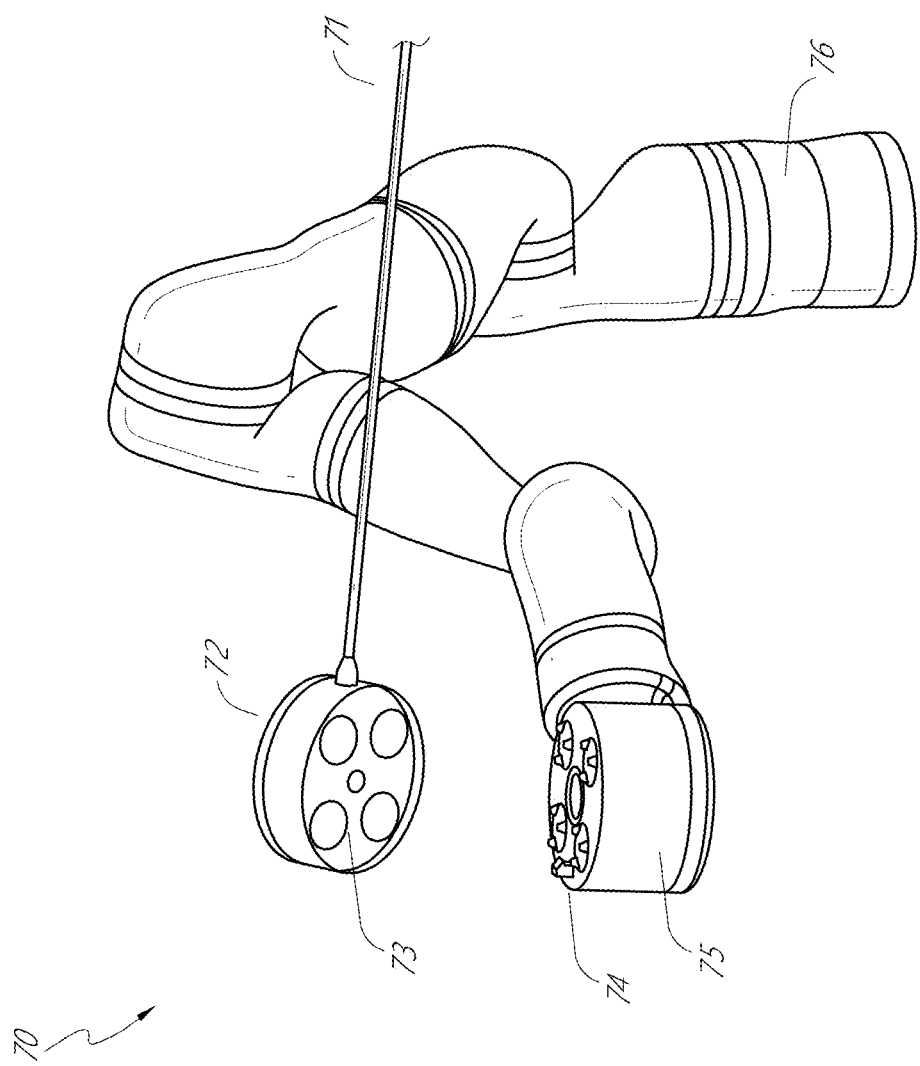
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the instrument handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
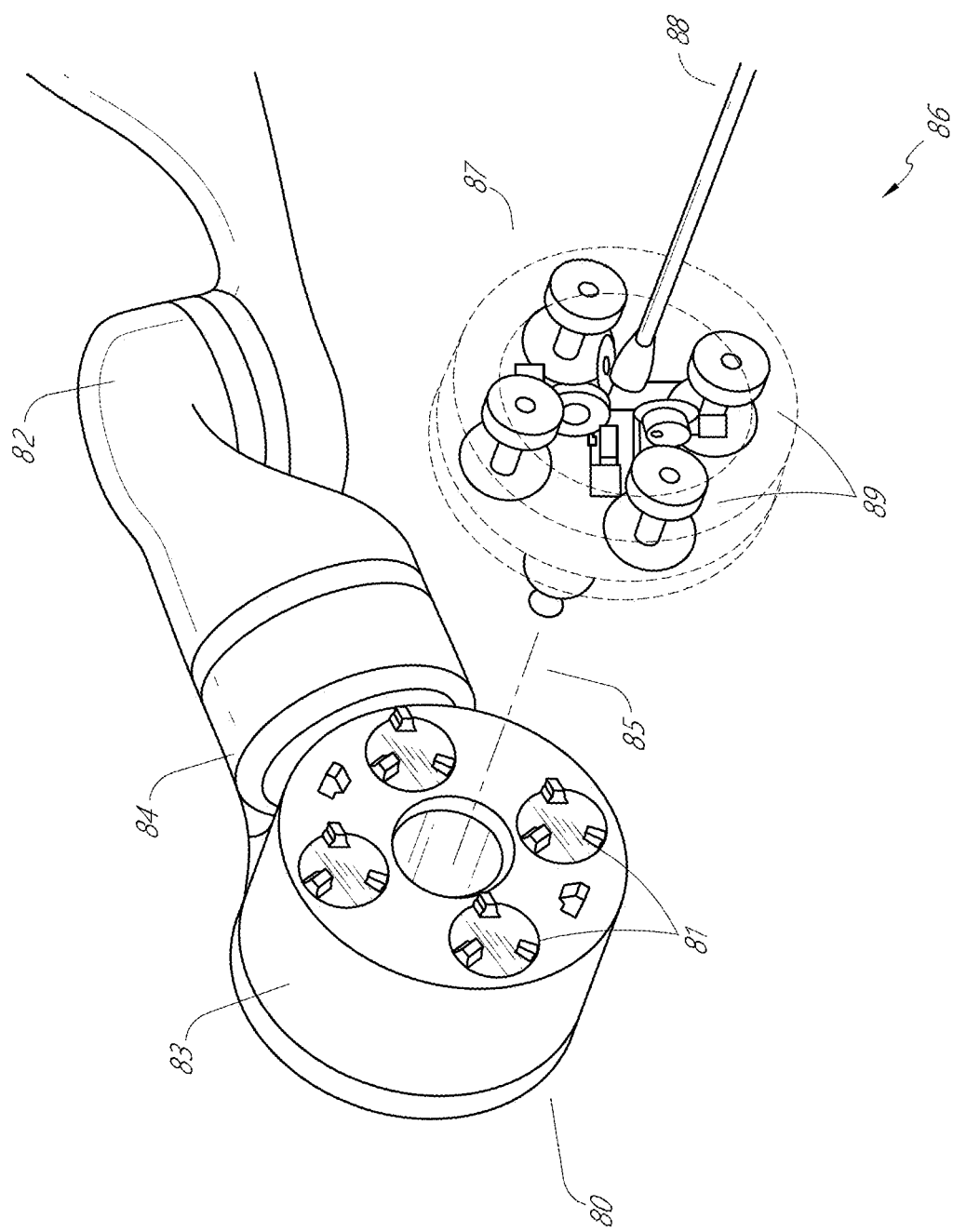
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
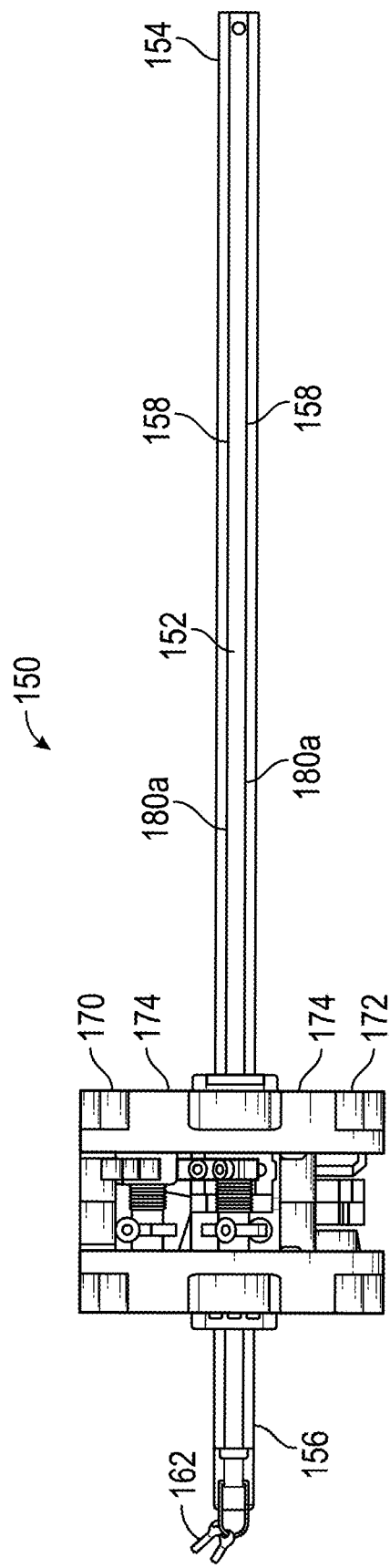
FIG. 18 illustrates an instrument having an instrument-based insertion architecture.

FIG. 18 illustrates an instrument 150 having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
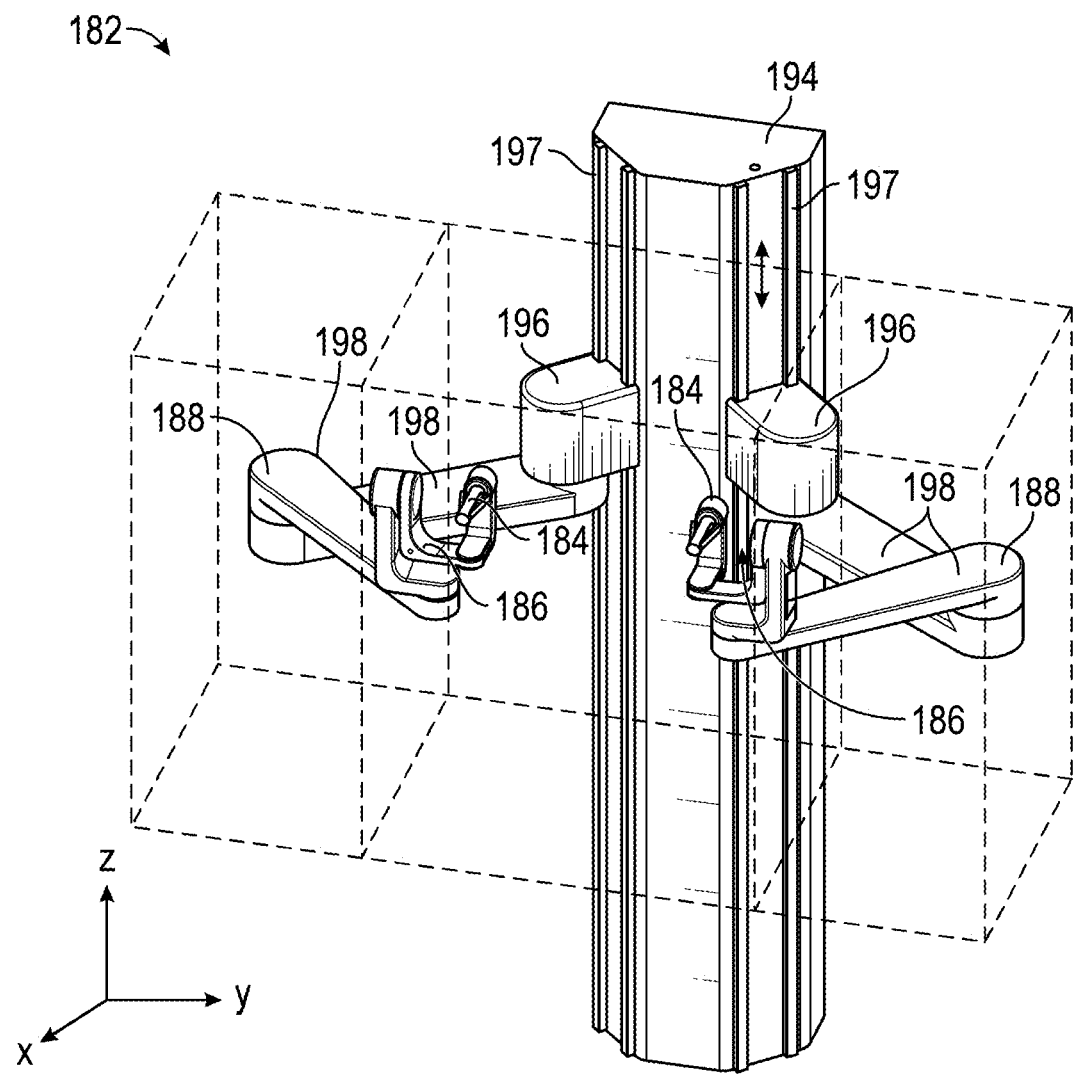
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a selective compliance assembly robot arm (SCARA) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
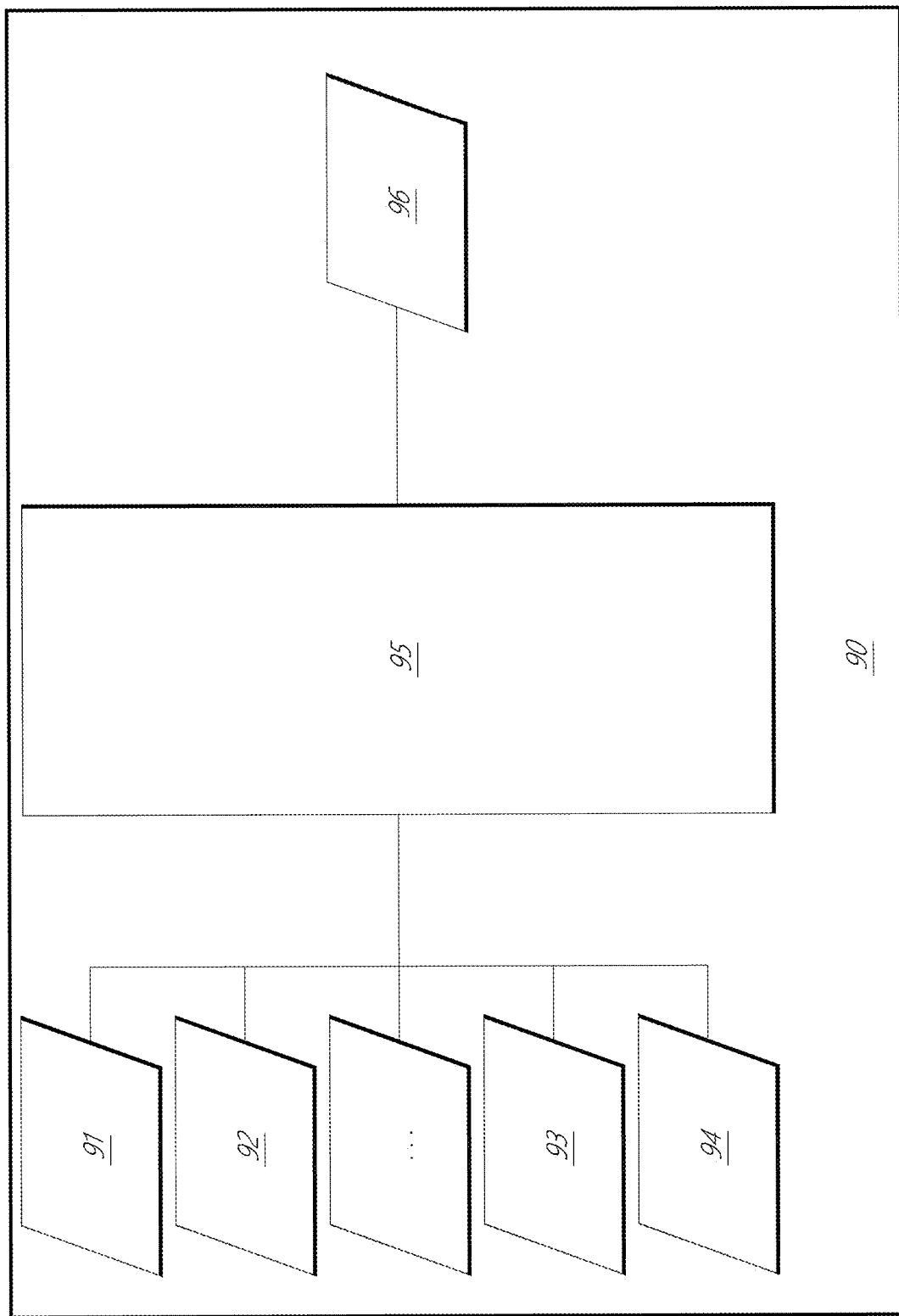
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be used by the localization module 95 to generate model data 91. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92 to the localization module 95. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking and EM data 93 to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Axial Motion Drive Devices for Robotic Medical Systems

This section relates to drive devices that are configured to drive axial motion of a shaft of a medical instrument. The drive devices can be used, for example, to drive insertion of the shaft of the medical instrument into a patient during a medical procedure. The medical instrument can be, for example, a ureteroscope, a gastroscope, a bronchoscope, as well as other types of endoscopes and laparoscopes. The shaft of the medical instrument can be configured for insertion into a patient. The shaft can be, for example, an elongated shaft, a flexible shaft and/or an articulable shaft. Axial motion can include movement of the shaft of the medical instrument in a direction along the longitudinal axis of the shaft. For example, axial motion can include insertion and/or retraction of the shaft into and/or out of the patient and/or relative to the drive devices.

The drive devices can be used with robotic medical systems, including those described above with reference to FIGS. 1-20, those described below, and others. In some embodiments, the drive devices can be used to perform various medical procedures, such as, for example, ureteroscopy, gastroscopy, bronchoscopy, and others. In some embodiments, the drive devices can be reusable, reposable, or disposable tools that are configured to couple to a robotic arm, instrument drive mechanism, and/or adapter as described above. In some embodiments, the drive devices can include gearing or mechanism assemblies to facilitate various features associated with loading and driving axial motion of a shaft of another medical instrument or tool.

Figure 22:
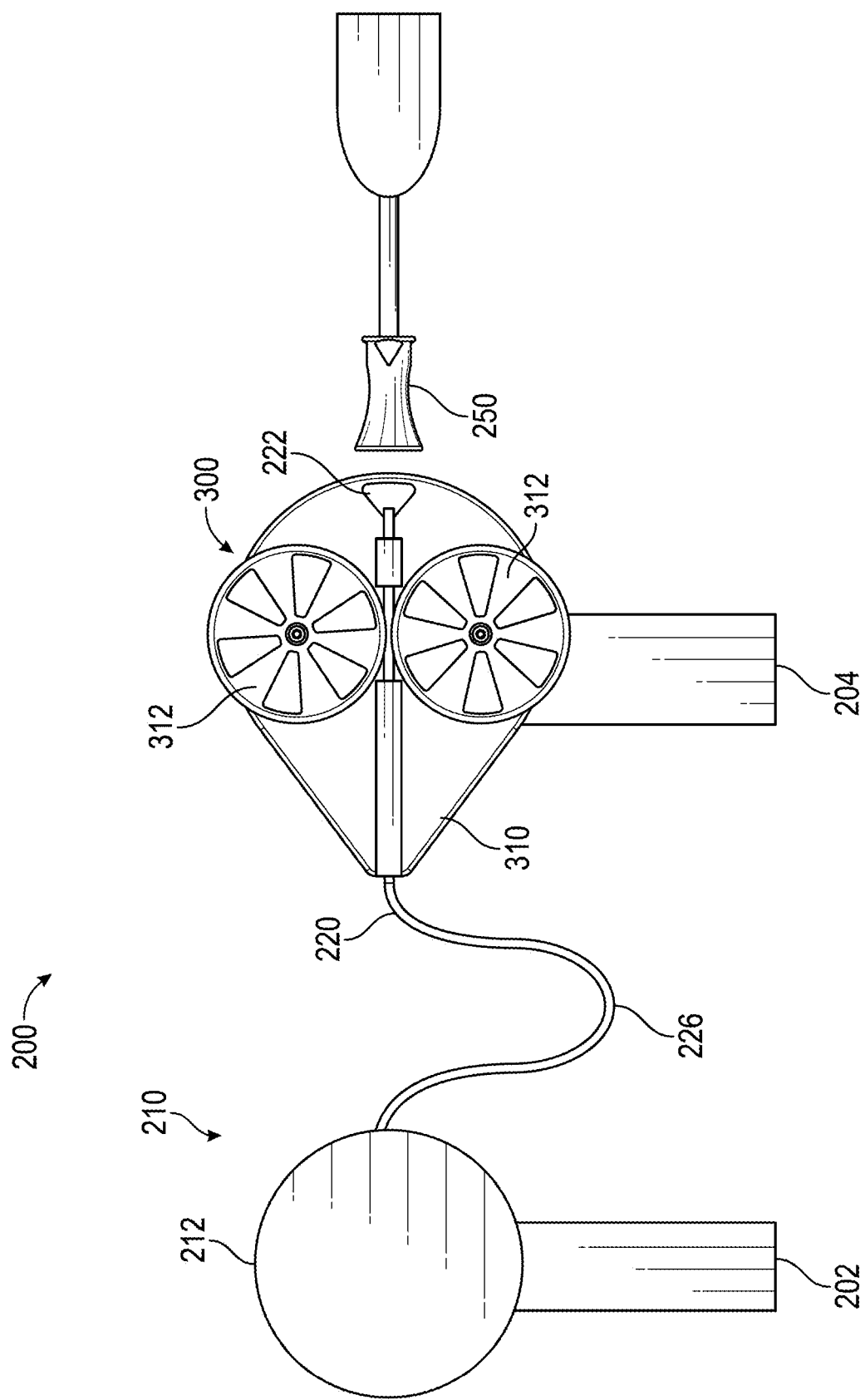
FIG. 22 illustrates the robotic medical system of FIG. 21 in another configuration wherein the elongated shaft of the medical instrument is arranged to form a service loop.

As will be described in further detail below, the drive device (also referred to as drive assembly) can be configured to pull or push the shaft of a medical instrument through drive device. The drive device can be engaged with the shaft at a position along the length of the shaft. In some embodiments, the drive device includes a set of opposing rollers (also referred to as "feed rollers") that engage with the shaft and drive axial motion (e.g., insertion and/or retraction) as the rollers rotate. In some embodiments, the drive device can include a tread system, a rack and pinon system, or other mechanism (e.g., a linear mechanism) for driving axial motion of the shaft. In some embodiments, the drive device can be configured to generate and utilize a service loop (or service loops) during insertion and retraction of the shaft. As used herein, a service loop can refer to a length of the shaft of the instrument between an instrument base (from which the shaft extends) and the drive device that is longer than the distance between the instrument base and the drive device. The service loop can thus provide slack between the instrument base and the drive device. An example of a service loop 226 is shown in FIG. 22, described more fully below.

In general, the drive devices and related robotic systems and methods described herein can provide one or more advantages over other devices and systems. In some cases, the drive devices described herein can allow for insertion and/or retraction of the shaft of the medical instrument at increased or higher speeds compared to other robotic systems. For example, in some robotic systems, the rate at which robotically-controlled ureteroscopes can be inserted into and/or retracted from a patient (e.g., through the urethral opening to the renal pelvis) is limited by the linear speed of the robot arm. In such systems, insertion and retraction speeds are limited by how quickly the robotic arm can move. The drive devices and related robotic systems described in this section can, in some embodiments, allow for increased insertion and/or retraction speeds. In some embodiments, the drive devices can allow for insertion and/or retraction speeds that are greater than the linear speeds of the robotic arms in the system. Increasing insertion and/or retraction speeds can greatly decrease the overall time required to perform some medical procedures, which can, for example, improve patient outcomes. For example, in the case of ureteroscopy, the ureteroscope may be inserted into and retracted from the kidney many times in order to capture and remove all of the kidney stones and kidney stone fragments. Thus, increased insertion and/or retraction speeds cumulatively decrease the total time required for the procedure, decreasing costs and improving patient outcomes.

Similarly, in some instances, the drive devices and related robotic systems described herein can provide improved insertion depth (or stroke length) compared to some other robotic systems. In some robotic-arm based systems, insertion depth (stroke length) can be limited to the stroke length of the robotic arm. This may be insufficient for some procedures, such as gastroscopy, which can require a large insertion depth or range. Further, moving a robotic arm through its entire possible stroke length during a procedure can pose a kinematic challenge and may risk colliding the arm with other objects, which can be undesirable and dangerous. As will be described below, the drive devices of this application can, in some embodiments, increase insertion depth beyond the stroke length of a robotic arm.

As another example, the drive devices and related robotic systems described herein can reduce or prevent shaft buckling during insertion. Because the shaft is typically flexible, buckling can occur when driving insertion from the rear (e.g., from the instrument handle or instrument base) of the medical instrument. Such buckling can occur because the robot arm applies a force to the end of a relatively long, flexible, and unsupported shaft length. The drive devices can reduce or eliminate buckling because, in some embodiments, they drive insertion of the shaft at point that is located in proximity to the point at which the shaft is inserted into the patient, also referred to as the access point. The drive devices can provide an insertion force that acts on the shaft of the medical instrument at a location close to the access point, rather than at the proximal end of the shaft, which may be located relatively far from the access point. By applying a force with the drive device along the length of the shaft and at a position proximal to the insertion point, the drive devices described herein can reduce or eliminate shaft buckling.

Additionally, the drive device can be configured to limit the amount of force that the shaft of the medical instrument can impart on the patient's tissue during insertion or retraction. This can be accomplished, as will be described more fully below, by configuring the drive device such at the drive mechanism (e.g., the rollers that are engaged with the shaft)

slip relative to the shaft at a prescribed force. This can prevent or reduce the likelihood that the shaft can exert a force higher than the prescribed force on the patient. By tuning this drive force, the system can ensure that a level of applied force, deemed to be tolerable or safe for the patient, is maintained.

The features and advantages of the drive devices and associated robotic systems will now be more fully described with reference to the FIGS. 21-33. These figures depict several example embodiments that are intended to illustrate and not limit the scope of the application.

A. Axial Motion Drive System with Multiple Robotic Arms

Figure 21:
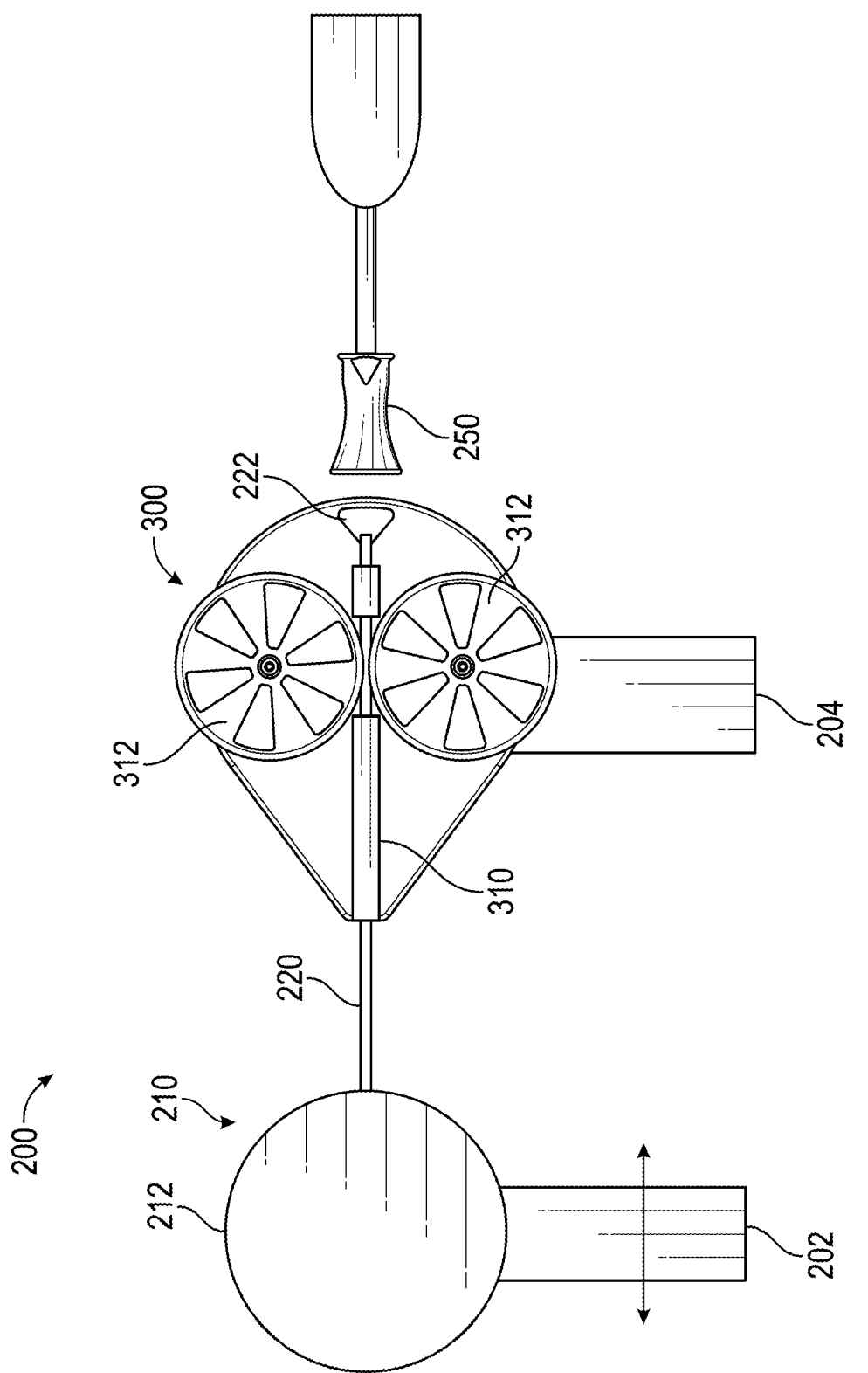
FIG. 21 illustrates a representation of a robotic medical system including a drive device configured to drive axial motion of an elongated shaft of a medical instrument.

FIG. 21 illustrates a representation of a robotic medical system 200 including a drive device 300 configured to drive axial motion of an elongated shaft 220 of a medical instrument 210. In the illustrated embodiment, the system 200 includes the medical instrument 210, the drive device 300, a first robotic arm 202, and a second robotic arm 204. As illustrated the system 200 also includes an access sheath 250, which has been inserted into the patient and which provides a conduit through which the shaft 220 of the medical instrument 210 can be inserted.

In the illustrated embodiment, the medical instrument 210 includes an instrument base 212 (also referred to as an instrument handle) and the shaft 220. The shaft 220 can extend from or through the base 212. The medical instrument 210 can be, for example, one of the medical instruments described above, such as the instrument 13 of FIG. 1, the instrument 32 of FIG. 3, the instrument 34 of FIG. 4, the instrument 40 of FIG. 5, the instrument 56 of FIG. 8, the instrument 59 of FIG. 9, the instrument 70 of FIG. 16, the instrument 86 of FIG. 17, the instrument 150 of FIG. 18, or others. As noted above, the medical instrument 210 can be an endoscope, catheter, or a laparoscope. In the illustrated embodiment, the medical instrument 210 is a ureteroscope, although this example should not be construed as limiting. According to some embodiments, the first robotic arm 202 can support multiple medical instruments, and the drive device 300 can be configured to drive motion of any one or more of the multiple medical instruments. For example, the first robotic arm 202 can support a first medical instrument having a working channel, such as an endoscope or catheter, and a second medical instrument, which can be a working channel instrument that extends within the working channel, such as a biopsy tool, basketing tool, laser fiber tool, ablation tool, or other tool that is configured to manipulate or interact with a target within the patient's anatomy.

The instrument base 212 can be configured to attach, mount, or otherwise be connected or coupled to the first robotic arm 202. The first robotic arm 202 can include an instrument drive mechanism, for example, as described above with reference to FIGS. 16 and 17, and the instrument base 212 can be attached to the instrument drive mechanism. The instrument drive mechanism can include drive outputs configured to engage with and actuate corresponding drive inputs on the instrument base 212 to manipulate the medical instrument 210. The robotic arm 202 can also be configured to move to manipulate the position of the instrument base 212 in space.

The shaft 220 can be configured for insertion into the patient. In some embodiments, the shaft 220 comprises an elongated shaft, a flexible shaft, and/or an articulating shaft. The shaft 220 can be connected at a proximal end to the instrument base 212 and can extend to a distal end that is configured to be inserted into the patient. In some embodiments, the shaft 220 extends through the base 212, for example, as shown in FIG. 18.

As shown in FIG. 21, the shaft 220 can be engaged with the drive device 300. In the illustrated embodiment, the drive device 300 includes rollers 312 which can engage or contact the shaft 220. In some embodiments, the rollers 312 can comprise or include a deformable material that provides grip, friction, traction or pressure between the rollers 312 and the shaft 220. In some embodiments, the deformable material comprises silicone rubber. In the illustrated embodiment, as the rollers 312 rotate, the shaft 310 can be pulled, pushed, or otherwise driven axially through the drive device 300. Rotating the rollers 312 in a first direction can cause insertion of the shaft 220 (e.g., in a distal direction toward the patient), and rotating the rollers 312 in a second opposite direction can cause retraction of the shaft 220 (e.g., in a proximal direction away from the patient). Here, the direction of the rollers 312 refers to the direction of the portion of the rollers 312 that engages the shaft 220. For example, rotation in the first direction for insertion of the shaft 220 refers to rotation of the engagement portion of the rollers 312 in a distal direction, and rotation for retraction refers to rotation of the engagement portion of the rollers 312 in a proximal direction. With respect to the view of the rollers 312 as seen in FIG. 21, this means that the left roller 312 rotates counterclockwise while the right roller 312 rotates clockwise to rotate the rollers 312 in the distal direction, and vice versa to rotate the rollers 312 in the proximal direction. As mentioned above, other drive mechanisms or assemblies can be used in place of or in addition to the rollers 312.

As shown in FIG. 21, the shaft 220 can pass through a channel 310 of the drive device 300. In the illustrated embodiment of FIG. 21, the channel 310 comprises a closed channel. In other embodiments, such as the embodiment illustrated in FIG. 23, the channel 310 can comprise an open channel 310. Use of an open channel 310 can facilitate loading the shaft 220 of the medical instrument 210 into the drive device 300, which can simplify use of the device and decrease operating times. For example, an open channel can facilitate loading and/or unloading of the medical instrument 210 intraoperatively, or during a medical procedure, to allow a user such as a medical practitioner to manually make adjustments to the medical instrument 210, without having to fully retract the medical instrument 210 from within the patient. In some embodiments, and as further described below, the drive device 300 can include a robotically-actuated cover that allows the channel 310 to be selectively opened or closed to facilitate loading of the shaft to the drive device or retention of the shaft on the drive device, as desired.

Figure 23:
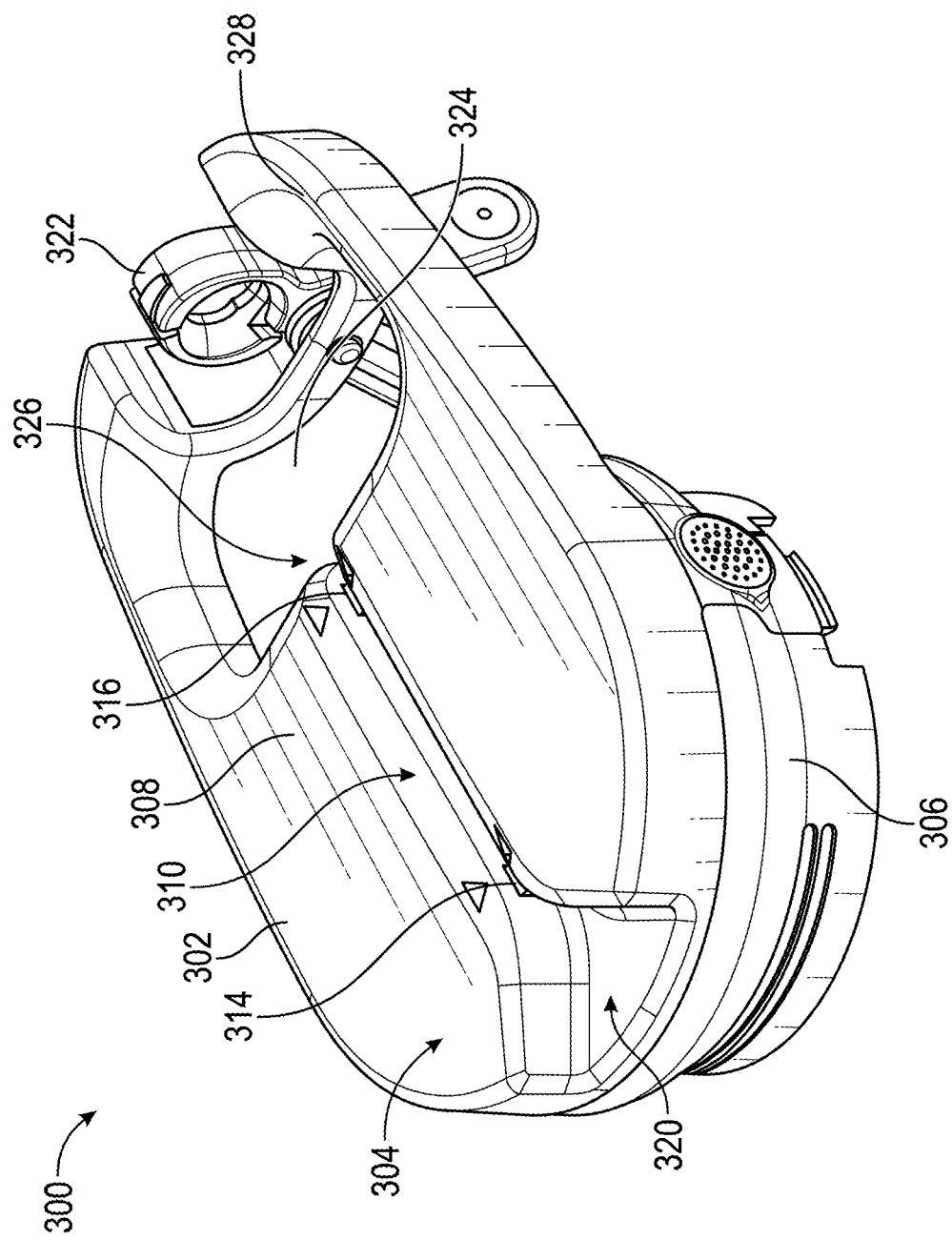
FIG. 23 is an isometric view illustrating an embodiment of a drive device configured to drive axial motion of an elongated shaft of a medical instrument.

The drive device 300 can be attached, mounted or otherwise connected or coupled to a second robotic arm 204 as shown, for example, in FIG. 21. The second robotic arm 204 can include an instrument drive mechanism, and the drive device 300 can be attached to the instrument drive mechanism. The instrument drive mechanism can include drive outputs configured to engage and actuate corresponding drive inputs on the drive device 300 (see, for example, drive inputs 334, 338 in FIG. 24C) to actuate or operate the drive device 300. The robotic arm 204 can also be configured to move to manipulate the position of the drive device 300 in space. In some embodiments, for example, as illustrated in FIG. 21, the drive device 300 can be positioned in proximity to the access sheath 250, for example, within 1 inch, within 1.5 inches, within 2 inches, within 3 inches, within 4 inches, within 5 inches, within 6 inches, or within 12 inches of the access sheath 250. Positioning the drive device 300 in proximity to the point at which the shaft 220 will be inserted can reduce buckling as noted above. As shown in FIG. 23, in some embodiments, the drive device 300 can be configured to attach to the access sheath 250 (e.g., using the clip 322), although this need not be the case in all embodiments. In some embodiments, and as further described herein, attaching the drive device 300 to the access sheath 250 can facilitate movement or repositioning of the access sheath 250, as desired, via movement or repositioning of the drive device 300 or robotic arm 204 that is coupled with the access sheath 250.

In the case of ureteroscopy, the access sheath 250 can comprise a ureteral access sheath. In some embodiments, however, the access sheath 250 may comprise a tube or other structure through which the shaft 220 can be inserted. In some embodiments, the access sheath 250 may comprise an elongate and flexible access sheath configured to be inserted into an anatomical lumen. In other procedures, other types of access sheaths can also be used. In some embodiments, no access sheath 250 is used and the elongated shaft 220 of the medical instrument 210 can be inserted directly into the patient (for example, through a natural patient orifice or other surgical access port or incision).

FIG. 21 also illustrates that the drive device may include a collector 222. In some embodiments, objects removed from the patient using the medical instrument 210 can be deposited into the collector 222. For example, in the case of ureteroscopy, the medical instrument 210 can include a basketing device configured to capture and retrieve stones or stone fragments from within the patient. Once a stone is captured, the shaft 220 can be retracted until the distal end is positioned over the collector 222. The basket can then be opened dropping the stone into the collector 222. In some embodiments, the collector 222 need not be positioned on the drive device, for example, as shown in FIG. 23.

In FIG. 21, the shaft 220 of the medical instrument 210 extends directly between the instrument base 212 and the drive device 300. In this configuration, as the drive device 300 drives axial motion of the elongated shaft, the first robotic arm 202 can move the instrument base 212 at a rate and in a direction that corresponds to the rate of axial motion provided by the drive device 300. In this case, insertion speed of the shaft 220 can be limited to the speed at which the first robotic arm 202 can move the instrument base 212. This may be suitable for slow speeds. Slow speeds may be desirable, for example, when the distal tip of the shaft 220 is positioned outside of the access sheath 250 and thus exposed to the patient's tissue (e.g., at the time of insertion of the distal tip of the sheath 250 into the patient).

FIG. 22 illustrates the robotic medical system 200 in another configuration wherein the elongated shaft 220 of the medical instrument 210 is arranged to form a service loop 226 between the first and second robotic arms 202, 204, or between the instrument base 212 and drive device 300. The service loop 226 may comprise a length of the shaft 220 between the instrument base 212 and the drive device 300. When the length of the shaft 220 exceeds the distance between the instrument base 212 and the drive device 300, the shaft 220 may hang down, forming the service loop 226 between the instrument base 212 and the drive device 300. The service loop 226 can provide slack in the shaft 220 that can be used to allow for faster insertion and/or retraction. For example, during insertion, the slack in the service loop 226 can be taken up (shortening or contracting the service loop 226). During retraction, the service loop 226 can be generated (increasing in length or expanding). As used herein, expanding or contracting the service loop 226 may involve increasing or decreasing the amount of extra length that is available in the service loop 226 to provide an axial degree of freedom for the flexible shaft.

As an example, with the service loop 226, the drive device 300 can drive insertion at a rate that is faster than the rate at which the first robotic arm 202 can move the instrument base 212. As this occurs the service loop 226 will be taken up (e.g., decreased or shortened). In some embodiments, this can allow for insertion of the shaft 220 even without requiring movement of the instrument base 212 with the first robotic arm 202. In some embodiments, this can allow for the system 200 to be configured for insertion at a rate of between 100-300 mm per second, or more particularly, at a rate of between 130-190 mm per second. Other speeds for fast insertion or retraction outside of these ranges are also possible. This type of fast insertion can be suitable, for example, when the distal tip of the shaft 220 is positioned within the access sheath 250 because the access sheath 250 can protect the tissue of the patient. In some embodiments, when the distal tip of the shaft 220 extends beyond the access sheath 250 (exposing it to the patient's tissue) the system may transition to a slower insertion rate, for example, a rate of about 5-80 mm per second, or more particularly, a rate of between 20-50 mm per second. Other speeds for slow insertion or retraction outside of these ranges are also possible, where the slow insertion rate is slower than the fast insertion rate. The slower insertion rates can operate, for example, as described above with reference to FIG. 21, wherein the insertion rate of the drive device 300 matches the movement rate of the first robotic arm 202.

As another example, during retraction, the drive device 300 can drive retraction at a slower speed when the distal tip of the shaft 220 is positioned beyond the access sheath. At the slower speed, the system 200 can operate as described above with reference to FIG. 21, wherein the retraction rate of the drive device 300 matches the movement rate of the first robotic arm 202. When the tip of the shaft 220 is positioned within the access sheath 250, the system 200 can then retract at a faster rate, which can generate (increase the length of or expand) the service loop 226. Coordinated operation of the drive device 300 and movement of the first robotic arm 202 at slow speeds may help mitigate shaft buckling that could lead to inaccurate driving response if axial motion of a relatively thin and flexible shaft 220 were performed by robotic arm motion alone, although in some embodiments, slow insertion or retraction of the shaft 220 may be achieved using arm motion 202 alone while the drive device 300 is disengaged from the shaft 220.

B. Drive Device Architecture

FIGS. 23-29 illustrate an embodiment of the drive device 300 and a mechanical architecture that can facilitate robotic control. The drive device 300 includes mechanisms coupled to drive inputs that are operable to control functions of the device, such control of the rollers to advance or retract the shaft, opening or closing the rollers to facilitate loading of the shaft, and/or control of a robotically actuated cover to selectively open or close the channel that retains the medical instrument shaft on the device. FIG. 23 is an isometric view illustrating an embodiment of the drive device 300. The drive device 300 illustrated in FIG. 23 may be, for example, an embodiment of the drive device 300 described above with reference to FIGS. 21 and 22. The drive device 300 can be configured for use with a robotic medical system, such as the robotic medical systems described above with reference to FIGS. 1-22 or others. As will be described in more detail below, the drive device 300 can be configured to engage with and drive axial motion (e.g., insertion and/or retraction) of a shaft (e.g., an elongated and/or flexible shaft) or a medical instrument (such as an endoscope). For example, the drive device 300 can be used during a medical procedure to drive insertion and/or retraction of an elongated shaft of a medical instrument into and/or out of a patient. In a more specific (yet non-limiting) example, the drive device 300 can be configured to drive insertion and/or retraction of a flexible, elongated shaft of a ureteroscope into and/or out of a patient during a ureteroscopy. The drive device 300 can be used in various other procedures as well, such as bronchoscopy, endoscopy, endoluminal procedures, or transcatheter procedures, among others.

The drive device 300 can be configured to attach (e.g., connect, mount, engage, or otherwise couple with, etc.) a robotic arm of a robotic medical system. As examples, the drive device 300 can be configured to attach to any of the robotic arms 12 of the cart 11 shown in FIGS. 1-4, the robotic arms 39 of the platform 38 shown in FIGS. 6-10, or the robotic arms 142A, 142B of the system 140A shown in FIG. 14. In some embodiments, detachment of the drive device 300 allows the drive device to be a reusable, reposable, or disposable tool that may have a different useful life than the robotic arm or instrument drive mechanism, which can be a part of capital equipment. In some embodiments, the drive device 300 is configured to attach to a distal end of the robotic arm. The robotic arm can be moved or articulated to position the drive device 300 in space. For example, in some embodiments, the robotic arm can be used to position the drive device 300 in position in proximity to the patient to facilitate a robotic medical procedure. In some embodiments, the robotic arm may maintain the drive device 300 in a fixed or stationary location during the procedure. In some embodiments, the robotic arm may move the drive device 300 during the procedure.

The drive device 300 can attach to an instrument drive mechanism (or instrument driver or drive unit) of the robotic arm. As examples, the drive device 300 can be configured to attach to the instrument drive mechanisms 146A, 146B of FIG. 14, the drive unit 63 of FIG. 15, the instrument driver 74 of FIG. 16, or the instrument driver 80 of FIG. 17. The instrument drive mechanism can include drive outputs that are configured to engage and actuate corresponding drive inputs on the drive device 300. Example drive inputs 334, 338 of the drive device 300 are shown, for example, in the bottom view of FIG. 24C, described further below.

As shown in FIG. 23, the drive device 300 can comprise a housing 302. The housing 302 can be configured to surround or enclose (either partially of fully) various internal components of the drive device 300 that facilitate the functionality of the drive device 300. Various internal components of the drive device 300 will be described in more detail below. As shown in FIG. 23, the housing 302 can include an upper portion 304 and a lower portion 306. The lower portion 306 can be configured to attach to the robotic arm and/or instrument drive mechanism as mentioned above. In some embodiments, a sterile adapter can be positioned between the drive device 300 and the robotic arm and/or instrument drive mechanism in order to facilitate maintaining a sterile field during a medical procedure. In the illustrated embodiment, the upper portion 304 of the housing 302 includes an upper surface 308. The upper surface 308 can include a channel 310 formed therein.

The channel 310 can be configured to receive a portion of a shaft of a medical instrument. In some embodiments, inclusion of the channel 310 on the upper surface 308 of the drive device 300 can be advantageous because it can allow the shaft of the medical instrument to be top loaded into the drive device 300, or loaded laterally with respect to the shaft 220. That is, because the channel 310 is open from above, the shaft of the medical instrument can be inserted into the channel from above or laterally in a simple manner. For example, in some embodiments that include a channel 310 formed in the upper surface 308, it may not be necessary to thread the shaft of the medical instrument through an enclosed guide in order to engage the shaft with the drive device 300; rather, the shaft can simply be inserted into the open channel 310 on the upper surface 308 of the drive device 300. This may simplify use of the drive device 300 and advantageously reduce the time required to use the drive device 300. Further, reduction in use time can advantageously reduce the total time required to perform the medical procedure, improving patient outcomes and reducing healthcare costs.

When inserted into or positioned within the channel 310, the shaft of the medical instrument can engage with rollers 312 positioned within the housing 302 of the drive device. The rollers 312 are shown, for example, in FIGS. 24A and 24B, which illustrate the drive device 300 with the upper portion 304 of the housing 302 removed. As will be described in further detail below, the rollers 312 can be configured to contact (e.g., press against or otherwise engage) the shaft of the medical instrument within the channel 310. The rollers 312 can further be configured to rotate to drive axial motion (e.g., motion in a direction along the longitudinal axis of the shaft) of the shaft medical instrument. In some embodiments, the rollers 312 can rotate in a first direction to drive insertion of the shaft of the medical instrument and in a second direction to drive retraction of the shaft of the medical instrument.

Within the channel 310, the drive device 300 can also include one or more clips 314, 316 (also referred to as "snaps") configured to secure the shaft of the medical instrument within the channel 310. For example, in the illustrated embodiment, the drive device 300 includes a proximal clip 314 positioned at a proximal end of the channel 310 and a distal clip 316 positioned at the distal end of the channel 310. Only a portion of the proximal and distal clips 314, 316 are shown in FIG. 23. The proximal and distal clips 314, 316 are better seen, for example, in FIGS. 24A and 24B, which illustrate the drive device 300 with the upper portion 304 of the housing 302 removed. As will be described in more detail below, the proximal and distal clips 314, 316 can be configured to secure the shaft of the medical instrument within the channel 310 without restricting (or without substantially restricting) axial motion of the shaft through the channel. For example, the proximal and distal clips 314, 316 can be configured to prevent the shaft from lifting out of the channel, while still allowing the shaft to slide axially through the channel 310 freely. Further, in some embodiments, the proximal and distal clips 314, 316 can be configured to secure the shaft within the channel 310 without restricting (or without significantly restricting) the shaft's ability to roll about its longitudinal axis. For example, the proximal and distal clips 314, 316 can be configured to prevent the shaft from lifting out of the channel, while still allowing the shaft to roll about its longitudinal axis within the channel 310 freely. For example, an inner diameter of a retaining portion of the proximal and distal clips 314, 316 can be greater than an outside diameter of the shaft of the medical instrument. In some embodiments, the drive device 300 may additionally or alternatively include a cover 318, as shown, for example, in FIGS. 26A, 26B, 27A, and 27B (described below), which can also be configured to secure the shaft of the medical instrument within the channel 310.

In some embodiments, the proximal and distal clips 314, 316 can be configured to provide tactile feedback indicating to user that shaft of the medical instrument has been loaded properly into the channel 310. For example, in some embodiments, the proximal and distal clips 314, 316 can be configured such that the shaft of the medical instrument snaps through an entry portion of the clips (providing tactile feedback and serving to retain the shaft within the channel). At the same time, after the shaft has snapped through the entry portion of the clips 314, 316, the shaft can be retained within a retaining portion that comprises a diameter that is greater than the diameter of the shaft to allow instrument shaft to slide freely through it axially as described above (e.g., permitting axial motion and/or roll of the shaft).

Figure 24A:
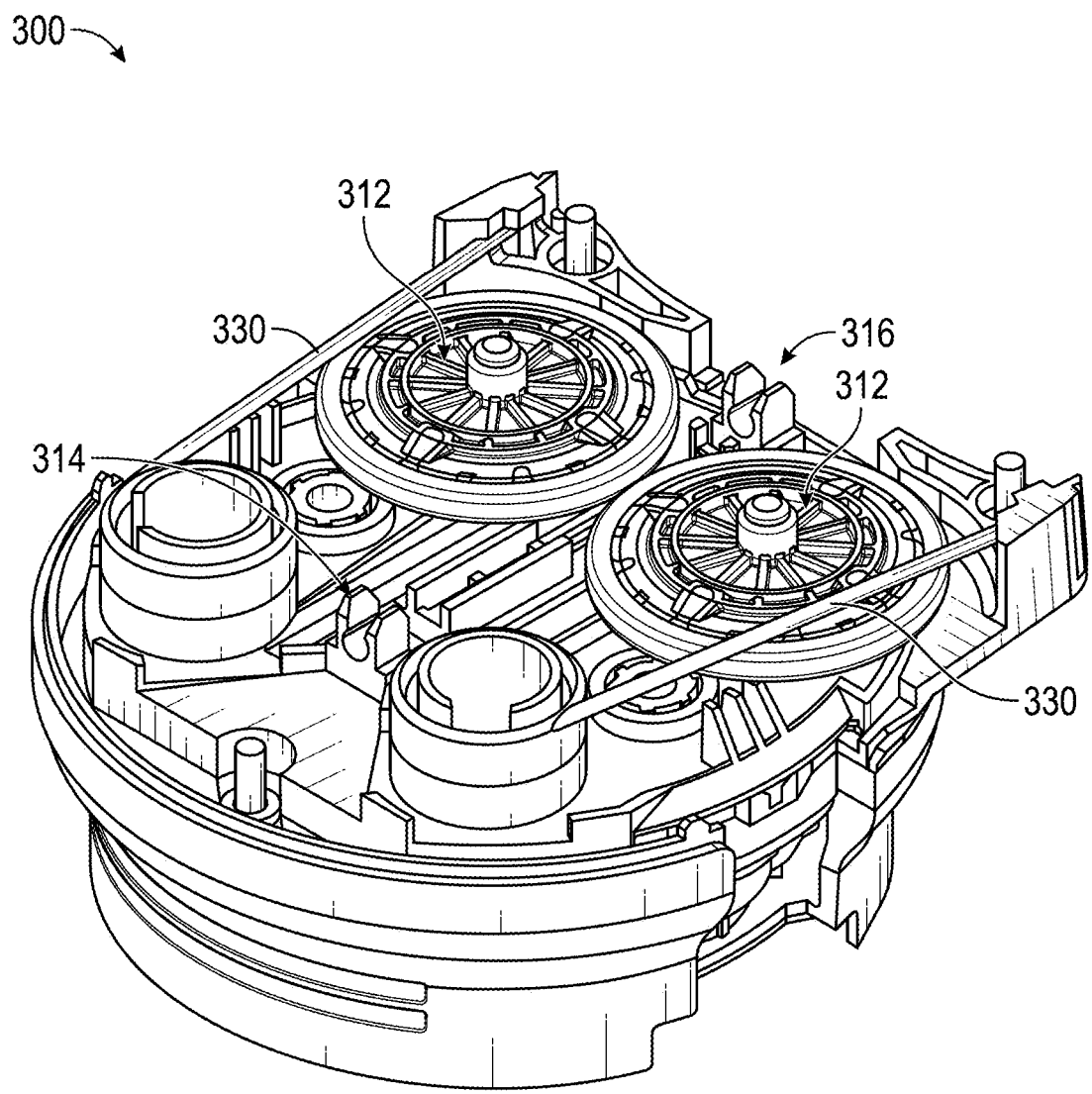
FIG. 24A is an isometric view of the drive device of FIG. 23 illustrated with a top portion of the housing removed.

In some embodiments, the channel 310 may comprise a length that facilitates the functionality of the drive device 300. As mentioned above, the drive device 300 can be configured to drive axial motion (insertion and/or retraction) of the shaft of a medical device through contact with the rollers 312 positioned within the drive device 300. In the illustrated embodiment (as shown in FIGS. 24A and 24B, for example), the rollers 312 comprise left and right rollers 312 positioned on opposing sides of the channel 310. Contact between the rollers 312 and the shaft of the medical instrument can be limited to a small contact area immediately between the opposing rollers 312. Because the contact area is relatively small (e.g., when compared with the total length of the shaft), the shaft may tend to pivot or tilt about the point at which it contacts the rollers 312. This may create difficulties in maintaining alignment of the shaft of the medical instrument. For example, the shaft may become misaligned with an access sheath or patient orifice into which the shaft will be inserted. The length of the channel 310 may be sufficient to limit or prevent this misalignment. Increasing the length of the channel 310 may limit the tendency or ability of the shaft of the medical instrument to tilt or pivot about its contact point with the rollers 312. Thus, the distal drive device 300 may be provided with a channel 310 having a length that is sufficient to limit or prevent misalignment of the shaft of the medical instrument.

In some embodiments, the length of the channel 310 can be determined between the proximal and distal ends of the channel 310. In some embodiments, the length of the channel 310 can be determined between the proximal and distal clips 314, 316. The channel 310 can comprise a length of at least 25 mm, at least 30 mm, at least 35 mm, at least 40 mm, at least 45 mm, at least 50 mm, at least 55 mm, at least 60 mm, at least 65 mm, at least 70 mm, at least 75 mm, at least 80 mm, at least 85 mm, at least 90 mm, at least 95 mm, at least 100 mm or longer. In one example that has been tested, it was found that a drive device 300 having a channel 310 with a length of about 68 mm sufficiently maintained alignment of the shaft of the medical instrument to facilitate a ureteroscopy procedure. In some embodiments, the rollers 312 are positioned to contact and engage with the shaft at a point between the proximal and distal ends of the channel 310 or at a point between the proximal and distal clips 314, 316.

In the illustrated embodiment, the channel 310 includes a flared or tapered portion 320. The tapered portion 320 can be positioned at the proximal end of the channel 310. In some embodiments, the length of the channel 310 (described above) includes the length of the tapered portion 320. In some embodiments, the length of the channel 310 (described above) does not include the length of the tapered portion 320. As described above with reference to FIGS. 21 and 22, the shaft of the medical instrument may form a service loop between the drive device 300 and a base of the medical instrument positioned proximal to the drive device 300 (for example, connected to an additional robotic arm). The tapered portion 320 can facilitate feeding the shaft into the drive device 300 at an angle and/or with a service loop, while avoiding a sharp bend in the flexible shaft. For example, the tapered portion 320 can provide a space for the flexible shaft to feed into the proximal end of the channel 310 at various angles, while sidewalls of the tapered portion can provide an enlarged bend radius or smoothed out entry point for the shaft at the region where the shaft enters the drive device. The tapered portion 320 may also accommodate a degree of misalignment between the drive device 300 and the instrument base. Further, the tapered portion 320 may facilitate feeding the shaft through the drive device 300 as the drive device 300 drives axial motion of the shaft of the medical instrument.

As shown in FIG. 23, the drive device 300 can also include a coupling member, engaging device, or holder, which is illustrated in FIG. 23 as a clip 322. The clip 322 can be positioned on a distal end of the drive device 300. The clip 322 can be configured to engage with an access sheath. The access sheath can, for example, be inserted into the patient and provide a conduit into which the shaft of the medical instrument can be inserted. In some embodiments, the clip 322 is configured to engage with a proximal end of the access sheath. In some embodiments, the clip 322 is configured to support the access sheath. For example, the clip 322 can support the proximal end of the access sheath. In some embodiments, the access sheath is supported primarily by the patient (e.g., by insertion into the patient) or by some other structure, and the clip 322 is engaged with the access sheath to orient the drive device 300 relative to the access sheath. Engaging the drive device 300 to the access sheath with the clip 322 can facilitate alignment between the drive device 300 and the access sheath. For example, engaging the clip 322 with the access sheath can align the channel 310 of the drive device 300 with the access sheath.

In some embodiments, the clip 322 can be a spring-based clip. For example, the clip 322 can include a spring, such as a torsion spring or other type of spring, that biases the clip 322 into a closed position. The spring force can be overcome to open the clip 322, and then the spring force can clamp the clip 322 onto the access sheath 250. In some embodiments, the clip 322 can be operated manually. In other embodiments, the clip 322 can be robotically controlled. In some embodiments, the clip 322 can be a self-centering clip. The self-centering feature can facilitate usability by allowing opposing sides of the clip 322 to diverge in opposite directions when opened (e.g., when manually opened or actuated by the user), then when the spring is released, the clip 322 can close onto the access sheath while maintaining alignment between a center of the clip (and thus the entry of the access sheath), with the exit of the channel 310.

In the illustrated embodiment of FIG. 23, the housing 302 of the drive device 300 is configured to include a space or gap 324 between the clip 322 and the distal end or exit 326 of the channel 310. To achieve the gap 324, the clip 322 can be positioned on an arm 328 that extends from the main body of the drive device 300. The arm 328 can be C-shaped, as illustrated, such that the gap 324 is formed between the clip 322 and the exit 326 of the channel 310 on the main body of the drive device 300. In some embodiments, the arm 328 is formed on or extends from the upper portion 304 of the housing 302. The gap 324 can be configured to allow access to a distal end of the shaft of the medical instrument when the distal end of the shaft is withdrawn from the access sheath that is engaged with the clip 322. For example, as mentioned above, the drive device 300 can be used to insert a shaft of a medical instrument into a patient through an access sheath. The proximal end of the access sheath can be engaged with the clip 322. The drive device 300 can also be used to withdraw the shaft of the medical instrument from the proximal end of the access sheath until the distal end of the shaft is positioned within the gap 324, for example, until the distal end of the shaft is positioned between the clip 322 and the exit 326 of the channel 310. This can allow access to the distal end of the shaft.

In some embodiments, the gap 324 and access to the distal tip of the shaft of the medical instrument can facilitate basketing procedures, biopsy procedures, or other procedures where an object, such as patient tissue, a foreign object, or a sample, is extracted from within a patient's anatomy. For example, in a ureteroscopy, the medical instrument can comprise a ureteroscope that can include a working channel through which a basketing device can be inserted. The basketing device and ureteroscope can be manipulated to extract kidney stones from the patient. A kidney stone can be captured in the basketing device. With the kidney stone captured, the ureteroscope can be retracted (using the drive device 300) until a distal end of the ureteroscope is positioned within the gap 324. The basket device can then be opened allowing the kidney stone to be removed. The ureteroscope can then be reinserted into the patient (using the drive device 300) through the access sheath and the process can be repeated to capture additional stones. In some embodiments, when the distal tip of the shaft is positioned within the gap 324, the removed kidney stone can be dropped or otherwise deposited into a collector. The collector can be positioned on the drive device 300 (for example, as shown in FIG. 21 or 22) or otherwise positioned below the gap 324. A similar process may be used for any other extracted object or any other working channel instrument having an end effector or tool at a distal end thereof that is capable of manipulating objects within the patient and/or releasing objects therefrom.

FIGS. 24A and 24B are isometric and top views of the drive device 300 of FIG. 23 illustrated with the upper portion 304 of the housing 302 removed. In these views, various internal components of the drive device 300 are shown, including, for example, the rollers 312 and the proximal and distal clips 314, 316, described above.

As shown in FIGS. 24A and 24B, the drive device 300 can include the rollers 312, which are configured to drive axial motion of the shaft of the medical instrument. As noted above, the rollers 312 can be positioned on opposing sides of the channel 310 so as to be positioned on opposing sides of the shaft of the medical instrument when the shaft is loaded into the drive device 300. Accordingly, the rollers 312 can be considered opposing rollers. As will be described in more detail below, the rollers 312 can be configured to move (e.g., translate) between a first position and a second position. In the first position, the rollers 312 can be configured to engage with the shaft of the medical instrument. For example, in the first position, the rollers 312 can press onto or otherwise engage with opposing or opposite sides of the shaft of the medical instrument. In some embodiments, when the rollers 312 are in the first position, they can be rotated in a first direction to drive insertion of the shaft of the medical instrument. In some embodiments, when rotated in a second direction, the rollers 312 can drive retraction of the shaft of the medical instrument. When the rollers 312 are moved to the second position, the rollers 312 can be spaced apart such that the rollers 312 are spaced apart from the shaft of the medical instrument so that they do not engage the shaft. The second position can thus be a loading position for the rollers 312. For example, the rollers 312 can be moved apart to the second position, the shaft of the medical instrument can be loaded into the channel 310, and the rollers 312 can be moved to the first position so as to engage with the shaft of the medical instrument.

In the illustrated embodiment of FIGS. 24A and 24B, the drive device 300 includes springs 330. The springs 330 can be configured to bias the rollers 312 towards the first position (e.g., the closed position, wherein the rollers 312 engage with the elongated shaft). To move the rollers 312 to the second position (e.g., the open position or the loading position) the robot drives the outputs to overcome the spring force of the springs 330. In addition to biasing the rollers 312 towards the first position, the springs 330 can also be configured to provide the pressure or friction force necessary to cause the rollers 312 to engage with the shaft of the medical instrument. For example, the springs 330 determine how forcefully the rollers 312 press into the shaft of the medical instrument. The force of the spring 330 can be selected so as to provide a desired pressure or friction against the shaft of the medical instrument. In some embodiments, the spring force of the springs 330 can be used to control or limit the pressure or force that the shaft of the medical instrument can impart on a patient's anatomy during insertion and retraction. This can be accomplished by selecting or setting the spring force, which corresponds to the frictional drive force of the rollers 312, such that the rollers 312 will begin to slip on the shaft of the medical instrument at a prescribed load. By tuning this drive force, the system can maintain a level of applied force that is deemed or defined to be tolerable or safe for a patient.

In the illustrated embodiment, the springs 330 comprise mechanical springs, such as torsion springs. Other types of springs, such as coil springs or others, may also be used. In the case of mechanical springs, the force of the springs 330 can be adjusted (to provide the safety feature described above) by adjusting the size of the springs 330 and/or the material from the springs 330 which they are made. Additionally, various other parameters of the drive device 300 can be considered as well. For example, the material of the contact area of the rollers 312 can be adjusted to provide different coefficients of friction between the shaft of the medical instrument and rollers 312. Similarly, the coefficient of friction of the shaft of the medical instrument can also be adjusted. One or more of these parameters can be configured to such that the rollers 312 slip relative to the shaft of the elongated shaft to reduce or prevent the shaft from imparting too much force on the patient's anatomy. In some embodiments, the springs 330 can be omitted, and the drive device 300 can include virtual springs that use controlled via operation of drive shafts or drive inputs to apply force against the shaft. For example, as will be described below, the drive device 300 can include various drive inputs 334, 338 that can be configured to control rotation of the rollers 312 as well as to move the rollers 312 between the first and second position (e.g., opening and closing the rollers 312). Instead of, or in addition to, including springs 330, the system can operate these drive inputs 334, 338 in a manner to provide functionality similar to that of the mechanical springs, thus providing a virtual spring that can grip against the shaft.

Figure 24C:
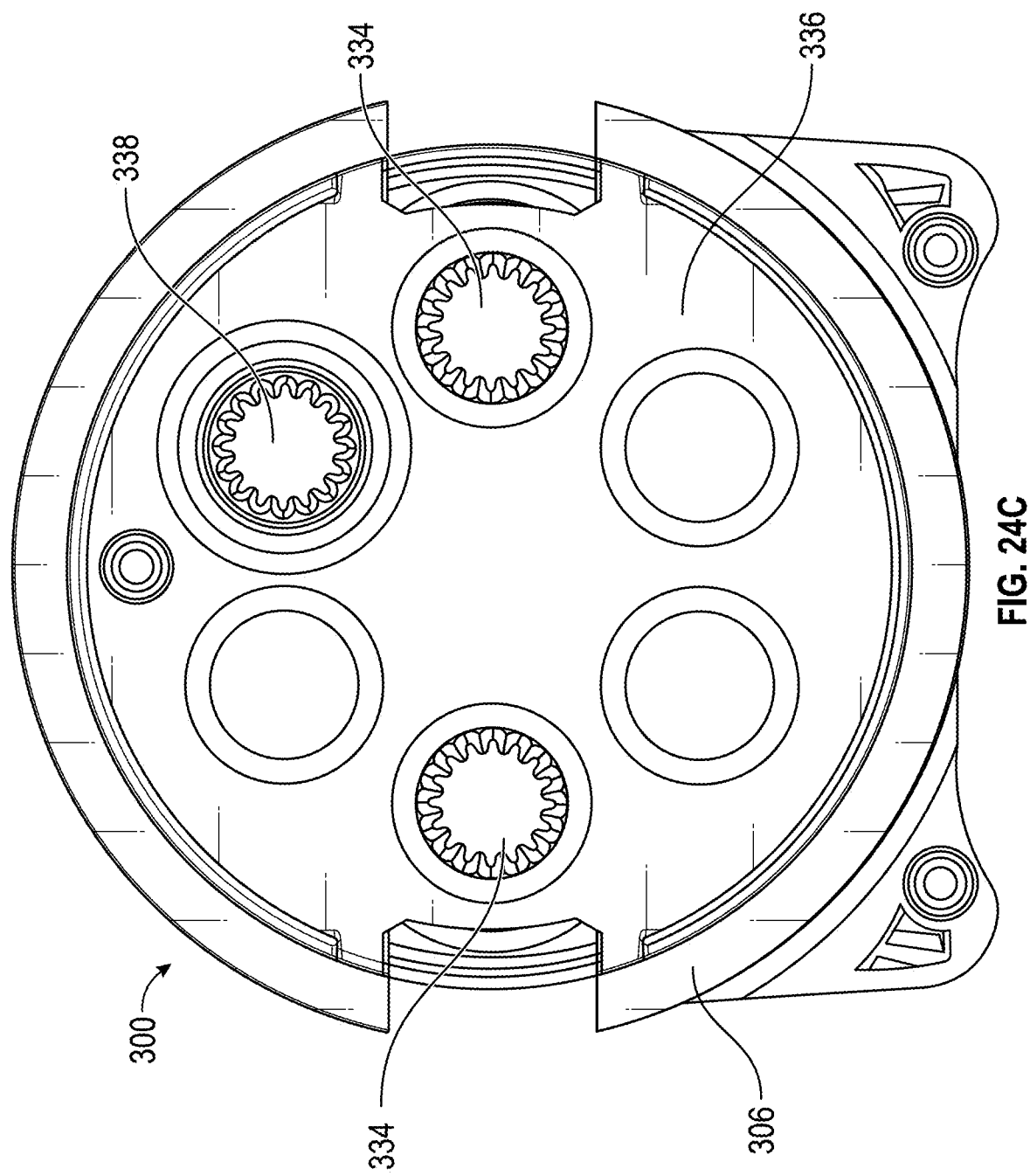
FIG. 24C is a bottom view of the drive device of FIG. 24A.

FIG. 24B also shows roller drive shafts 332. The drive shafts 332 can provide drive outputs on an instrument drive mechanism, adapter, or robotic arm, which coupled to corresponding and complementary drive inputs on the drive device 300 as further described below. In the illustrated embodiment, the roller drive shafts 332 can be configured to drive rotation of the rollers 312. For example, the drive shafts 332 can be rotated to provide a corresponding rotation at the rollers 312. As illustrated, the drive device 300 can include two roller drive shafts 332, each associated with one of the rollers 312. Thus, in the illustrated example, each of the rollers 312 can be independently driven. In some embodiments, only a single roller drive shaft 332 is included, and the single roller drive shaft 332 can be configured to drive rotation of both rollers 312. As will be described below, the roller drive shafts 332 can be connected to roller drive inputs 334 (as shown in FIG. 24C, described below). The roller drive shafts 332 can also be connected to the rollers 312. In the illustrated embodiment, the roller drive shafts 332 are connected to the rollers 312 through a gear assembly 335 (as shown in FIGS. 25B and 25C, described below). In other embodiments, the roller drive shafts 332 can be connected to the rollers 312 in other ways. As examples, the roller drive shafts 332 can be directly connected to the rollers 312 or the roller drive shafts 332 can be connected to the rollers 312 by a belt drive system.

FIG. 24C is a bottom view of the drive device 300. As shown in FIG. 24C, the drive device 300 can include a plurality of drive inputs 334, 338 on a lower surface 336 of the housing 302. The lower surface 336 can be a part of the lower portion 306 of the housing 302. In the illustrated embodiment, the drive device 300 includes three drive inputs 334, 338, although other numbers of drive inputs can be included in other embodiments. The drive inputs can be in fixed positions spaced apart along the lower mating surface 336 of the drive device 300, which facilitates coupling the drive inputs 334, 338 to corresponding drive inputs of a robotic system that may be in fixed positions spaced apart along a corresponding mating surface designed for modular use and attachment to a variety of other instruments. As further described below, a mechanical assembly within the drive device 300 can allow the drive inputs 334, 338 to be used to drive rotation of opposing rollers for axial motion of a medical instrument shaft, as well as changes in position of the opposing rollers 312 to permit loading of the shaft or allow for other use cases. In the illustrated embodiment, the three drive inputs comprise two roller drive inputs 334 and an open/close drive input 338. Each of the drive inputs 334, 338 can be configured to engage with a corresponding drive output on a robotic arm or on an instrument drive mechanism, as described above, for example, with reference to FIGS. 16 and 17. For example, each drive input can comprise a receptacle configured to mate with a drive output that is configured as a spline. The drive inputs and drive outputs can be configured to engage to transfer motion therebetween. Thus, the drive outputs can be rotated to cause corresponding rotation of the drive inputs 334, 338 to control various functionality of the drive device 300. In the illustrated embodiment, the roller drive inputs 334 can be rotated to cause rotation of the rollers 312. In the illustrated embodiment, the open/close drive input 338 can be rotated to move the rollers 312 between the first and second positions (e.g., the closed and open positions) described above. In some embodiments, the open/close drive input 338 can also be operated to actuate the cover between open and closed positions to open or close the channel in coordination with engaging or disengaging the feed rollers.

Figure 24D:
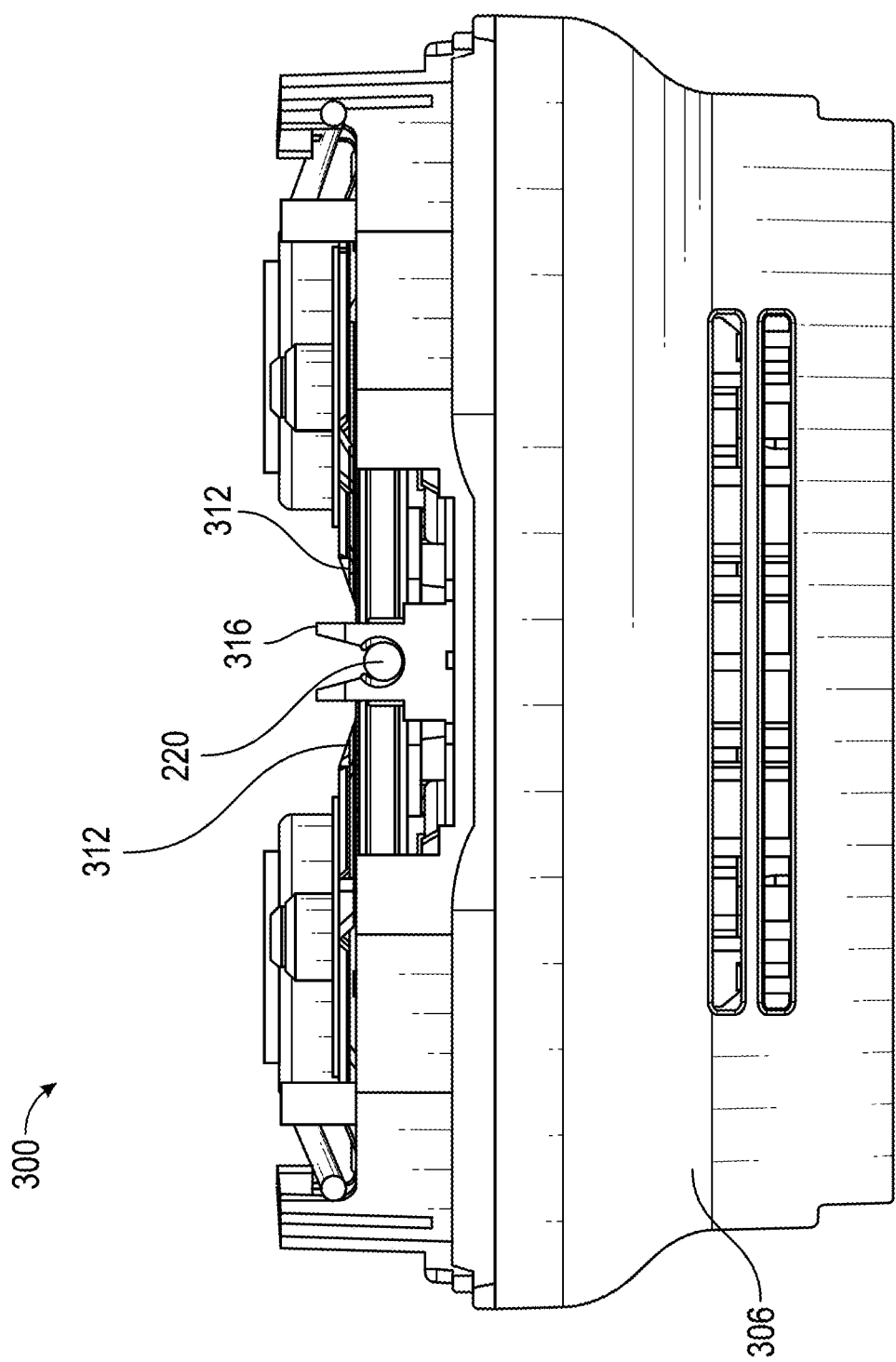
FIG. 24D is a front view of the drive device of FIG. 24A.
Figure 24E:
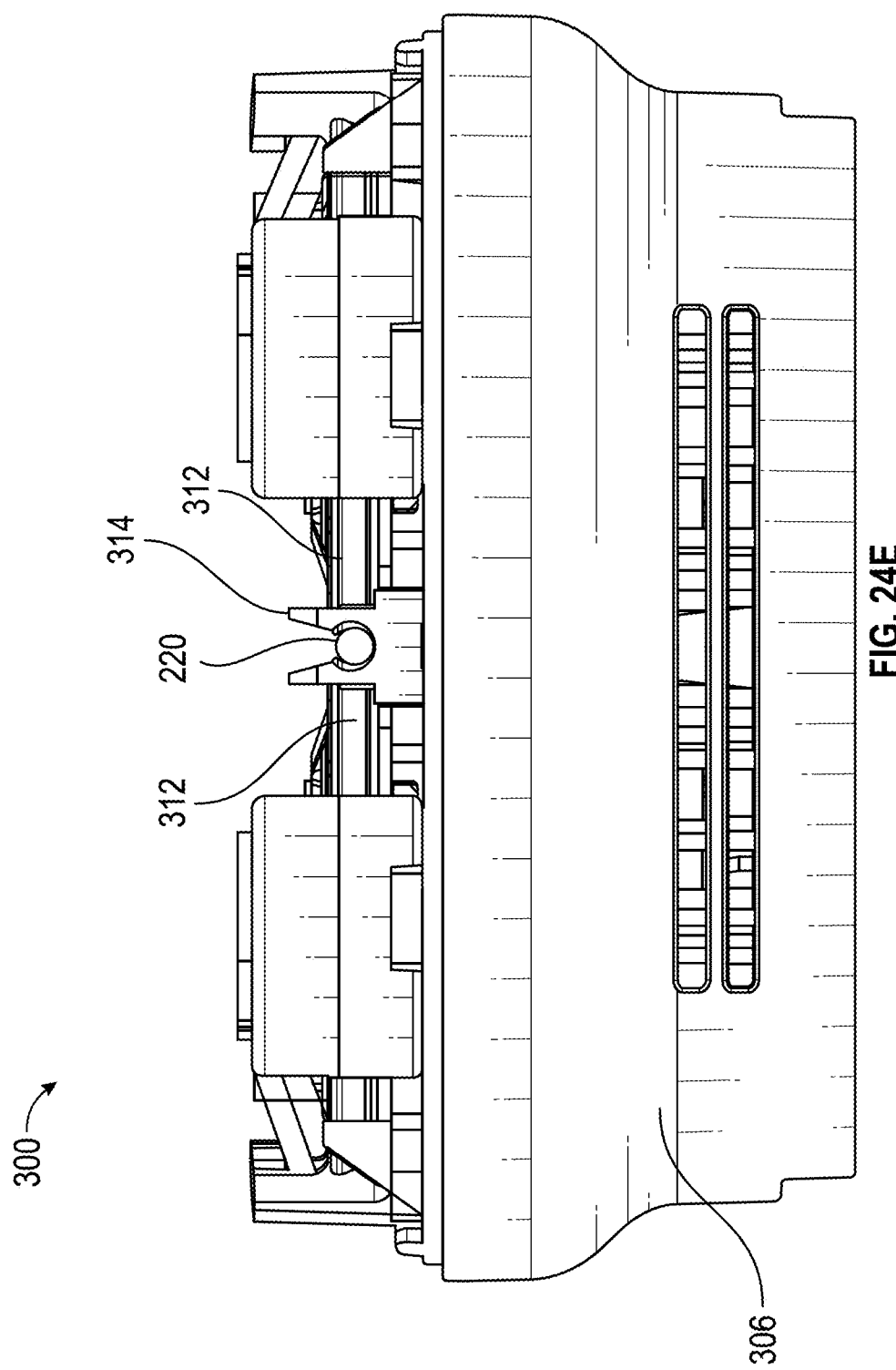
FIG. 24E is a rear view of the drive device of FIG. 24A.

FIGS. 24D and 24E are a front (distal) and rear (proximal) views of the drive device 300. In these views, a shaft 220 of a medical instrument has been illustrated so as to depict the engagement between the rollers 312 and the shaft 220. As shown, the rollers 312 are engaged with opposite or opposing sides of the shaft 220. The shaft 220 is positioned between the rollers 312. In the illustrated embodiment, the rollers 312 are shown in the first position, wherein the rollers 312 press into or otherwise engage with the shaft 220. In this position, the rollers 312 can rotate to drive axial motion (e.g., insertion or retraction (into or out of the page relative to the orientation shown in FIGS. 24D and 24E)).

FIGS. 24D and 24E also illustrate an example relationship of the proximal and distal clips 314, 316 with the shaft 220 when the shaft 220 has been loaded into the drive device 300. As shown, the proximal and distal clips 314, 316 can retain the shaft 220 within a portion of the clips 314, 316 that has a diameter that is larger than the diameter of the shaft. This configuration can allow the shaft 220 to move freely in an axial direction (into and out of the page relative to the orientation shown in FIGS. 24D and 24E) and to roll freely about the longitudinal axis of the shaft 220 as described above. Above the portion of the clips 314, 316 that includes the larger diameter, the proximal and distal clips 314, 316 can include detents that are separated by a distance that it smaller than the diameter of the shaft 220. The shaft 220 can be pushed through the detents to provide tactile feedback and retain the shaft 220 within the proximal and distal clips 314, 316 as described above.

Figure 25A:
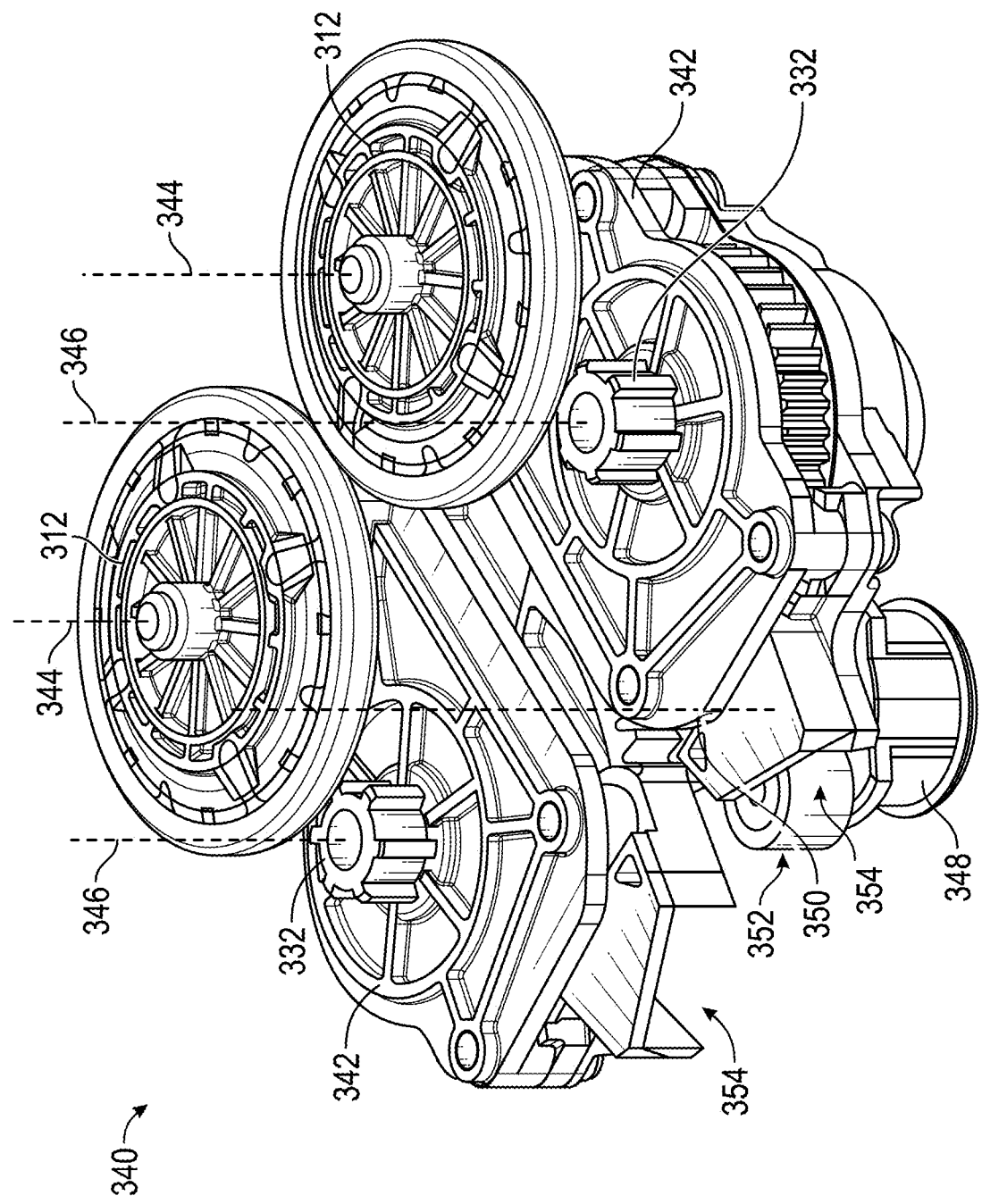
FIG. 25A is an isometric view of an embodiment of a roller assembly of the drive device of FIG. 23.
Figure 25C:
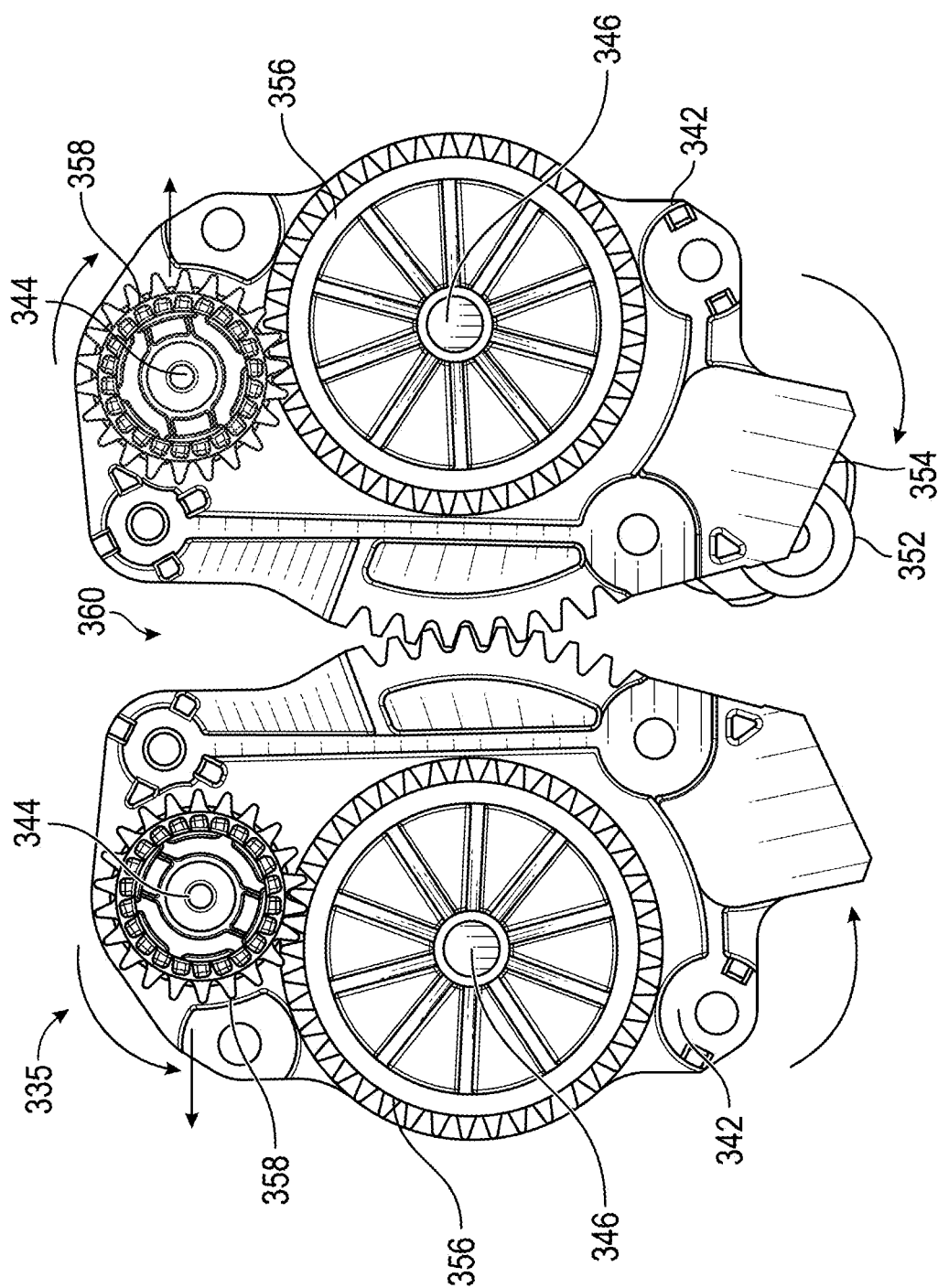
FIG. 25C is a top view of the roller assembly and gearing arrangement of FIG. 25B.

FIG. 25A is an isometric view of an embodiment of a roller assembly 340 of the drive device 300. As will be described below, in the illustrated embodiment, the roller assembly 340 can be configured to drive axial motion of the shaft of the medical instrument (by rotating the rollers 312) and also to move the rollers 312 between the first and second positions (e.g., the closed and open positions) discussed above. In the illustrated embodiment, the roller assembly 340 includes right and left assemblies. Each of the right and left assemblies can include a carrier plate 342. The term plate in used broadly to refer to a support structure, and the carrier plate 342 need not be considered necessarily flat or planar. Rather, the carrier plate 342 can comprise a complex shape or geometry configured to support various components of the roller assembly 340 as described below. The carrier plate 342 may also be referred to as a linkage or other supporting structure.

In general, the carrier plate 342 supports or is connected to various other features or structures of the roller assembly 340. For example, in the illustrated embodiment, each carrier plate 342 supports or is connected to one of the rollers 312 and one of the roller drive shafts 332. As shown in FIG. 25A, the roller 312 is configured to rotate about a roller axis 344. The roller drive shaft 332 is configured to rotate about a drive input axis 346. As illustrated, the roller axis 344 and the drive input axis 346 need not be coaxial. In some embodiments, the roller axis 344 and the drive input axis 346 are parallel (for example, as illustrated). The carrier plate 342 can also support or be connected to a gear assembly 335 as will be described below with reference to FIGS. 25B and 25C, which connects the roller drive shafts 332 to the rollers 312 such that rotation of the roller drive inputs 334 can cause rotation of the rollers 312.

In the illustrated embodiment, the carrier plates 342 can be configured to rotate about the drive input axes 346. Rotation of the carrier plates 342 about the drive input axes 346 can move the rollers 312 between the first and second (closed and open positions). As noted above, the drive device 300 can include an open/close drive input 338 that is configured to cause the rollers 312 to move between the first and second positions. The open/close drive input 338 can be connected to the open/close drive shaft 348 shown in FIG.

25A. Rotation of the open/close drive input 338 can cause rotation of the open/close drive shaft 348. The open/close drive input 338 and the open/close drive shaft 348 can rotate about an open/close drive axis 350. The open/close drive shaft 348 can further be connected to an off-axis protrusion 352. Thus, as the open/close drive shaft 348 rotates, the off-axis protrusion 352 also rotates about the open/close drive axis 350. The off-axis protrusion 352, however, is not symmetric about the open/close axis 350. Thus, the off-axis protrusion 352 provides an eccentric member that can move in an arc about the open/close axis 350.

As shown in FIG. 25A, the carrier plates 342 may each include a pocket 354. In the illustrated embodiment, the off-axis protrusion 352 is positioned at least partially within the pocket 354 of one of the carrier plates 342. As the off-axis protrusion 352 rotates about the open/close axis 350 it can contact the walls of the pocket 354, which can cause the carrier plate 342 to rotate about the drive input axis 346. The off-axis protrusion 352 can also be rotated to a position in which it does not contact the walls of the pocket 354. In this position, with the off-axis protrusion 352 not contacting the pocket 354, the force applied by the rollers 312 on the shaft of the medical instrument is determined wholly by the springs 330, which as described above can be tuned to provide a desired force. In this position, the carrier plate 342 can be biased by the springs 330 to rotate to a position in which the rollers 312 are in the first or closed position. Rotating the off-axis protrusion 352 such that it contacts and presses against the sidewalls of the pocket 354 can cause the carrier plate 342 to rotate, overcoming the spring force of the springs 330. In some embodiments, the off-axis protrusion 352 comprises a roller configured to rotate about an axis that is not coaxial with the open/close drive axis 350. Such a roller may reduce friction between the off-axis protrusion 352 and the pocket 354.

Figure 25D:
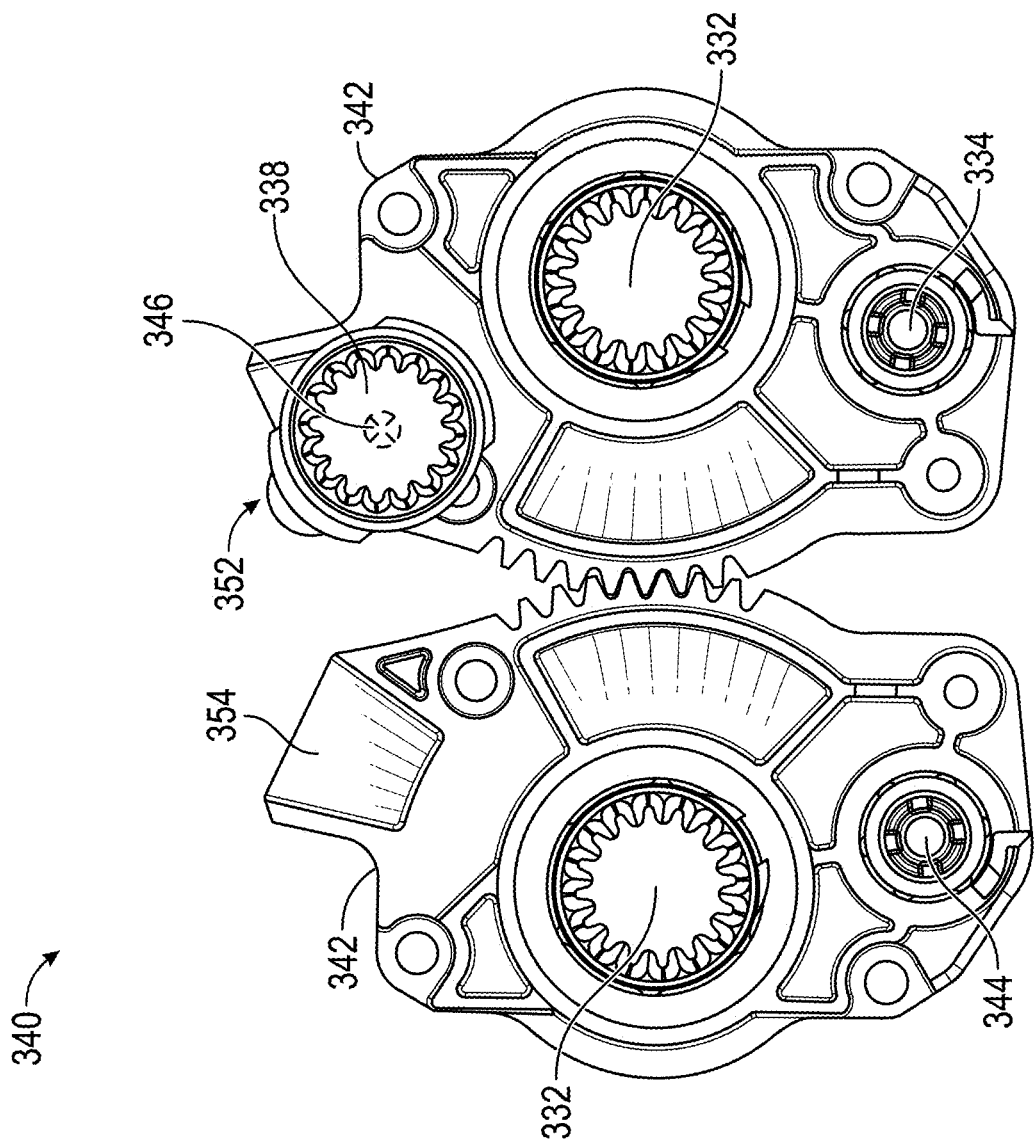
FIG. 25D is a bottom view of the roller assembly and gearing arrangement of FIG. 25B.

In the illustrated embodiment of FIG. 25A, the roller assembly 340 only includes one open/close drive shaft 348 and one off-axis protrusion 352. This is because, as best seen in FIGS. 25B-25D, the two carrier plates 342 have been geared together, such that rotation of one carrier plate 342 causes an opposite and corresponding rotation of the other carrier plate 342. In this manner, rotation of both carrier plates 342 can be driven by a single open/close drive input 338 as seen in FIG. 24C. This may also facilitate that the rollers 312 are positioned symmetrically about channel 310 of the drive device 300. In the illustrated embodiment, although only one off-axis protrusion 352 is included, both carrier plates 342 include a pocket 354, and one of the pockets 354 is empty. Inclusion of the empty pocket may facilitate manufacturing as the same or similar molds can be used for each carrier plate 342. Additionally or alternatively, a second open close off-axis protrusion or other drive member can be used to independently rotate the other carrier plate, in which case the two carrier plates need not be geared together.

FIGS. 25B and 25C are isometric and top views of the roller assembly 340 of FIG. 25A with the rollers 312 and a portion of the carrier plates 342 removed to illustrate an embodiments of a gear assemblies 335 thereof. As mentioned above, the gear assemblies 335 can transfer rotational motion between the roller drive inputs 334 (FIGS. 24C and 25C) and the rollers 312 (FIGS. 24A, 24B, and 25A). As shown, the gear assemblies 335 may comprise (for each carrier plate 342) a first gear 356 (e.g., a sun gear) and a second gear 358 (e.g., an orbital gear). In the illustrated embodiment, the first gear 356 is connected to the roller drive input 332 such that rotation of the roller drive input 332 causes rotation of the first gear 356. The first gear 356 is mounted on the carrier plate 342 such that the first gear 356 can rotate with respect to the carrier plate 342. The first gear 356 can rotate about the drive input axis 346 (FIG. 25A).

In the illustrated embodiment, the first gear 356 is engaged with the second gear 358 such that rotation of the first gear 356 causes rotation of the second gear 358. The second gear 358 is mounted on the carrier plate 342 such that the second gear 358 can rotate with respect to the carrier plate 342. The second gear 358 can rotate about the roller axis 344 (FIG. 25A). The second gear 358 is also attached (or otherwise engaged with) the roller 312 such that rotation of the second gear causes rotation of the roller 312. Thus, rotation of the roller drive input 332 can cause rotation of the roller 312 through transmission by the first gear 356 and the second gear 358.

As described above, the carrier plates 342 can rotate about the drive input axis 346 to move the rollers 312 between the first position and the second position (closed and open positions). In the illustrated embodiment, because the second gear 358 is mounted on the carrier plate 342 at a location distanced from the drive input axis 346, the second/orbital gear 358 thus also rotates (with the carrier plate 342) about the drive input axis 346. As the second/orbital gear 358 rotates with the carrier plate 342 about the drive input axis 346 it also rotates about the first/sun gear 356.

This arrangement of the second/orbital gear 358 rotating about the first/sun gear 356 may be seen in the top view of FIG. 25C. As shown in FIG. 25C, the off-axis protrusion 352 can be rotated such that it contacts the pocket 354 of the carrier plate 342 to drive rotation of the carrier plate 342 in the direction indicated by the arrows in FIG. 25C. In particular, relative to the orientation shown in the figure, the bottom of the carrier plate 342 can be rotated inward, toward the center of the page, and the top of the carrier plate 342 can be rotated outward, towards the outer edge of the page. The gearing 360 causes a corresponding and opposite rotation of the other carrier plate 342. Each of the carrier plates 342 can rotate about the corresponding drive input axis 346. As the carrier plates 342 are rotated, the second/orbital gears 358 are driven outward, rotating about the sun gear 356. This arrangement can be advantageous as it allows the rollers 312 (not shown in FIG. 25C, but connected to the second/orbital gears 358) to be driven regardless of the rotational position of the carrier plates 342. This can accommodate, for example, shafts of instruments that have different diameters.

FIG. 25D is a bottom view of the roller assembly 340 illustrating the relationship of the roller drive inputs 334 and open/close drive input 338 of the roller assembly 340, according to one embodiment.

Figure 26A:
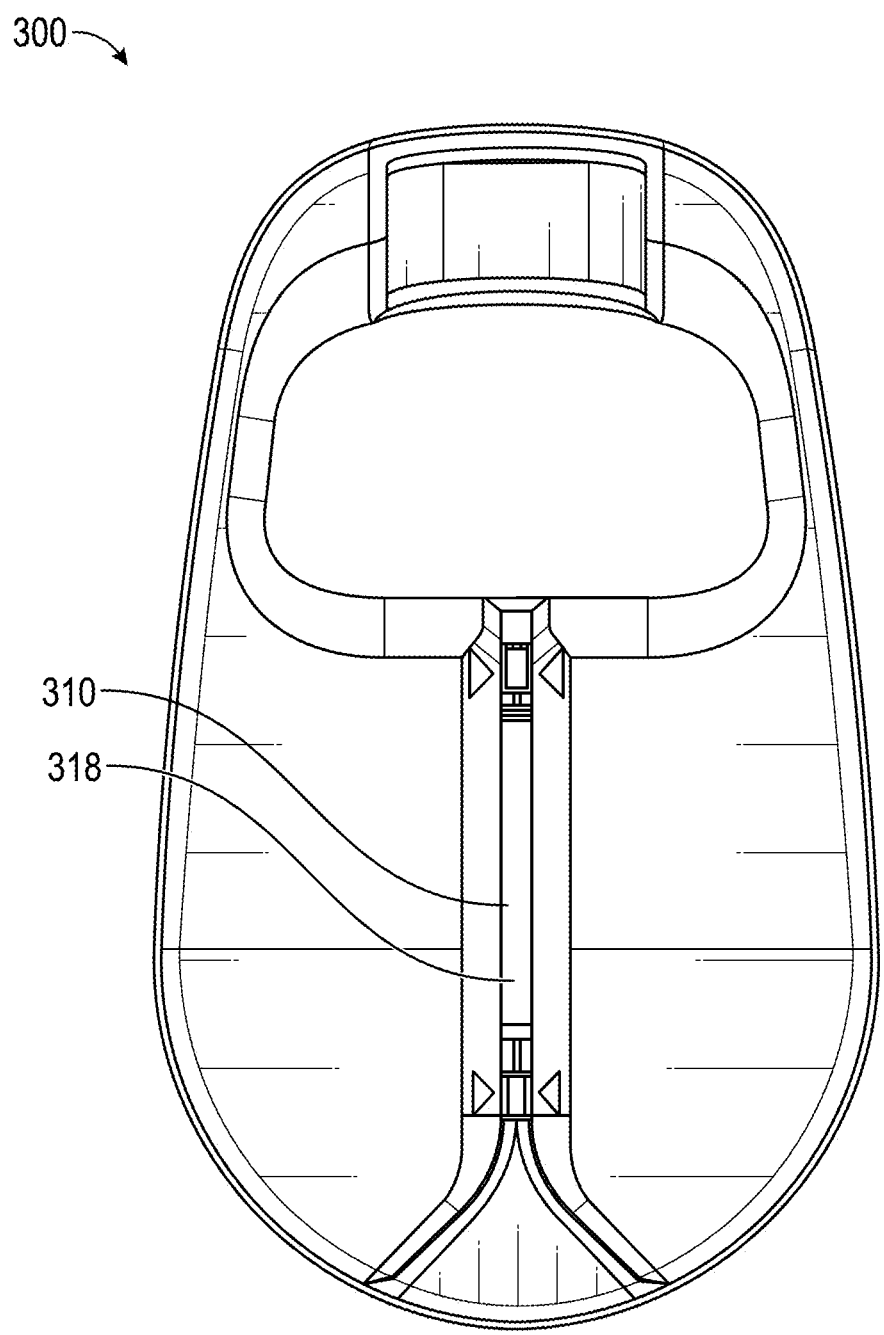
FIG. 26A is a top view of the drive device of FIG. 23, illustrating an embodiment of an instrument shaft cover in a closed configuration.
Figure 26C:
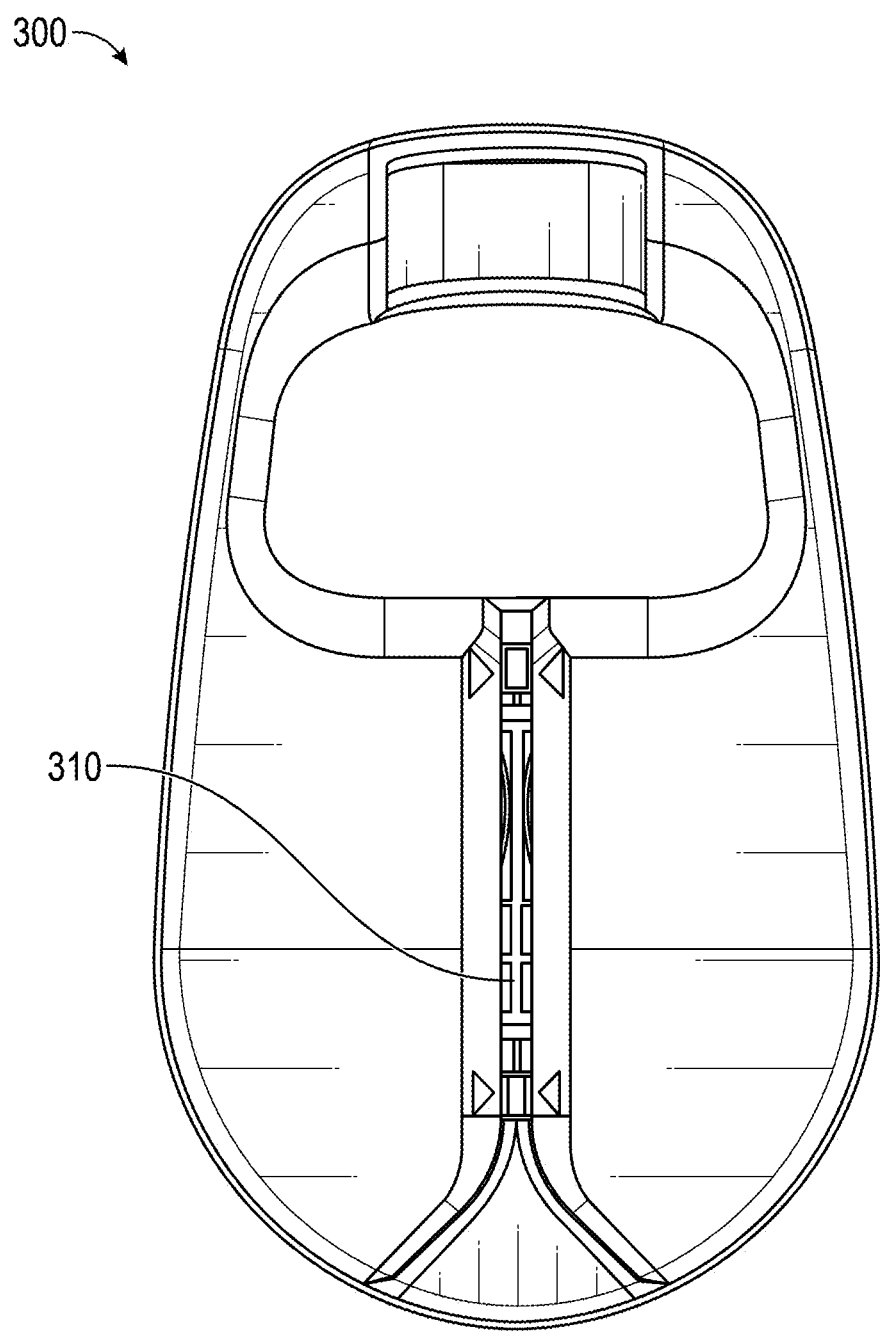
FIG. 26C is a top view of the drive device of FIG. 23, illustrating the instrument shaft cover in an open configuration.
Figure 27A:
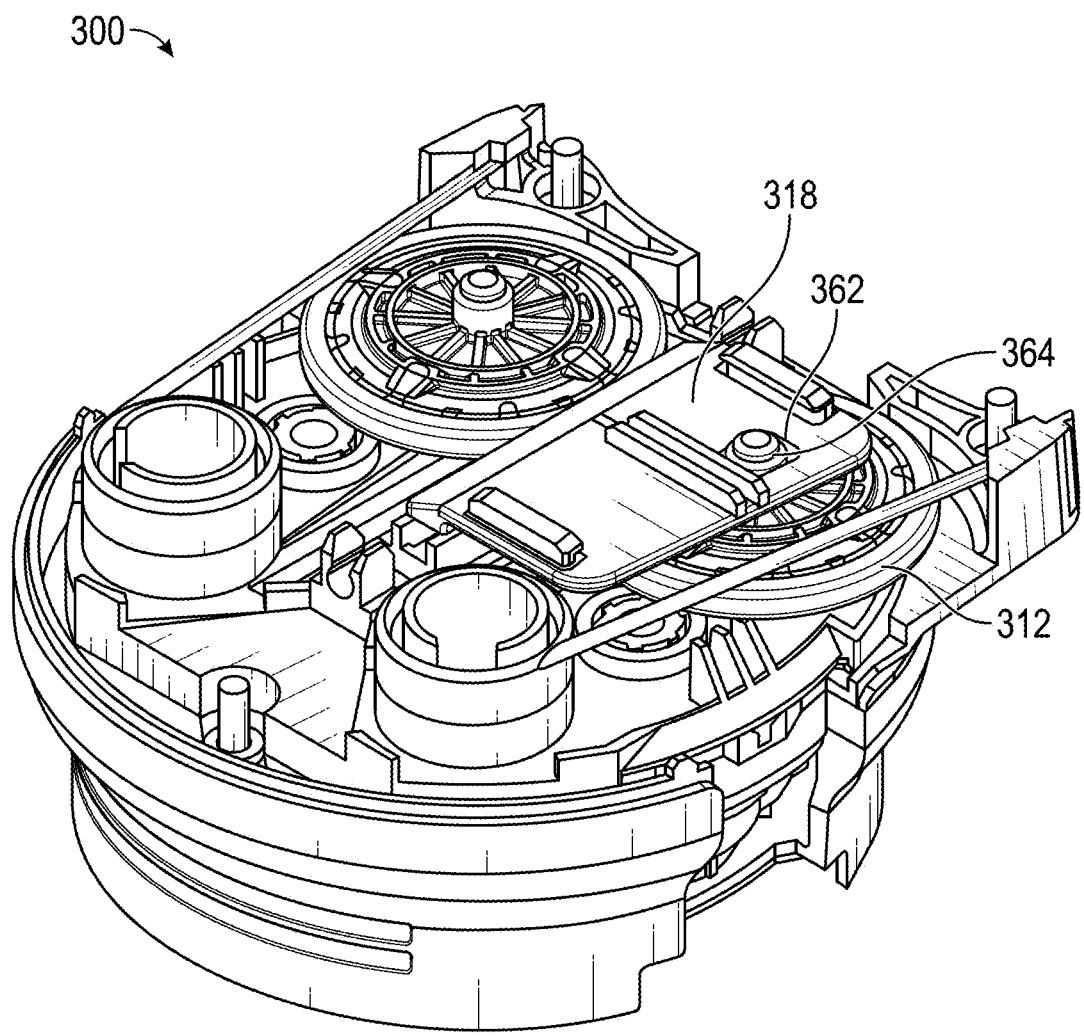
FIG. 27A is an isometric view of the drive device of FIG. 23A with a top portion of the housing removed to illustrate an embodiment of an instrument shaft cover.

FIGS. 26A-27B illustrate various features of the drive device 300 related to a cover 318 that is configured to retain or secure the shaft of the medical instrument within the channel 310 of the drive device 300. FIGS. 26A and 26B are top and side views that illustrate the cover 318 in a closed position. FIGS. 26C and 26D are top and side views the illustrate the cover 318 in an open position. FIGS. 27A and 27B are top and side views of the drive device 300 with an upper portion of the housing 302 removed to further illustrate features of the cover 318.

As illustrated in FIGS. 26A and 26B, the drive device 300 can include the cover 318, which, in a closed configuration as illustrated, can be configured to close a portion of the channel 310. When closed, the cover 318 can be configured to prevent the shaft of the medical instrument from lifting out of the channel 310. Similar to the proximal and distal clips 314, 316 previously described, when closed, the cover 318 can be configured to not limit or not substantially limit the axial motion of the shaft of the instrument through the channel 310. For example, the cover 318 can be positioned above the shaft such that it contact between the shaft and the cover 318 is limited. Similarly, the cover 318 can be configured to not limit or not substantially limit the ability to roll the shaft about its longitudinal axis within the channel 310.

FIG. 26B includes an arrow illustrating an example direction in which the cover 318 can be moved to open the cover 318. FIGS. 26C and 26D show the drive device 300 with the cover in the open position. In the illustrated embodiments, the cover 318 is a sliding or translating cover that facilitates a compact configuration for drive device 300.

FIGS. 27A and 27B illustrate an embodiment wherein the cover 318 is mechanically linked to one of the carrier plates 342 and one of the rollers 312 such that the cover 318 opens and closes automatically as the carrier plates 342 and rollers 312 are moved between the first and second positions. As shown, the cover 318 can comprise a plate positioned over one of the rollers 313. The cover 318 can include a slot 362 formed therein. The slot 362 can be engaged with cam 364 that extends from one of the rollers 312. In this example, as the roller 312 moves (for example, as the carrier plate 342 rotates) the cam 364 engages with the slot 362 to cause corresponding movement of the cover 318, opening and closing the cover 318 along with movement of the roller 312.

In some embodiments, the cover 318 can be configured to move to an intermediate position in between its open and closed positions. In the intermediate position, the cover 318 may still close the channel 310 such that the shaft of the medical instrument is retained. However, in the intermediate position the rollers 312 are disengaged from the shaft of the medical instrument, allowing the shaft to slide or roll freely through the channel 310. In some embodiments, this intermediate position of the cover 312 is used for various use cases during a procedure where retention of the shaft is desired, but more freedom of movement of the shaft relative to the drive device is desired. In some embodiments, where the position of the cover 318 is mechanically linked to the position of the rollers 312 (for example, as illustrated), the cover may be sufficiently long that it continues to close the channel 310 even as the rollers 312 first disengage from the shaft. Then as the rollers 312 continue to move away from the shaft, the cover 318 can continue to move, uncovering the channel 310. In other embodiments, the position of the cover 318 can be controlled by different methods. For example, it need not be mechanically coupled to the roller 312. In some embodiments, the cover 318 is independently controlled or not mechanically linked to the roller 312, in which case fully opening, fully closing, or any other intermediate position of the cover can be controlled by another drive input. Further, while the illustrated embodiment utilizes a cam mechanism to open and close a sliding or translating cover, but other mechanisms may be used to form an operative coupling between the drive input and cover. Additionally or alternatively, the cover may be a pivoting cover or be actuated opened or closed with other movements.

Figure 28:
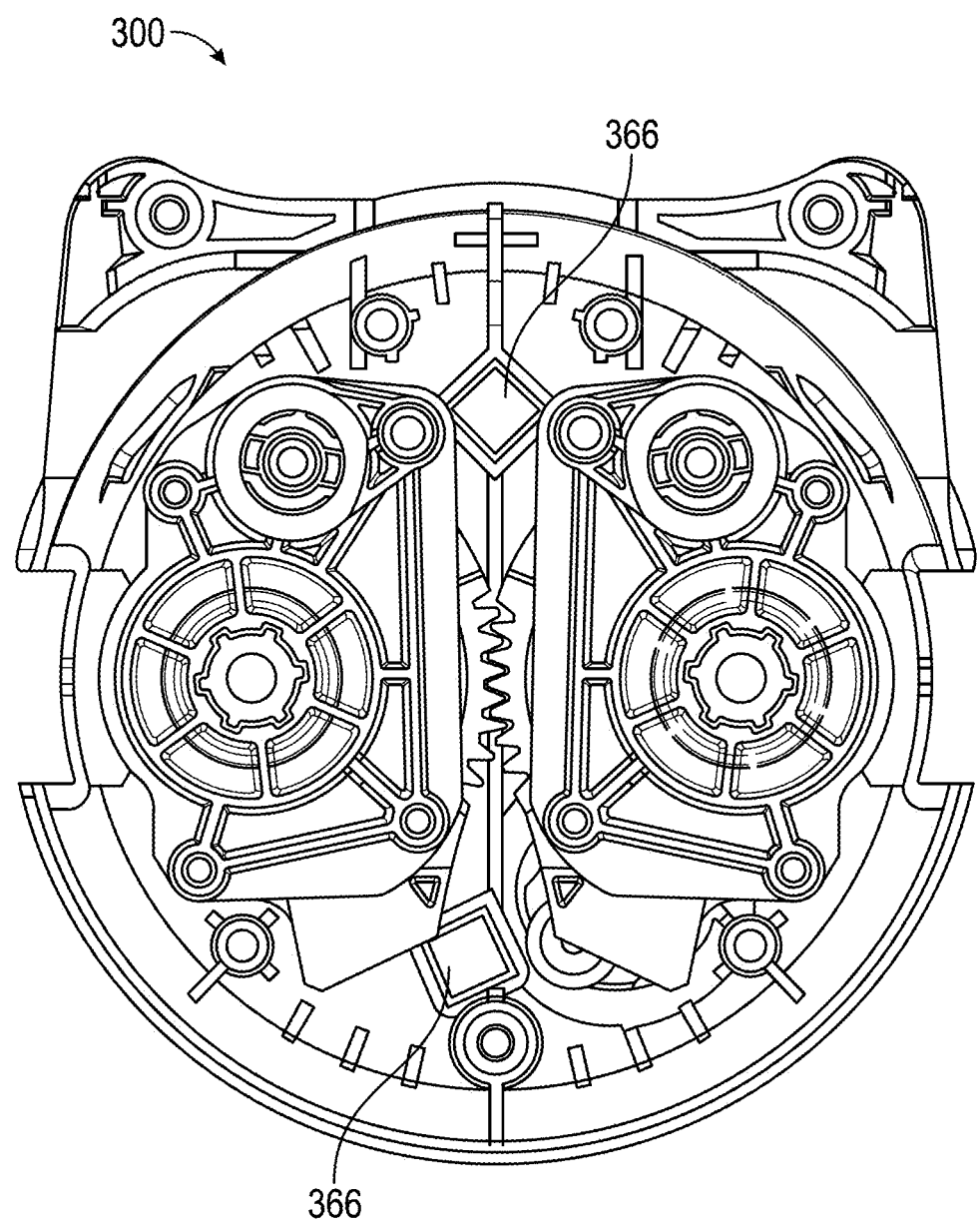
FIG. 28 is a top view of the drive device of FIG. 23 illustrated with a top portion of the housing removed to illustrate an embodiment of sensors that can be included to detect device attachment.

FIG. 28 is a top view of the drive device 300 illustrated with a top portion of the housing 302 removed to illustrate an embodiment of sensors 366 that can be included to detect device attachment. In some embodiments, the sensors 366 can comprise magnets. The magnets can be positioned so as to be detectable with corresponding sensors (such as hall effect sensors) in the instrument device mechanism to which the drive device 300 is attached. The sensors 366 can be used to detect when the drive device 300 has been engaged with the instrument drive mechanism. In some embodiments, the sensors can be used to set the position of the cover 318 and/or rollers 312 when the drive device 300 is attached to the instrument drive mechanism. For example, when the drive device 300 is connected to the instrument drive mechanism, the sensors may provide a signal indicating that the device has been attached. This can trigger the system to open the cover 318 and/or the rollers 312 such that a shaft of a medical instrument can be loaded into the device. Although magnets are described as the sensors 366, other types of sensors such as any proximity detection technology can also be used. The number and position of sensors 366 can also be different than as illustrated in FIG. 28.

Figure 29A:
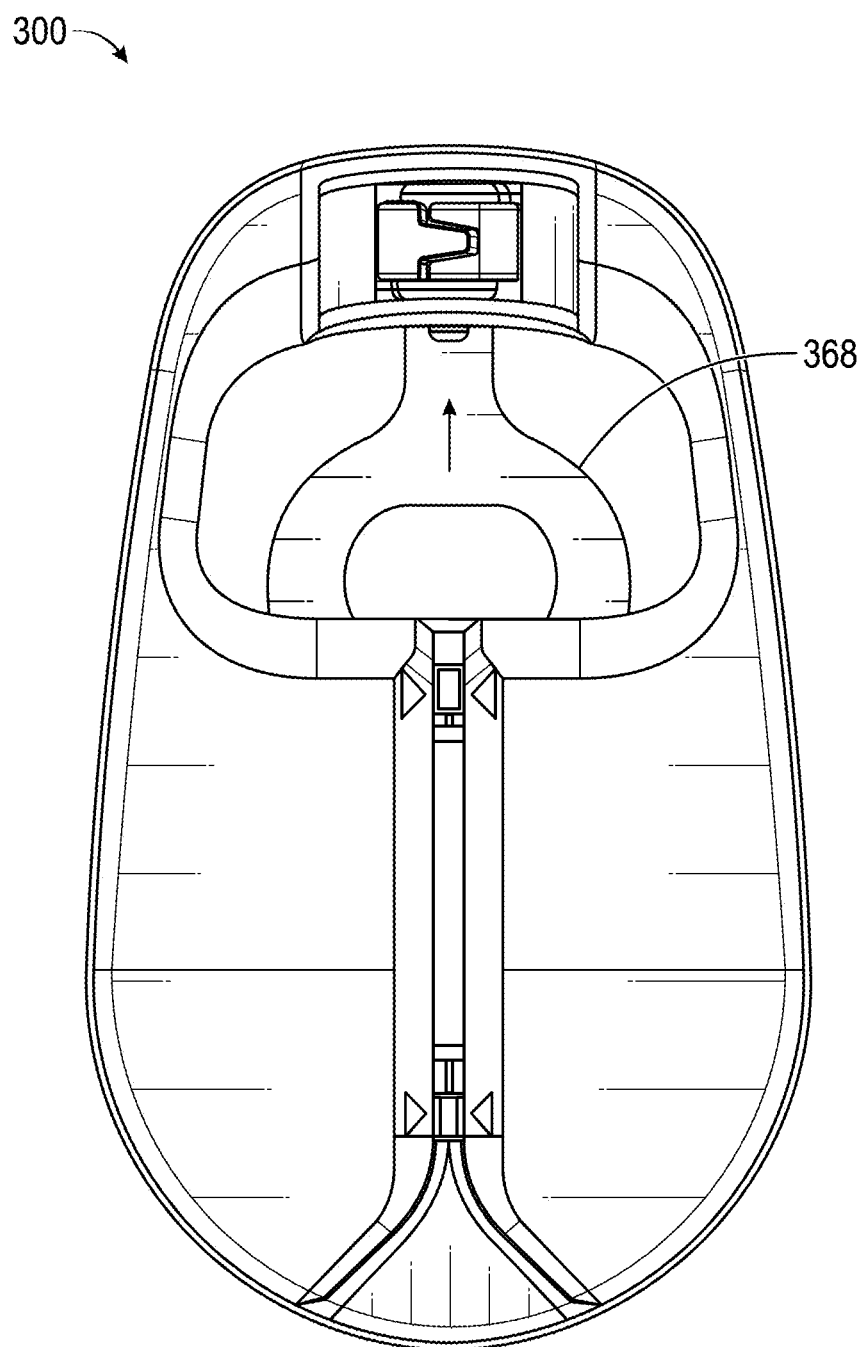
FIG. 29A is a top view of the drive device of FIG. 23 illustrated with an embodiment a locking tab installed.
Figure 29B:
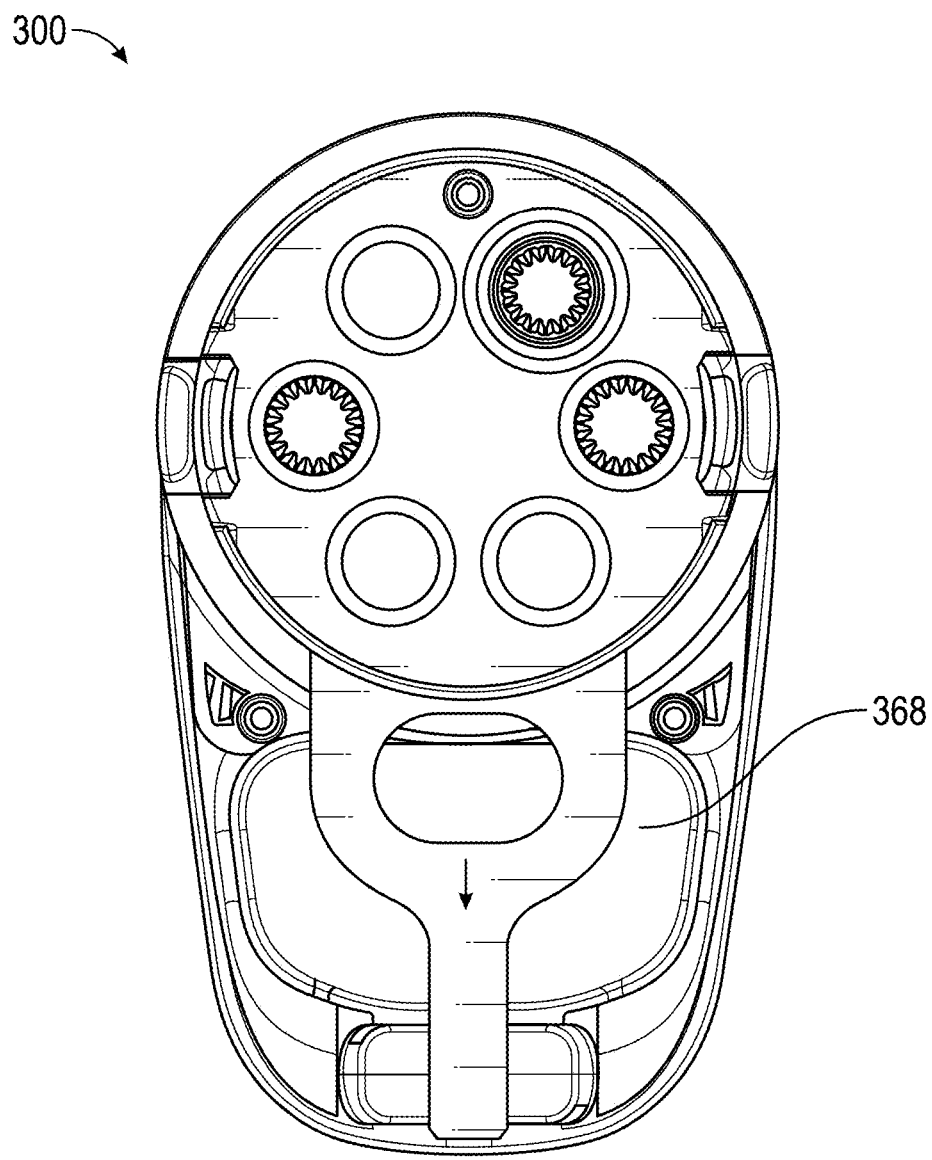
FIG. 29B is a bottom view of the drive device and locking tab of FIG. 29A.
Figure 29C:
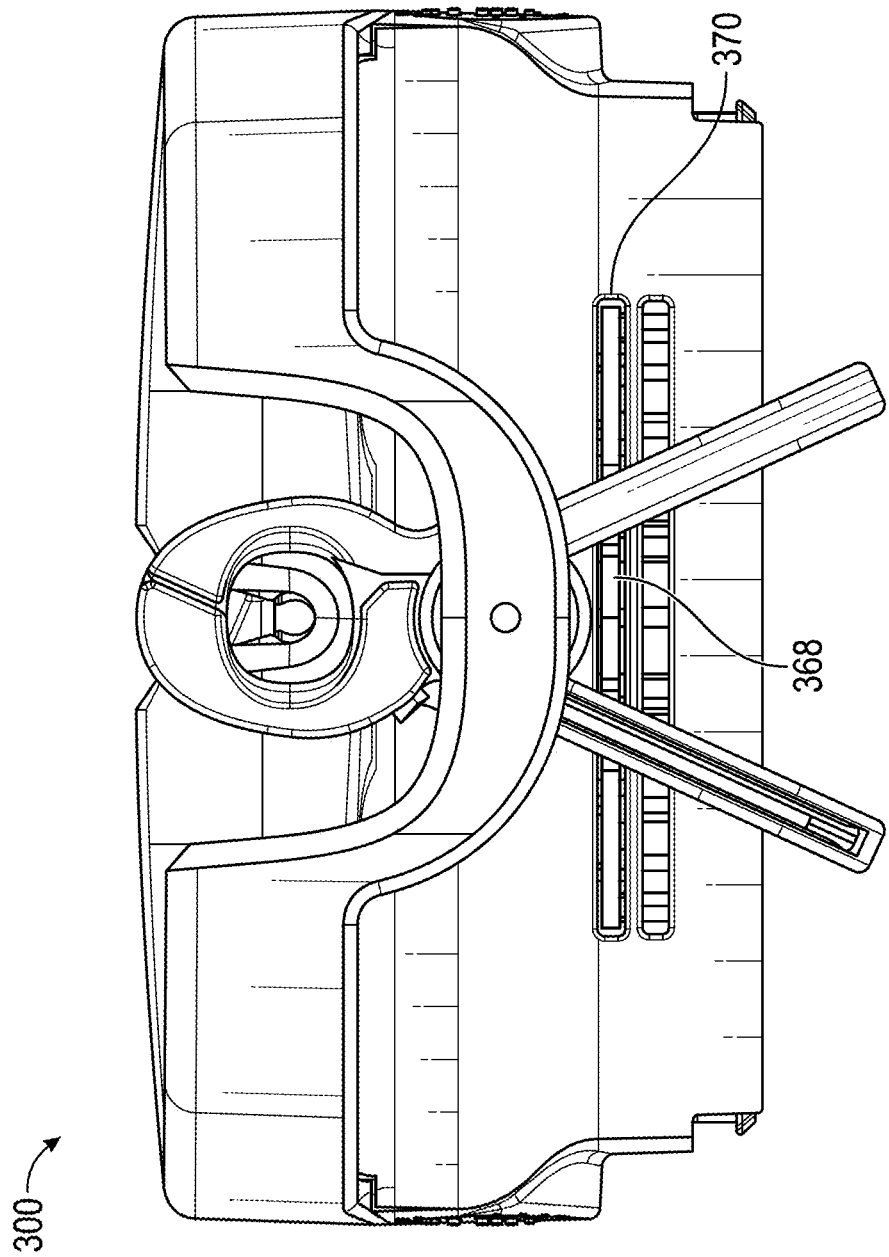
FIG. 29C is a front view of the drive device and locking tab of FIG. 29A.

FIGS. 29A-29C are top, bottom, and front views of the drive device 300 illustrated with an embodiment of a locking mechanism or tab 368 installed. In some embodiments, the locking tab 368 can be configured for use during shipping and/or storage of the drive device 300. The locking tab 368 can be configured to separate the rollers 312 such that they do not contact each other, which could cause deformation of the rollers 312 over time. The locking tab 368 can be configured to overcome the bias of the springs 330 to hold the rollers 312 in the second (or open position). In some embodiments, the locking tab interfaces with the carrier plates 342 to hold the rollers 312 apart. As best seen in FIG. 29C, the locking tab 368 can be inserted into a locking tab slot 370 on the front of the device. The locking tab 368 is removed during use of the drive device.

C. Axial Drive Device and System Operation.

FIGS. 30A-33 illustrate exemplary methods of control, and related parameters and drive device states, that may be used to control an axial drive system.

Figure 30A:
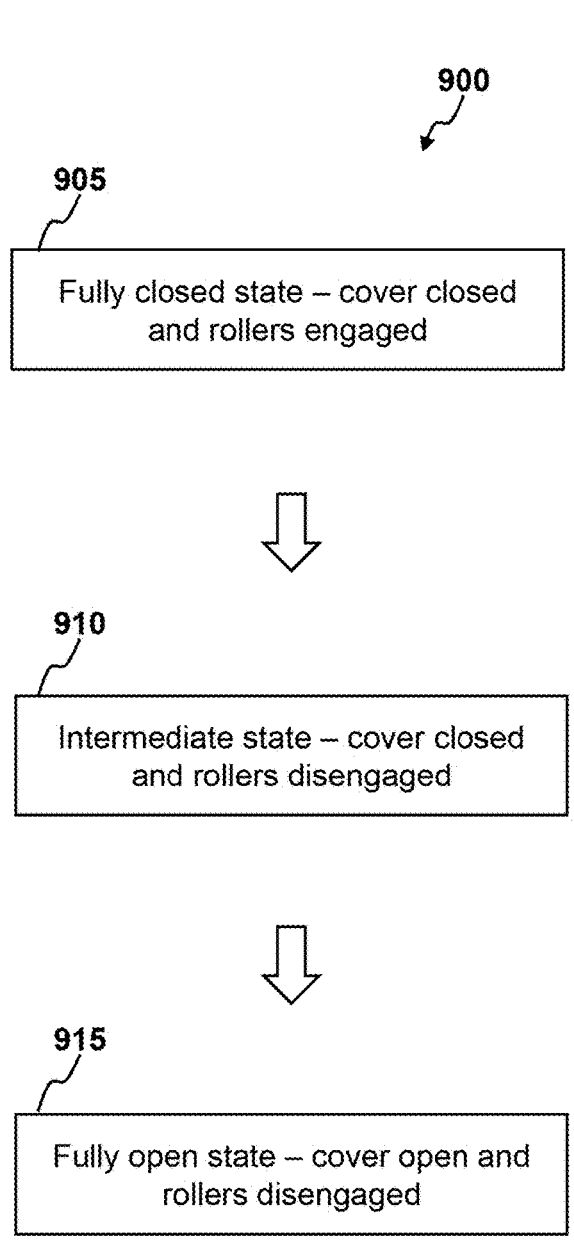
Figure 30B:
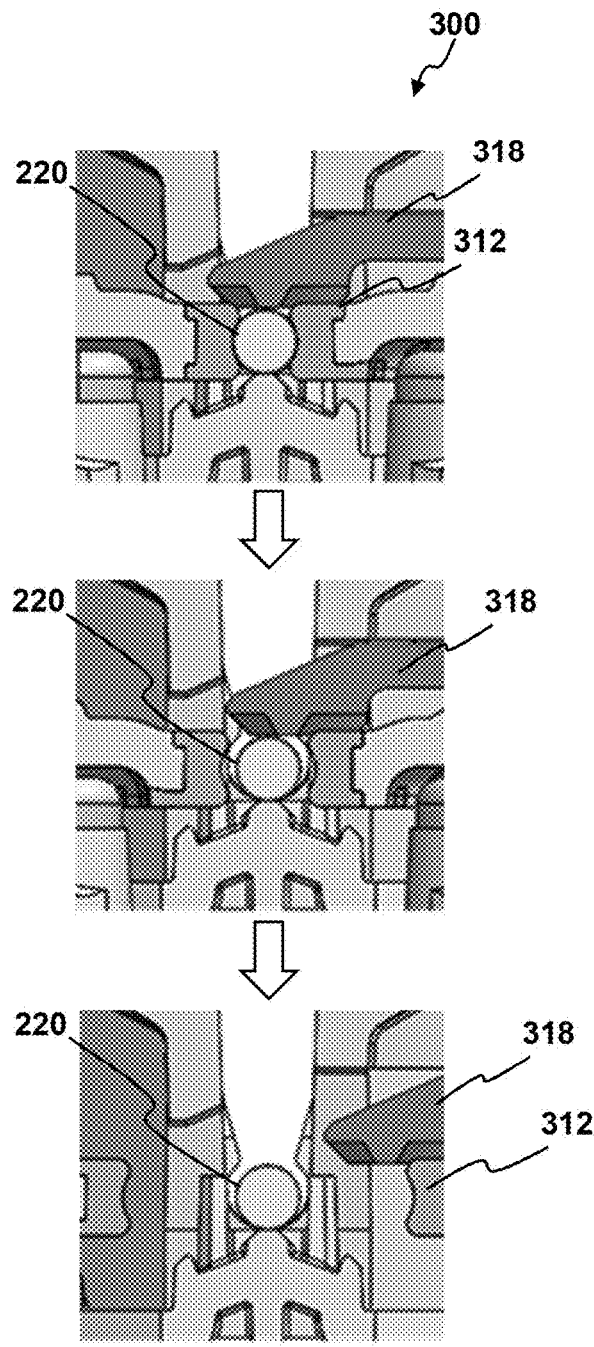

FIGS. 30A-30B illustrate a method 900 of controlling a drive device 300 in various states of operation. FIG. 30A is a flow chart depicting the method 900, and FIG. 30B illustrates a cross section of the drive device 300 at the various states. The method 900 is described in the context of a system 200 (FIGS. 21-22), where the medical instrument 210 is supported and controlled by first robotic arm 202, and the drive device 300 is supported and controlled by second robotic arm 204, but it will be appreciated that the drive device 300 may be controlled robotically or electrically using other architectures.

At block 905, the drive device 300 is actuated to a fully closed state, where the cover 318 is closed and the rollers 312 are engaged with the instrument shaft 220. In this state, the robotic arm or instrument driver controlling drive device 300 can be configured to drive axial motion of the shaft 220 by actuating rollers 312. The drive device 300 may actuate the rollers 312 in either direction against the shaft 220 based on a command or control signal received from the processor to insert or retract the shaft 220. The cover 318 remains closed in this state to help retain the shaft 220 in the channel, for example, to prevent the rollers from ejecting the shaft upwards and laterally out of the channel.

At block 910, the drive device 300 is actuated to an intermediate or partially closed state, where the cover 318 is closed but the rollers 312 are disengaged from the instrument shaft 220. This state may provide a degree of freedom of movement of the elongate shaft 220 independent of the rollers 312, while still retaining the shaft 220 in a loaded configuration with the drive device 300.

The robotic arm or instrument driver controlling the drive device 300 can be configured to actuate the drive device 300 to the intermediate state based on a command or control signal received from the processor to roll the instrument shaft 220. Coordinated operation of the first and second robotic arms may also facilitate such operation. For example, in response to the roll command, the second robotic arm may actuate the drive device 300 to the intermediate state, and the first robotic arm may rotate the elongate shaft 220 about its longitudinal axis. The first robotic arm may rotate the elongate shaft 220 about its longitudinal axis using any suitable technique, such as operation of roll mechanisms with the medical instrument, rotation of the first robotic arm, or rotation of the instrument driver at the end of the robotic arm.

Alternatively, or in combination, the robotic arm or instrument driver controlling the drive device 300 can be configured to actuate the drive device 300 to the intermediate state based on a command or control signal received from the processor to move the robotic arm holding the drive device 300. For example, the second robotic arm 204 may have an admittance or manual arm manipulation mode that allows the arm to be repositioned. If the robotic arm is docked with the access sheath, this can be used to reposition the access sheath within the patient, or move the access sheath relative to the instrument shaft, by separating the rollers 312 and allowing the shaft 220 to slide freely independent of the rollers 312.

To actuate the drive device 300 to the intermediate state, the robotic arm controlling drive device 300 can be configured to partially rotate the open/close drive input to pivot the carrier plates and separate the rollers 312 from the shaft 220, without fully moving the carrier plates, so that the cover 318 keeps the channel closed. Alternatively, the cover 318 may be independently controlled as previously described.

At block 915, the drive device 300 is actuated to a fully open state, where the cover 318 is open and the rollers 312 are disengaged from the instrument shaft 220. This state may allow the instrument shaft 220 to be easily loaded into or out of the channel in a lateral direction. The robotic arm or instrument driver controlling the drive device 300 can be configured to actuate the drive device 300 to the fully open state based on a command or control signal received from the processor to load or unload the instrument shaft 220. This can be based on, for example, a user input for this command, or a command based on detecting attachment of the drive device 300 (e.g., using magnets in the drive device).

Figure 31:
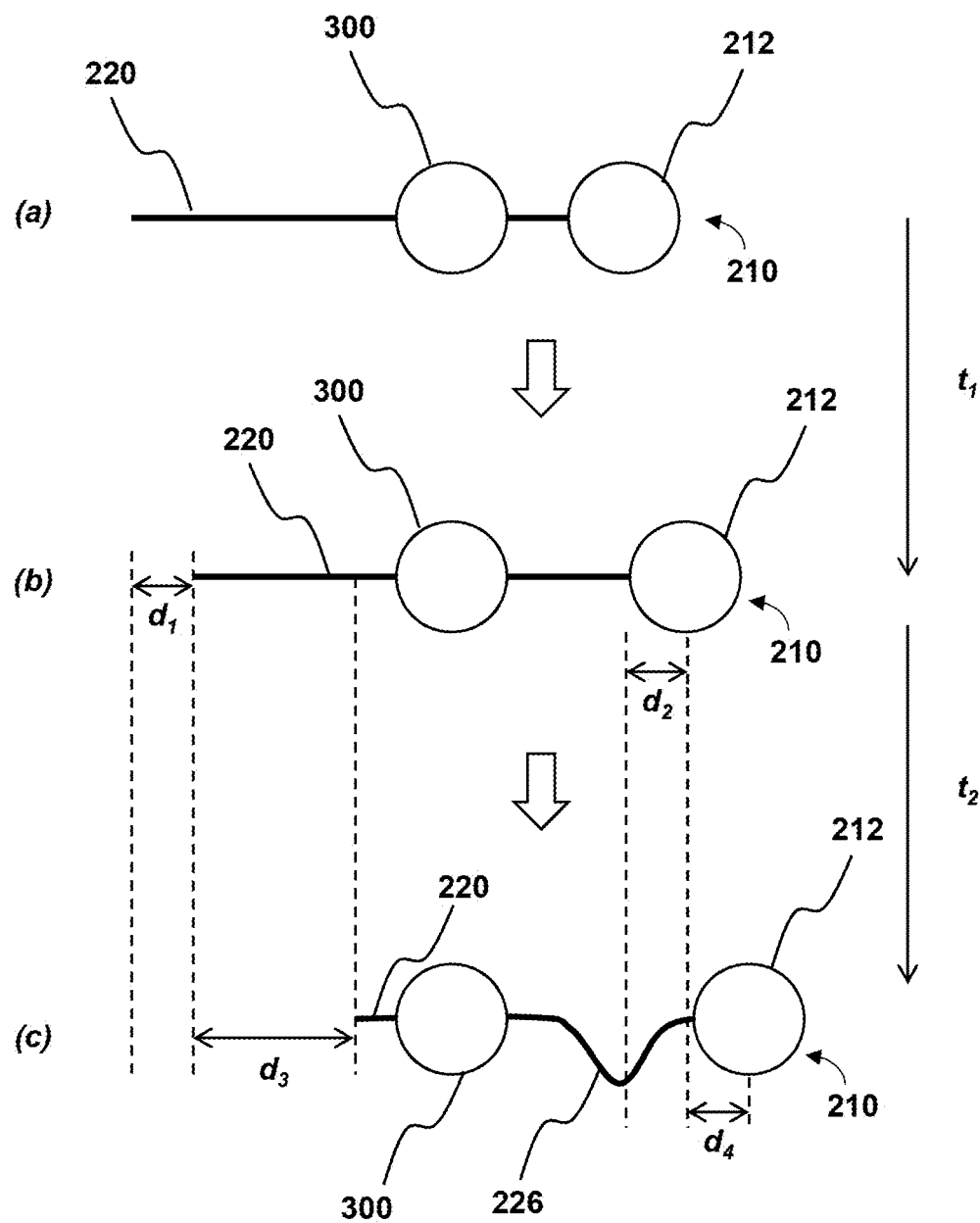
FIG. 31 is a schematic illustration of an axial drive system in various states of fast or slow driving.
Figure 32:
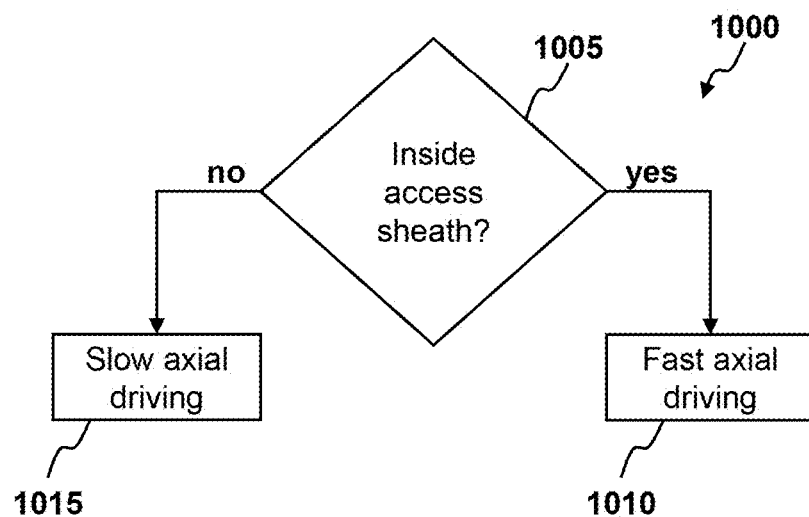
FIG. 32 is a flow chart illustrating an exemplary process for transitioning between fast or slow driving speeds in an axial drive system.
Figure 33:
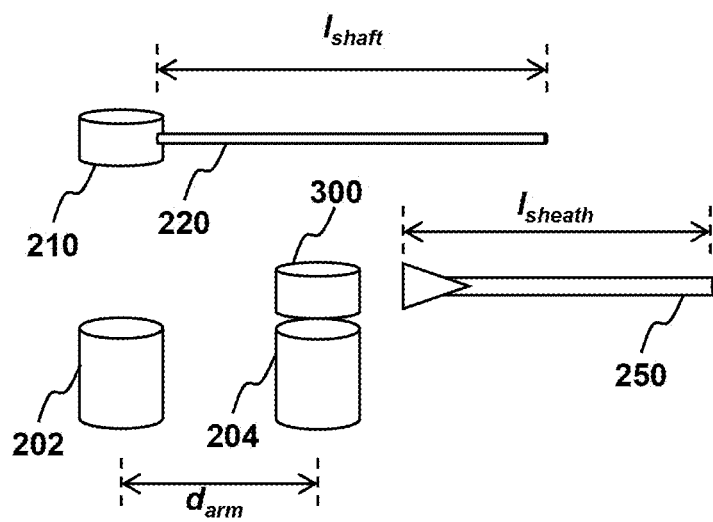
FIG. 33 is an illustration of some parameters that may be utilized by the robotic system to automatically determine whether to transition between fast or slow axial driving speeds for insertion or retraction of an elongated shaft.

FIG. 31 is a schematic illustration of an axial drive system in various states of fast or slow driving. FIG. 32 is a flow chart illustrating an exemplary process for transitioning between fast or slow driving speeds in an axial drive system, and FIG. 33 is an illustration of some parameters that may be utilized by the robotic system to automatically determine whether to transition between fast or slow axial driving speeds for insertion or retraction of an elongated shaft.

With reference to FIG. 31, an exemplary sequence of operation for drive device 300 and medical instrument 210 is depicted, which can involve coordinated operation of the drive device 300 and movement of the instrument base 212 using first and second robotic arms 202, 204 (FIGS. 21-22).

From stage (a) to stage (b), the drive device 300 is operated in coordination with movement instrument base 212 to retract the instrument shaft 220 at a slow rate or speed by a distance or path length of $d_1$ over a time period of $t_1$. Here, the first robotic arm 202 (FIG. 21-22) can be retracted proximally or away from the drive device 300 to move the instrument base 212 by a distance $d_2$ that is substantially the same as the shaft retraction distance of $d_1$ over that same time period. Accordingly, no service loop is generated or expanded in the portion of the shaft 220 between the drive device 300 and instrument base 212 during this time period, and the shaft 220 is driven (retracted) at a slow axial motion rate that can be defined by the change in distance of the distal tip of the shaft over time $d_1/t_1$. Although the drive device 300 may optionally be disengaged from the shaft 220, and axial motion of the shaft 220 can be achieved through movement of the instrument base 212 or first robotic arm alone during the slow movement period, coordinating movement of the instrument base 212 and the first robotic arm 202 with operation of the drive device 300 can help mitigate shaft buckling by maintaining a generally taut portion of the instrument shaft 220 between the drive device 300 and instrument base 212.

From stage (b) to stage (c), the drive device 300 is operated in coordination with movement of instrument base 212 to retract the instrument shaft 220 at a fast rate or speed by a distance or path length of $d_3$ over a time period of $t_2$. Here, the first robotic arm 202 (FIG. 21-22) can be retracted proximally or away from the drive device 300 to move the instrument base 212 by a distance $d_4$ that is less than the shaft retraction distance of $d_3$ over that same time period, such that the instrument shaft 220 is retracted at a rate that is faster than a movement rate of the instrument base 210 or first robotic arm. Operating the drive device 300 to retract the instrument shaft at this fast retraction rate causes service loop 226 to be generated or expanded, providing a greater degree of freedom of movement in the axial direction that is not constrained by the movement or articulation capabilities of the first robotic arm or other movable support for instrument base 212. Accordingly, a service loop is generated or expanded in the portion of the shaft 220 between the drive device 300 and instrument base 212 during this time period, and the shaft 220 is driven (retracted) at a fast axial motion rate that can be defined by the change in distance of the distal tip of the shaft over time $d_3/t_2$. Although the instrument base 212 may optionally remain stationary during the faster movement rate, coordinating movement of the instrument base 212 and the first robotic arm 202 with operation of the drive device 300 may also help mitigate sharp bends in the instrument shaft 220 that could form with the generation or expansion of service loop 226 at a high rate without increasing the distance between the instrument base 212 and the drive device 300.

The sequence (a)-(c) shown in FIG. 31 depicts a transition from slow to fast axial motion during a retraction of the shaft 220, where service loop 226 is generated or expanded to create slack in the shaft 220. The sequence can generally be inverted for insertion of the shaft 220 to transition from fast to slow inserting axial motion. For example, during insertion, service loop 226 may be contracted or slack may be taken up by the drive device 300 during a period of fast insertion. The instrument base 212 or first robotic arm 202 may be moved distally or towards the drive device in coordination with operation of the drive device. The system may then transition to a slow insertion rate where the service loop is eliminated or slack is fully taken up, or the shaft 220 is inserted at a rate that is equal to or less then the movement rate of the instrument base 212 or first robotic arm 202.

It should be understood that the shaft 220 may follow a tortuous path within the patient lumen or anatomy, such that the distances in these examples are defined by changes along the tortuous path or curved length of the shaft, and not necessarily the distance of a straight line connecting the distal tip between the two positions. Accordingly, the distance may be defined by the path length that the shaft travels.

Likewise, the distance of the robotic arm or instrument base 212 may refer to the path length of travel for the robotic arm or instrument base.

FIGS. 32-33 depict an embodiment of a method 1000 and related parameters associated with the method for controlling axial motion of a shaft using a robotic axial drive system. The method 1000 and any other methods described herein may be implemented by a processor of the robotic system executing instructions stored in a computer readable medium such that, when executed, the processor controls components of the robotic system, such as arms, instrument drivers, and/or scopes, to implement the method.

Referring to FIG. 32, at block 1005, method 1000 includes detecting whether the distal tip of the shaft 220 is positioned within the access sheath 250. As described herein, the access sheath 250 may provide a conduit through which shaft 220 can be inserted, and the access sheath 250 may protect patient tissue so that the shaft 220 may be safely inserted at a fast insertion rate. Accordingly, at block 1010, based on detecting that the distal tip is within a safe zone of the access sheath 250, the system drives the shaft axially (e.g., inserts or retracts the shaft) at a fast axial motion rate. At block 1015, based on detecting that the distal tip is within outside of the safe zone of access sheath 250, for example beyond the distal end of the access sheath, the system drives the shaft axially (e.g., inserts or retracts the shaft) at a slow axial motion rate.

FIG. 33 depicts examples of information that may be used by the system to define a safe zone within the access sheath 250 and automatically detect whether the current position of the distal tip of the shaft is within or outside of the access sheath. As seen in FIG. 33, various geometric information associated with components of the system may be used to detect the current position of the shaft 220 relative to the access sheath 250, and to determine an axial motion driving speed for the shaft 220. Such geometric information includes, for example, a length $l_{shaft}$ of the shaft 220 of the instrument 210, a length $l_{sheath}$ of the access sheath 250, and/or robot position information $d_{arm}$. Here, the position information $d_{arm}$ includes the distance between distal ends of the first and second robotic arms 202, 204, which corresponds to the distance between the distal drive device 300 and the instrument base 210. The position information of the robotic arms 202, 204 may, for example, be determined based on kinematic information associated with each arm, such as encoder information captured at a series of joints of the arm. The lengths of the shaft 220 and the sheath 250 may, for example, each be determined based on user input information (e.g., user entered lengths or tools types), known or stored information defining the lengths of the tools, and/or automatic identification of the tools or tools lengths that can be detected and associated with the tools when such tools are attached to the robotic system. Robot driver information, such as encoder data of the drive outputs associated with the second robotic arm 204 holding the drive device 300, can additionally or alternatively be used to determine the shaft position.

In an example where the shaft 220 is engaged with the drive device 300, the instrument base 210 is mounted to the first robotic arm 202, the drive device 300 is mounted to the second robotic arm 204, and the shaft 220 is held between the arms without a service loop in the portion between the arms, the position of the distal tip of the shaft 220 can be determined by subtracting the position information $d_{arm}$ from the length $l_{shaft}$ of the shaft 220. Where the result exceeds the length $l_{sheath}$ of the access sheath 250, the system can detect that the distal tip is beyond the access sheath 250 and that the shaft 220 should be driven using slow axial motion. Where the result is less than the length $l_{sheath}$ of the access sheath 250 (optionally by a sufficient pre-defined tolerance) the system can detect that the distal tip is within the access sheath 250 and that the shaft 220 should or can be driven using fast axial motion.

It will be appreciated that this is an illustrative example, and other types of geometric information or robot information may be used to automatically detect the position of the shaft. For example, in some embodiments image information captured with medical instrument 210 (e.g., vision data from a tip of an endoscope), may be processed and analyzed to determine whether the captured image data corresponds to within or outside the sheath. Such image information may be used alone or in combination with the geometric information described above. Additionally or alternatively, the system may use data captured from other types of sensors.

It should also be understood that detection of the position of shaft relative to the access sheath may be used as a condition forming a basis for the driving speed. In some embodiments, the position of the shaft relative to the access sheath is not necessarily the only condition for determining driving speed, and is not necessarily a sufficient condition for determining whether to transition to a fast or slow driving speed. For example, the system may employ other conditions to provide safety or provide optimum usability and control of the axial driving speed.

It should also be understood that the fast or slow axial motion rates described herein may encompass a range of rates, and that the rate of axial motion may vary within fast axial motion or slow axial motion. Accordingly, fast axial motion does not necessarily refer to a single rate, but can encompass a range of varying rates where the fast axial motion rate is faster than the slow axial motion rate, and where the fast axial motion permits a service loop in the shaft to be expanded or contracted with the drive system. Likewise, slow axial motion does not necessarily refer to a single rate, but can encompass a range of varying rates where the slow axial motion rate is slower than the fast axial motion rate.

3. Implementing Systems and Terminology

Implementations disclosed herein provide systems, methods and apparatus for driving axial motion of an elongated or flexible shaft of a medical instrument.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
    a medical instrument comprising an instrument base and an elongated shaft configured for insertion into a patient;
    a first robotic arm, wherein the instrument base of the medical instrument is attached to the first robotic arm and the first robotic arm is configured to move the instrument base;
    a second robotic arm;
    a drive device attached to the second robotic arm and distal relative to the instrument base, wherein the drive device is configured to engage with the elongated shaft and drive axial motion of the elongated shaft; and
    a processor configured to, during a first period of axial motion:
        cause the drive device to move the elongated shaft along a longitudinal axis of the elongated shaft at a first axial motion rate that is greater than a linear movement rate of the first robotic arm.

2. The system of claim 1, wherein, during the first period of axial motion, a portion of the elongated shaft of the medical instrument between the instrument base and the drive device has a length greater than a distance between the instrument base and the drive device such that the portion of the elongated shaft forms a service loop.

3. The system of claim 2, wherein, during the first period of axial motion, a rate of change of a length of the service loop is greater than a rate of change of the distance between the between the instrument base and the drive device.

4. The system of claim 1, wherein the axial motion comprises at least one of retraction or insertion of the elongated shaft.

5. The system of claim 1, wherein the processor is configured to drive axial motion of the elongated shaft at the first axial motion rate when a distal tip of the elongated shaft is positioned within an access sheath.

6. The system of claim 1, wherein the processor is configured to, during a second period of axial motion:
    drive axial motion of the elongated shaft of the medical instrument with the drive device at a second axial motion rate that is equal to or less than the linear movement rate of the first robotic arm.

7. The system of claim 6, wherein, during the second period of axial motion, a portion of the elongated shaft of the medical instrument between the instrument base and the drive device has a length substantially equal to a distance between the instrument base and the drive device such that the portion of the elongated shaft does not form a service loop.

8. The system of claim 6, wherein, during the second period of axial motion, a portion of the elongated shaft of the medical instrument between the instrument base and the drive device has a length greater than a distance between the instrument base and the drive device such that the portion of the elongated shaft forms a service loop.

9. The system of claim 6, wherein, during the second period of axial motion, a rate of change of the length is equal to or less than a rate of change of the distance between the between the instrument base and the drive device.

10. The system of claim 6, wherein the processor is configured to drive axial motion of the elongated shaft at the second axial motion rate when a distal tip of the elongated shaft is positioned beyond an access sheath.

11. The system of claim 1, wherein:
    the drive device is configured to attach to an access sheath configured to be inserted into the patient; and
    the elongated shaft is configured to be inserted into the patient through the access sheath.

12. The system of claim 11, wherein the drive device comprises a clip configured to attach to a proximal end of the access sheath.

13. The system of claim 11, wherein the drive device is configured to:
    withdraw a distal tip of the elongated shaft from a proximal end of the access sheath; and
    reinsert the distal tip of the elongated shaft into the proximal end of the access sheath.

14. The system of claim 1, further comprising an instrument driver comprising a plurality of drive outputs positioned at a distal end of the second robotic arm, wherein the drive device comprises a plurality of drive inputs configured to engage the plurality of drive outputs of the instrument driver.

15. The system of claim 14, further comprising a sterile adapter positioned between the instrument driver and the drive device.

16. The system of claim 1, wherein the drive device comprises a pair of opposing rollers configured to drive axial motion of the elongated shaft.

17. The system of claim 1, wherein the drive device comprises:
- a body comprising a channel configured to receive the elongated shaft of the medical instrument;
- a roller configured to engage with the elongated shaft, wherein the second robotic arm is configured to rotate the roller to drive axial motion of the elongated shaft received in the channel; and
- a pivotable carrier supporting the roller, wherein the second robotic arm is configured to pivot the carrier to selectively engage or disengage the roller with the elongated shaft.

18. The system of claim 1, wherein, based on receiving a roll command to roll the elongated shaft, the processor is configured to cause:
- the first robotic arm to rotate the elongated shaft about the longitudinal axis of the elongated shaft; and
- the second robotic arm to disengage the drive device from the elongated shaft.

19. A robotic medical system, comprising:
- a medical instrument comprising an instrument base and a flexible shaft configured for insertion into a patient;
- a first robotic arm attachable to the instrument base of the medical instrument;
- a drive device configured to engage the flexible shaft; and
- a second robotic arm attachable to the drive device, wherein the second robotic arm is configured to operate the drive device to drive axial motion of the flexible shaft,
- wherein the first robotic arm is configured to move closer to the second robotic arm during an insertion motion where the drive device moves the flexible shaft in an insertion direction and move farther from the second robotic arm during a retraction motion where the drive device moves the flexible shaft in a retraction direction, and wherein the drive device is configured to drive axial motion of the flexible shaft at a rate faster than a rate of motion of the first robotic arm during at least one of the insertion motion or retraction motion.

20. The robotic medical system of claim 19, wherein the second robotic arm is configured to disengage the drive device from the flexible shaft while retaining the flexible shaft in the drive device with a robotically-actuated cover.

21. The robotic medical system of claim 19, wherein the second robotic arm is configured to control a rate of the axial motion based on a position of a tip of the flexible shaft relative to an access sheath.

22. The robotic medical system of claim 19, wherein the second robotic arm is configured to expand or contract a service loop in a portion of the flexible shaft between the first and second robotic arms.

23. The robotic medical system of claim 19, wherein the medical instrument is an endoscope.

24. A robotic medical system, comprising:
- a first robotic arm configured to support an instrument base of a medical instrument, the medical instrument comprising an elongated shaft extending from the instrument base; and
- a second robotic arm configured to operate one or more rollers engageable with the elongated shaft to drive axial motion of the elongated shaft along a longitudinal axis of the elongated shaft at an axial motion rate that is greater than a movement rate of the first robotic arm.

25. The robotic medical system of claim 24, wherein the one or more rollers comprise a pair of opposing rollers of a drive device attached to the second robotic arm and configured to drive axial motion of the elongated shaft.

26. The robotic medical system of claim 25, wherein the second robotic arm is configured to disengage the drive device from the elongated shaft and retain the flexible shaft in the drive device with a robotically-actuated cover.

27. A method, comprising:
- supporting, with a first robotic arm, an instrument base of a medical instrument;
- driving, with a second robotic arm, axial motion of an elongated shaft of the medical instrument along a longitudinal axis of the elongated shaft; and
- while driving the elongated shaft, moving the first robotic arm closer to or farther away from the second robotic arm at a rate that is slower than the axial motion of the elongated shaft.

28. The method of claim 27, wherein driving the axial motion comprises operating a pair of opposing rollers with the second robotic arm.

29. The method of claim 27, wherein the second robotic arm is configured to disengage a drive device from the elongated shaft while retaining the elongated shaft in the drive device with a robotically-actuated cover.

* * * * *